US008697661B2

(12) United States Patent
Kritikou

(10) Patent No.: US 8,697,661 B2
(45) Date of Patent: Apr. 15, 2014

(54) USE OF SPINOSYNS AND SPINOSYN COMPOSITIONS AGAINST HERPESVIRIDAE VIRAL INFECTIONS

(75) Inventor: Christine Kritikou, Kifissia (GR)

(73) Assignees: Christine Kritikou, Kifissia (GR); Entarco SA, Kifissia (GR)

( * ) Notice: Subject to any disclaimer, the term of this patent is extended or adjusted under 35 U.S.C. 154(b) by 0 days.

(21) Appl. No.: 13/378,927

(22) PCT Filed: Jun. 23, 2010

(86) PCT No.: PCT/IB2010/001713
§ 371 (c)(1),
(2), (4) Date: Jan. 24, 2012

(87) PCT Pub. No.: WO2010/150100
PCT Pub. Date: Dec. 29, 2010

(65) Prior Publication Data
US 2012/0195961 A1    Aug. 2, 2012

Related U.S. Application Data

(60) Provisional application No. 61/220,059, filed on Jun. 24, 2009.

(51) Int. Cl.
*A61K 31/7048* (2006.01)
(52) U.S. Cl.
USPC .......................................................... 514/28
(58) Field of Classification Search
None
See application file for complete search history.

(56) References Cited

U.S. PATENT DOCUMENTS

| 5,202,242 | A  | 4/1993  | Mynderse et al.      |
|-----------|----|---------|----------------------|
| 5,362,634 | A  | 11/1994 | Boeck et al.         |
| 5,496,931 | A  | 3/1996  | Boeck et al.         |
| 5,571,901 | A  | 11/1996 | Boeck et al.         |
| 5,591,606 | A  | 1/1997  | Turner et al.        |
| 5,631,155 | A  | 5/1997  | Turner et al.        |
| 5,670,364 | A  | 9/1997  | Mynderse et al.      |
| 5,670,486 | A  | 9/1997  | Mynderse et al.      |
| 5,767,253 | A  | 6/1998  | Turner et al.        |
| 5,840,861 | A  | 11/1998 | Mynderse et al.      |
| 6,001,981 | A  | 12/1999 | DeAmicis et al.      |
| 6,310,177 | B1 | 10/2001 | Blaschuk et al.      |
| 6,312,717 | B1 | 11/2001 | Molinoff et al.      |
| 6,379,696 | B1 | 4/2002  | Asmussen et al.      |
| 6,465,006 | B1 | 10/2002 | Zhang et al.         |
| 6,512,010 | B1 | 1/2003  | Gale et al.          |
| 6,517,864 | B1 | 2/2003  | Orup Jacobsen et al. |
| 6,544,548 | B1 | 4/2003  | Siller-Jackson et al.|
| 6,589,549 | B2 | 7/2003  | Shih et al.          |
| 6,664,237 | B1 | 12/2003 | Snyder               |
| 6,800,614 | B2 | 10/2004 | Lewer et al.         |
| 6,821,526 | B1 | 11/2004 | Huang                |
| 6,919,464 | B1 | 7/2005  | Crouse et al.        |
| 7,015,001 | B2 | 3/2006  | Baltz et al.         |
| 7,160,865 | B2 | 1/2007  | Lampidis et al.      |
| 7,445,794 | B1 | 11/2008 | Newell et al.        |
| 2003/0181393 | A1 | 9/2003 | Lampidis et al.     |
| 2006/0040877 | A1 | 2/2006 | Burns et al.        |
| 2007/0167379 | A1 | 7/2007 | Hacket et al.       |

FOREIGN PATENT DOCUMENTS

| WO | WO 93/09126     | 5/1993  |
|----|-----------------|---------|
| WO | WO 94/20518     | 9/1994  |
| WO | WO 01/12156 A1  | 2/2001  |
| WO | WO/2005/070126  | 8/2005  |
| WO | WO 2005/112950 A1 | 12/2005 |
| WO | WO/2009/054003  | 4/2009  |
| WO | WO 2009/118663 A2 | 10/2009 |

OTHER PUBLICATIONS

Stebbins, K. E. et al., "Spinosad Insecticide: Subchronic and Chronic Toxicity and Lack of Carcinogenicity in CD-1 Mice," Toxicological Sciences, vol. 65, No. 2, Feb. 2002, pp. 276-287.
Deamicis, Carl V. et al., "Physical and Biological Properties of the Spinosyns: Novel Macrolide Pest-Control Agents From Fermentation," ACS Symposium Series, American Chemical Society/Oxford University Press, United States, vol. 658, Jan. 1, 1997, pp. 144-154.
Shin, Hyun E. et al., "Insecticide Susceptibilities of Anopheles Sinensis (Diptera: Culcidae) Larvae from Panju-Shi, Korea," Korean Journal of Entomology, vol. 33, No. 1, Mar. 2003, pp. 33-17.
PCT International Search Report in corresponding application No. PCT/IB2010/001713, 4 pages, Oct. 18, 2010.
Cavalier-Smith, "The Neomuranorigin of Archaebacteria; The Negibacterial Root of the Universal Tree and Bacterial Megaclassification," International Journal of Systematic and Evolutionary Microbiology, 52: 7-76 (2002).
Berrahal et al., "Canine Leishmaniasis: Identification of Asymptomatic Carriers by Polymerase Chain Reaction and Immunoblotting," American Journal of Tropical Medicine & Hygiene, vol. 55, pp. 273-277 (1996).
Croft et al., "Leishmaniasis—current Chemotherapy and Recent Advances in the Search of Novel Drugs," Trends Parasitol, vol. 19, pp. 502-508 (2003).
Achievements in Public Health, 1900-1999: Control of Infectious Diseases, MMWR Morb Mortal Wkly Rep 1999, 48:621-629.
Nelson, M. I., et al., "The evolution of epidemic influenza," Nat Rev Genetics, vol. 8, pp. 196-205 (2007).
Wang et al., "Ion channel activity of Influenza A Virus M2 Protein: characterization of the Amantadine Block," J. Virol. 67 (9): 5585-5594 (1993).
Lew et al., "Discovery and Development of GS 4104 (Oseltamivir): An Orally Active Influenza Neuraminidase Inhibitor," Med Chem, vol. 7, pp. 663-72 (Jul. 2007).

(Continued)

*Primary Examiner* — James D Anderson
(74) *Attorney, Agent, or Firm* — Finnegan, Henderson, Farabow, Garrett & Dunner, LLP

(57) ABSTRACT

The present invention relates to the use of spinosyns and spinosyn compositions as pharmaceuticals and methods for treatment—including prevention—of protozoan infections and/or disorders relating to a protozoan infection, such as malaria and *leishmania*, viral infections such as Herpes Simplex virus and Influenza virus and neoplastic disorders or cancer. Advantageously, compositions of the invention inhibit protozoan, virus growth and neoplastic cell proliferation with only minimal or no disruption or harm to the host which may be an animal or human.

15 Claims, 24 Drawing Sheets

(56) References Cited

OTHER PUBLICATIONS

Stough et al., "Efficacy and Safety of Spinosad and Permethrin Crème Rinses for Pediculosis Capitis (Head Lice)", Pediatrics, p. 124, vol. e389-e395 (2009).

Kirst et al., Unique Fermentation-Derived Tetracyclic Macrolides, Tetrahedon Letters, A83543A-D, vol. 32, pp. 4839-4842 (1991).

Hahn et al., "Butenyl-Spinosyns, A Natural Example of Genetic Engineering of Antibiotic Biosynthetic Genes," Journal of Industrial Microbiology & Biotechnology, vol. 33, No. 2, pp. 94-104 (Feb. 2006).

Lewer et al, "Discovery of the Butenyl-Spinosyn Insecticides: Novel Macrolides From the New Bacterial Strain *Saccharopolyspora pogona*," Dow Agrosciences, Bioorganic & Medicinal Chemistry, vol. 17, pp. 4185-4196 (2009).

Salgado et al., "Studies on the Mode of Action of Spinosad: The Internal Effective Concentration Dependence of Neural Excitation," Pesticide Biochemistry and Physiology, vol. 60, pp. 103-110 (1998).

Hussain et al., "Biochemical Abnormalities Produced by Spinosad in *Tribolium castaneum* Adult Beetles," Pakistan International Journal of Agriculture & Biology ISSN Print: 1560-8530, 08-267/DMK/2009/11-3-241-244.

Rabea et al., "Toxic Effect and Biochemical Study of Chlorfluazuron, Oxymatrine and Spinosad on Honey Bees," Archives of Environmental Contamination and Toxicology, Springer, New York, pp. 0090-4341 (2009).

Van Dooren et al., "Metabolic Maps and Functions of the Plasmodium Mitochondrion," FEMS Microbiol Rev., vol. 30, No. 4, pp. 596-630 (Jul. 2006).

Mogi et al., "Identification of Mitochondrial Complex II Subunits SDH3 and SDH4 and ATP Synthase Subunits A and B in Plasmodium spp," Mitochondrion, vol. 9, No. 6, pp. 443-53 (Nov. 2009).

Torrentino-Madamet et al., "Microaerophilic Respiratory Metabolism of Plasmodium Falciparum Mitochondrion as a Drug Target," Curr Mol Med., vol. 10, No. 1, pp. 29-46 (Feb. 1, 2010).

Roth, "Buying Time Through Hibernation on Demand," University of Washington School of Medicine, Fred Hutchinson Cancer Research Center-Media Toolkit, Seattle, WA, Apr. 21, 2005.

Chen. et al., "Modulation of Electron Transport Protects Cardiac Mitochondria and Decreases Myocardial Injury During Ischemia and Reperfusion," Am J Physiol Cell Physiol, vol. 292, pp. C137-C147 (Sep. 13, 2006).

Engleman, Cytotechnology, vol. 25, No. 1 (1997).

Van Schooten et al., Molecular Medicine Today, p. 255 (Jun. 1997).

Steinman, Experimental Hematology, vol. 24, p. 849 (1996).

Gluckman et al., "In Vitro Generation of Human Dendritic Cells and Cell Therapy", Cytokines Cell Mol Ther., Sep. 1997, pp. 187-96, vol. 3, No. 3.

Fraley et al., "New Generation Liposomes: The Engineering of an Effect Vehicle for Intracellular Delivery of Nucleic Acids", Trends in Biochemical Sciences, Mar. 1981, pp. 77-80.

Bundgaard et al., "Design and Application of Prodrugs" in A Textbook of Drug Design and Development, Eds. Harwood Academic Publishers, pp. 113-191 (1991).

Trauth et al., "Monoclonal Antibody-Mediated Tumor Regression by Induction of Apoptosis", Science, Jul. 21, 1989, pp. 301-304, vol. 245.

Technical Workshop on Highly Pathogenic Avian Influenza and Human H5N1 Infection, Jun. 27-29, 2007, Rome, A. Croiser, E. Mumford, N. Shindo, C. Steffan, S. Martin, K. Fukuda WHO.

Gillissen et al., "Early Therapy with the Neuraminidase Inhibitor Oseltamivir Maximizes its Efficacy in Influenza Treatment," Med Microbiol Immunol, 191:165-168, 2002.

DMSO vehicle    20μg/mL spinosad (drug)
n=1
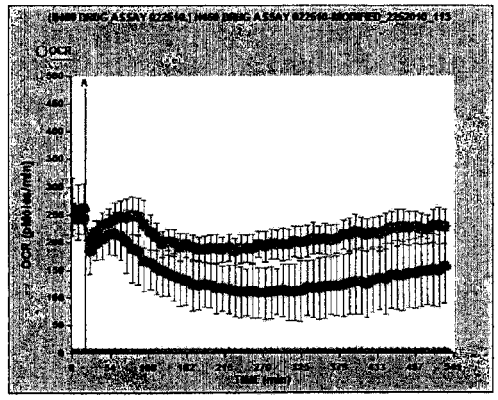 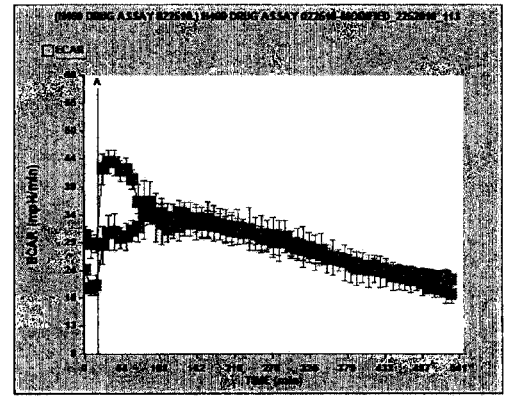
n=2
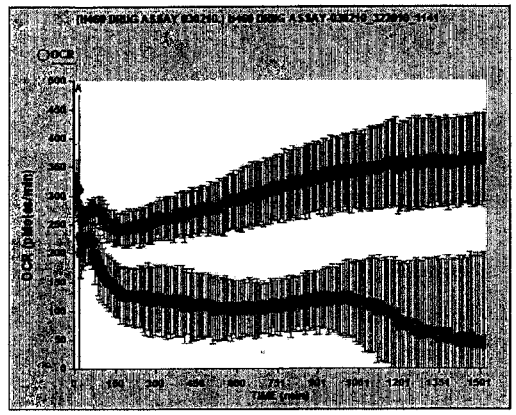 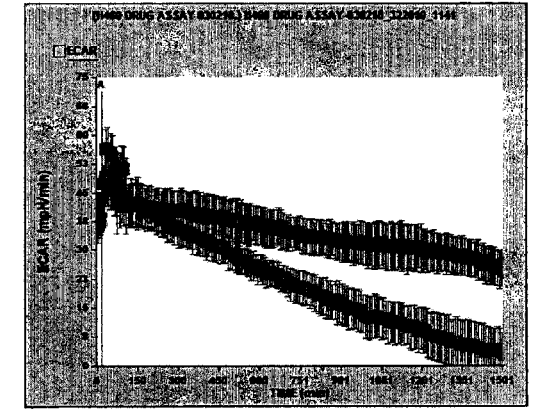
n=3
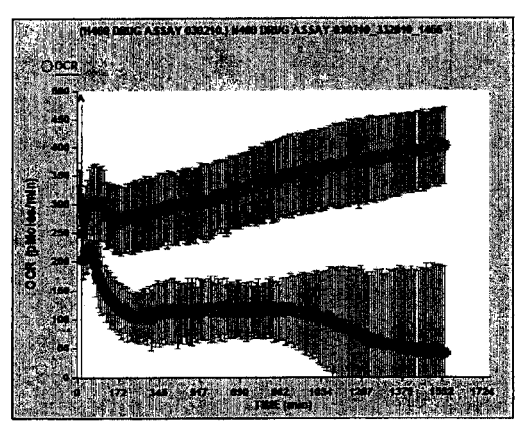 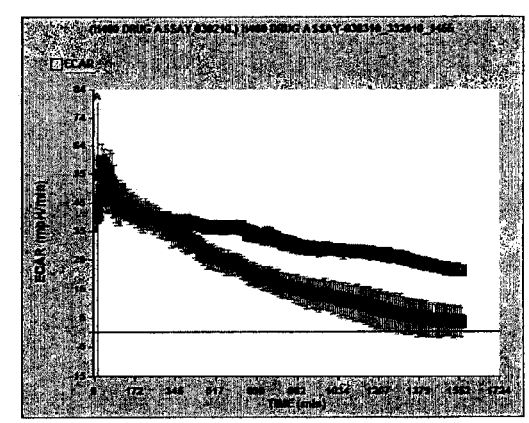
Time course of spinosad at a concentration of 20μg/mL on OCR and
ECAR of H460 cells (replicate n=1 is focused on 8 hours period )
*FIG. 8A*

Untreated
n=1
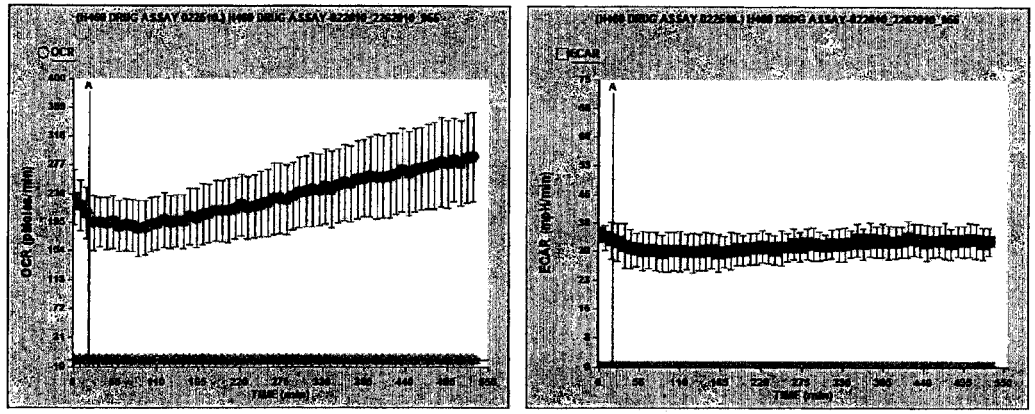
n=2
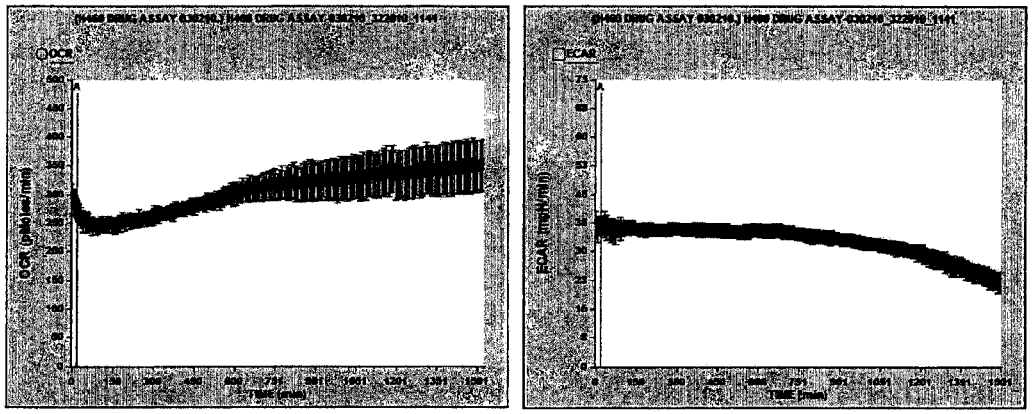
OCR and ECAR measurements on untreated H460 cells injected with assay media.
*FIG. 8B*

Glycolytic inhibitor 2-deoxyglucose

Time course of cells treated with 2-deoxyglucose (representative sample from a single plate).

Blank with spinosad at 20µg/mL.

Blank wells injected with spinosad at 20 µg/mL and the corresponding OCR and ECAR measurements from one plate.

Effect of spinosad (Compound #0043) on OCR in isolated mitochondria.
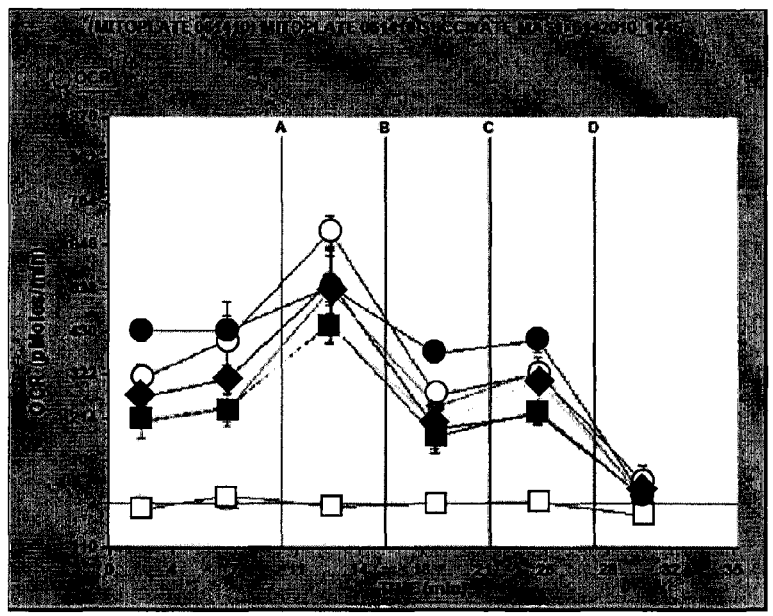
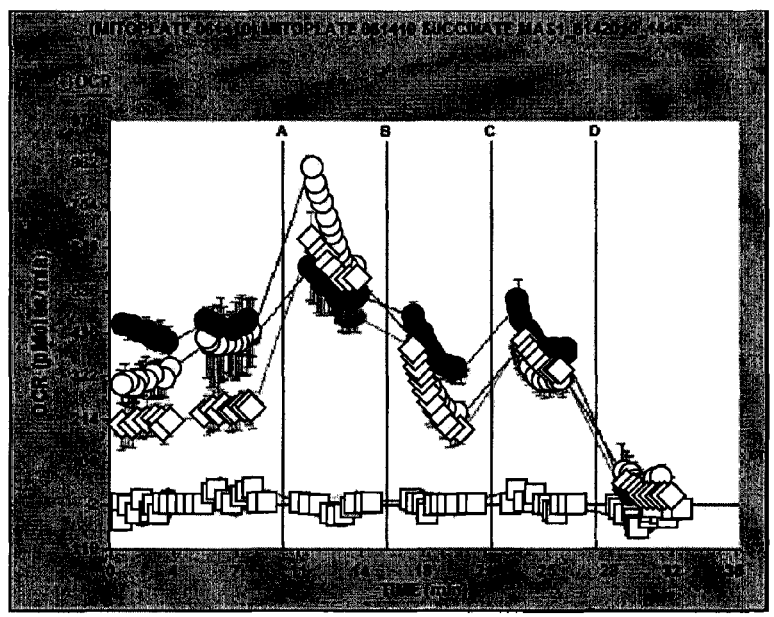
- ○ UNTREATED
- ◆ DMSO TREATED
- ■ 10μg/mL TREATED
- ☐ 20μg/mL TREATED
- ◇ 40μg/mL TREATED
- ● 80μg/mL TREATED
*FIG. 9*

Effect of the Entarco drug (spinosad) 10 μg/ml and 20 μg/ml on OCR and ECAR in H460 cells 7.6 hours post treatment.

SDS-PAGE of samples untreated, DMSO treated and spinosad 10/20/40/80 μg/mL treated that were analyzed by the Seahorse XF24 analyzer.

USE OF SPINOSYNS AND SPINOSYN COMPOSITIONS AGAINST HERPESVIRIDAE VIRAL INFECTIONS

This is a National Stage Application under 35 U.S.C. §371 of International Application No. PCT/IB2010/001713 filed Jun. 23, 2010, which claims the benefit of priority to U.S. Provisional Patent Application No. 61/220,059 filed Jun. 24, 2009, both of which are incorporated herein by reference.

The present invention relates to the use of spinosyns and spinosyn compositions as pharmaceuticals and methods for the prophylaxis (prevention) and treatment of protozoan infections and/or disorders relating to a protozoan infection, such as for example malaria and *leishmania*, viral infections such as for example Herpes Simplex virus and Influenza virus and neoplastic disorders. Advantageously, compositions of the invention inhibit protozoan and virus growth and neoplastic cell viability and proliferation with only minimal or no disruption or harm to the host which may be an animal or human.

Protozoa are singled-celled eukaryotic (i.e., possessing a well-defined nucleus) organisms that can infect humans and animals. They are among the simplest of all living organisms. All protozoa possess at least one nucleus, and many species are multinucleate. Parasitic protozoa feed in a variety of ways. Many live in the nutrient-rich medium of the body fluids—e.g., the blood or cells of their host. *Plasmodium*, for example, engulfs portions of the red blood cells or liver cells in which they live.

Some clinically important representatives include the genus *Plasmodium* spp., *Leishmania* spp., *Toxoplasma gondii, Babesia* spp., *Cryptosporidium* spp., *Sarcocystis* spp., *Coccidea* spp., *Naegleria* spp., *Giardia lamblia, Cyclospora cayetanensis, Isospora belli, Trichomonas vaginalis* and *Trypanosoma* spp.

Protozoa cause serious diseases in humans and animals. For example, protozoans belonging to the infrakingdom Excavata and phylums Euglenozoa, Percolozoa, Metamonada, (Cavalier-Smith, "The Neomuranorigin of Archaebacteria; The Negibacterial Root of the Universal Tree and Bacterial Megaclassification." *International Journal of Systematic and Evolutionary Microbiology,* 52: 7-76, 2002,) may cause trypanosomiasis, primary amoebic meningoencephalitis (caused by *naegleria fowleri* protozoan), leishmaniasis, and trichomoniasis. Protozoan belonging to the phylum apicomplexa, Id., may cause malaria, babesiosis, cryptosporidiosis, toxoplasmosis, isosporiasis, cyclosporiasis, sarcosporidiosis, coccidiosis.

Trypanosomiasis, a neglected tropical disease (NTD) according to WHO, is the name of several diseases in vertebrates, caused by parasitic protozoan trypanosomes. *Trypanosoma brucei*, a parasitic protist species that belongs to the genus *Trypanosoma*, phylum Euglenozoa, infrakingdom Excavata, causes African trypanosomiasis in humans and nagana in animals in Africa. There are 3 sub-species of *T. brucei: T. b. brucei, T. b. gambiense* and *T. b. rhodesiense*. These obligate parasites have two hosts—an insect vector and mammalian host. Because of the large difference between these hosts, the trypanosome undergoes complex changes during its life cycle to facilitate its survival in the insect gut and the mammalian bloodstream. Glycolysis is essential to the parasitic protozoan *Trypanosoma brucei*. The first step in this metabolic pathway is mediated by hexokinase. More than 66 million women, men, and children in 36 countries of sub-Saharan Africa suffer from trypanosomiasis. The other human form of trypanosomiasis, called Chagas disease, causes 21,000 deaths per year mainly in Latin America. There is an urgent need for the development of new drug therapies as current treatments can prove fatal to the patient.

Toxoplasmosis is among the most common parasitic diseases of man. Serosurveys suggest prevalence rates as high as 70-90% in many areas of both the developing and developed world. Between 10-45% of Americans become infected at some point in their lives. *Toxoplasma gondii* is the causative agent in toxoplasmosis. In contrast to the mild clinical symptoms of infection seen in a healthy individual with an intact immune system, hosts with weakened, or otherwise compromised, immune systems can have serious clinical effects from *toxoplasma* infection.

Leishmaniasis, a neglected tropical disease (NTD) according to WHO, is a life-threatening disease caused by *Leishmania* spp. that is a major health problem in much of the world, including Brazil, China, East Africa, India and areas of the Middle East. The disease is also endemic in the Mediterranean region, including southern France, Italy, Greece, Spain, Portugal and North Africa. An estimated 10-15 million people are infected, and 400,000 new cases occur each year. *Leishmania* organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. Visceral leishmaniasis, also called kala-azar, is produced by several subspecies of *L. donovani*. This form of the disease is systemic, primarily affecting the liver, spleen, bone marrow, and other viscera. The disease is usually fatal if not treated. Cutaneous leishmaniasis, the most common form, causes a sore at the bite site which heals in a few months to a year, leaving an unpleasant looking scar. This form can progress to any of the other three forms. Diffuse cutaneous leishmaniasis produces widespread skin lesions which resemble leprosy and is particularly difficult to treat. Mucocutaneous leishmaniasis begins with skin ulcers which spread causing tissue damage, particularly to the nose and mouth.

There are 20 species of *Leishmania* that infect humans, including *L. donovani, L. chagasi, L. infantum, L. major, L. amazonensis, L. braziliensis, L. panamensis, L. mexicana, L. tropica*, and *L. guyanensis.*

The life cycles of members of the genus involve a vertebrate host and a vector (a sand fly) that transmits the parasite between vertebrate hosts. Leishmaniasis is transmitted by the bite of female phlebotomine sandflies. The sandflies inject the infective stage, metacyclic promastigotes, during blood meals. Metacyclic promastigotes that reach the puncture wound are phagocytized by macrophages and transform into amastigotes. Amastigotes multiply in infected cells and affect different tissues, depending, in part, on which *Leishmania* species is involved. These differing tissue specificities cause the differing clinical manifestations of the various forms of leishmaniasis. Sandflies become infected during blood meals on an infected host when they ingest macrophages infected with amastigotes. In the sandfly's midgut, the parasites differentiate into promastigotes, which multiply, differentiate into metacyclic promastigotes and migrate to the proboscis.

Leishmaniasis is considered to be one of the opportunist diseases of AIDS. Approximately 1500 cases of HIV/*Leishmania* co-infection are counted in the south of Europe which represents 90% of the reported cases in the world, with Spain being the country the most affected, with approximately 60% of these cases. The cases of co-infection AIDS/leishmaniasis pose a serious public health problem to the extent that the available therapeutics are less effective among AIDS patients and immunocompromised persons.

In the Mediterranean region, the domestic dog is the main reservoir of the parasite. Canine leishmaniasis, which is a common pathology of the areas surrounding the Mediterranean, manifests itself in various clinical forms which often lead to the death of the animal. The prevalence of canine leishmaniasis can reach 30% of the canine population in some peripheral urban zones. According to Berrahal et al., "Canine Leishmaniasis: Identification of Asymptomatic Carriers by Polymerase Chain Reaction and Immunoblotting," *American Journal of Tropical Medicine & Hygiene*, 55: 273-277 (1996), 85% of dogs are PCR (Polymerase Chain Reaction) positive in the endemic zone.

At present, there are no effective immunoprophylactic treatments against *Leishmania* and the generic, antimony-based drug treatments are plagued with low efficacy, high toxicity and widespread resistance, Croft and Coombs, "Leishmaniasis-current Chemotherapy and Recent Advances in the Search for Novel Drugs," *Trends Parasitol*, 19:502-508, 2003.

Additional important protozoans include the malaria parasite *Plasmodium* spp. The World Health Organization (WHO) estimates that up to 300 million people are infected by malaria each year resulting in up to one million deaths. In the highest risk group, African children under the age of five, malaria claims a young life every 30 seconds. *Plasmodium falciparum* causes a severe form of human malaria and is responsible for nearly all malaria-specific mortality. Resistance of *Plasmodium* to anti-malarial drugs is an increasingly serious problem in fighting the disease. There is still no vaccine available.

The malarial parasites are species-specific. Parasites with which human beings can be infected, include *Plasmodium falciparum; Plasmodium vivax; Plasmodium malariae; Plasmodium ovale* and more recently *Plasmodium Knowlesi. Plasmodium* sporozoites into the mammalian host. The *plasmodium* protozoa are transmitted through the bite of infected female mosquitoes of the genus *Anopheles*, and following an initial asymptomatic localization and incubation in the liver, the parasites enter circulating erythrocytes and reside within these cells. The protozoa replicate inside the blood cells, ultimately inducing cytolysis and release of toxic metabolic byproducts into the blood stream. Mortality is almost exclusively attributable to infection by *P. falciparum*, which produces specific proteins that embed into the cell membrane of the infected erythrocyte. These cells bind to pre-venous capillaries, resulting in obstruction of blood vessels in many areas of the body. Of significant concern is the increasing incidence of *P. falciparum* parasites resistant to existing drugs (chloroquine, mefloquine, sulfadoxime/pyrimethamine artemisinin), with strains now reported that are resistant to all known anti-malarial therapies, potentially foreshadowing devastating consequences if new treatments are not identified.

Thus, the treatment of these parasitic diseases over the long term will depend on the discovery of new therapeutic agents and/or vaccines, which are sufficiently effective especially against resistant strains do not have harmful side effects, and are not difficult or expensive to administer. Therefore, it is an object of this invention to provide a pharmaceutical composition that is effective in inhibiting protozoan infections in humans and animals with minimal side-effects.

More specifically, it is an object of this invention to provide an antiprotozoan composition comprising a pharmaceutical carrier and a spinosyn or spinosyn derivative or salt or prodrug thereof, along with a method for preventing and/or treating a protozoan infection.

Cancers are a leading cause of death in animals and humans. Currently, cancer therapy involves surgery, chemotherapy and/or radiation treatment to eradicate neoplastic cells in a patient. All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue. Radiation therapy can also often elicit serious side effects, while not, for example, being effective against resistant malignant tumors. With respect to chemotherapy, there are a variety of chemotherapeutic agents available for treatment of neoplastic diseases. However, despite the availability of a variety of chemotherapeutic agents, chemotherapy has many drawbacks. Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multi-drug resistance, therefore not all types of cancers and tumors respond to these agents. Clearly, the development of drugs that would specifically target tumor cells would be a breakthrough. Alternatively, drugs that were cytotoxic to tumor cells while exerting mild effects on normal cells would also be desirable. Therefore, it is an object of this invention to provide a pharmaceutical composition that is effective in inhibiting neoplastic cell proliferation in humans and animals with mild or no effects on normal cells.

More specifically, it is an object of this invention to provide an anticancer composition comprising a pharmaceutical carrier and a spinosyn or spinosyn derivative or salt or prodrug thereof, along with a method for treating cancer.

Cancer cells are characterized by a high energy demand required for their extraordinary proliferation and growth rate. Because of the limited supply and high demand of ATP in malignant cells, drugs which may inhibit ATP synthesis can provide a means to control cancer growth. Moreover if the ATP synthesis produced via the oxidative phosphorylation (OXPHOS) pathway is disrupted by an oxphos inhibitor, cancer cells having more vulnerable mitochondria will be disproportionately impacted versus normal cells which have well functioning mitochondria. Cancer cells have a high glycolysis rate even in the presence of oxygen. Under aerobic conditions in tumor cells, a bigger than normal percentage of ATP produced, is derived via glycolysis, in sharp contrast to normal cells, where this value is usually less than 10% and oxidative phosphorylation is the predominant method for ATP generation. Thus, administering to cancer cells a drug that interferes with ATP production in mitochondria, will hypersensitize the cells to glycolytic inhibitors, such as 2-deoxy glucose, as mentioned in US Patent Application 2003/0181393 and U.S. Pat. No. 7,160,865, incorporated herein by reference.

The present invention relates, in general, to compositions and methods aimed at effectively treating tumor cells with a spinosyn composition. It also extends to novel and useful methods and compositions for treating tumor cells with glycolytic inhibitors in combination with a spinosyn.

The present invention is based on the primary discovery that spinosyn, and spinosad in particular, has potent cytotoxic properties against highly proliferating cancer cells. The fact that a substance may be cytotoxic against normal cells, like for example normal hepatocytes, does not mean that it can act also against cancerous cells, which are usually very resistant, very fast proliferating and hard to fight. The present invention is, in part, based on the in vivo pharmacological activity of spinosyns in mice. It is believed that spinosyn acts as an oxidative phosphorylation inhibitor.

Every cell in the body uses carbohydrates, protein, and fat in different proportions for energy. The cell's choice of fuel, its metabolic strategy, will change depending on its state of activation or differentiation. For example, a cell that is rapidly dividing has different energy demands than one that is not dividing. The same is true for cells that are under stress or are infected. As it is stated in U.S. Pat. No. 7,445,794, incorporated herein by reference, the metabolic strategy, widely used by drug resistant cancer cells, is characterized by the ability to burn fat under conditions of stress, including the stress of chemotherapy or radiation. When cells are rapidly dividing, they use glucose at very high rates, but under conditions of stress, cells, if capable, use fat in a greater proportion as a protective strategy. By inhibiting fatty acid metabolism simultaneously with oxphos inhibition, the cell is forced to resume glucose metabolism and it will be very sensitive to glycolysis inhibitors.

The fatty acid metabolism inhibitor used herein can be an oxirane carboxylic acid compound able to inhibit (e.g., prevent, or at least decrease the activity) a reaction within the fatty acid metabolism pathway, such as an enzyme-catalyzed reaction within the pathway. The inhibitor may inhibit the enzyme, e.g., by binding to the enzyme to interfere with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the breakdown of fatty acids into simpler structures, such as $CO_2$, aryl groups, etc.).

Thus, the present invention relates to the use of spinosyn as an oxidative phosphorylation inhibitor, further the invention relates to the use of spinosyns in conjunction with fatty acid metabolism inhibitors. According to one embodiment, the invention relates to the use of this combination to improve the efficacy of cancer treatment by selectively killing tumor cells.

In addition to cancer, an enormous number of human and animal diseases result from virulent and opportunistic viral infections. Viral diseases of a wide array of tissues, including the respiratory tract, CNS, skin, genitourinary tract, eyes, ears, immune system, gastrointestinal tract, and musculoskeletal system, affect a vast number of humans of all ages. Although considerable effort has been invested in the design of effective antiviral therapies, viral infections continue to threaten the lives of millions of people worldwide. In general, attempts to develop antiviral drugs have focused on several stages of viral life cycle. However, a common drawback associated with using many current antiviral drugs is their deleterious side effects, such as toxicity to the host or resistance by certain viral strains. Accordingly, there is a need in the art for antiviral compounds, compositions, and methods that allow for safe and effective treatment of viral disease without the above-mentioned disadvantages.

Thus, according to one embodiment, it is an object of this invention to provide an antiviral composition comprising a pharmaceutical carrier and a spinosyn or spinosyn derivative or salt or prodrug thereof, along with a method for treating or preventing viral infections in animals and humans such as, for example, those caused by Herpes Simplex and Influenza virus with no or minimal side effects to the host.

A viral infection begins when a virion comes into contact with a host cell and attaches or adsorbs to it. The viral (DNA or RNA) then crosses the plasma membrane into the cytoplasm and eventually enters into the nucleus. In the case of retrovirus, the viral RNA is reverse transcribed into DNA. Viral DNA is then integrated into the chromosomal DNA of the infected cell. Integration is mediated by an integration protein, integrase. All integrated proviruses are required for the subsequent transcription process which is acted upon by the host cell transcription factors. The integrated DNA is transcribed by the cell's own machinery into mRNA, or replicated and becomes enclosed in a virion. For retrovirus, the integrated DNA is transcribed into RNA that either acts as mRNA or become enclosed in a virion. This completes the virus life cycle.

Seasonal waves of influenza virus infections have caused over 36,000 deaths per year in the United States alone. Less than 100 years ago, a single strain of H1N1 influenza virus caused a pandemic with more human fatalities than any other single infectious event, war, or famine in world history. (Achievements in Public Health, 1900-1999: Control of Infectious Diseases. *MMWR Morb Mortal Wkly Rep* 1999, 48:621-629). More recently, a highly pathogenic $H_5N_1$ strain of avian influenza has been repeatedly transmitted from birds to humans, resulting in several hundred human deaths. (Technical meeting on highly pathogenic Avian Influenza and Human $H_5N_1$ infection 27-29 Jun. 2007 Rome, A. Croisier, E. Mumford, N. Shindo, C. Steffan, S. martin, K. Fukuda WHO). Fortunately, this has generated few cases of human-to-human transmission and has not yet resulted in a major human pandemic. It is clear that the natural influenza reservoir has the capacity to generate new virus strains that can cross species barriers and produce human infections with increased pathogenicity and, in some cases, increased human-to-human transmission characteristics. These strains present a real and potentially uncontrollable threat to global public health (Nelson, M I, Holmes, E C: The evolution of epidemic influenza. *Nat Rev Genetics,* 8:196-205, 2007).

Influenza viruses are lipid enveloped, with segmented, negative-stranded RNA genomes. They belong to the family of Orthomyxoviridae. The genus Influenzavirus A is comprised of a cluster of strains that replicate as a continuous lineage and can genetically reassort with each other. Therefore, although 15 different HA subtypes and 9 different NA subtypes are recognized among influenza viruses A replicating in birds, separate species designations have not been accorded to these subtypes. All isolates are capable of exchanging RNA segments (reassortment). (ICTVdB Index of Viruses, International Committee on Taxonomy of Viruses). Survivors of influenza virus infection generally mount an immune response with only limited cross-reactivity to other influenza strains, resulting in multiple infections throughout an individual's life time.

Current influenza control efforts have concentrated on the use of vaccines and a small number of anti-influenza drugs. Two main classes of anti-influenza drugs have been developed and are in current use. Inhibitors of the viral ion channel M2 protein, such as amantidine, (Ion channel activity of Influenza A Virus M2 Protein: characterization of the Amantadine Block *J. Virol.* Wang et al. 67 (9): 5585), and rimantidine, have been produced and commercialized, as well as have, inhibitors of the viral surface neuraminidase enzyme, such as oseltamivir (Discovery and development of GS 4104: an orally active influenza neuraminidase inhibitor. Lew W, Chen X, Kim CU. *Med Chem* (6):663-72, 7/2007), which is now in wide use. These drugs are effective as prophylactics in blocking the development of influenza virus symptoms as well as therapeutically treating and reducing the duration of symptoms post-infection. (Gillissen A, Höffken G: Early therapy with the neuraminidase inhibitor oseltamivir maximizes its efficacy in influenza treatment. *Med Microbiol Immunol,* 191:165-168, 2002). However, due to the ability of influenza viruses to rapidly mutate, drug resistance against each of the antiviral classes has appeared quickly. New anti-influenza drugs will be required to keep pace with the ability of influenza viruses to mutate and develop resistance to current drugs.

The viruses belonging to the family Herpesviridae are icosahedral virions with capsid about 105 nm in diameter and 162 capsomeres surrounded by a floppy envelope containing glycoprotein spikes. The genome is composed of linear double-stranded DNA. There are 3 known subfamilies: Alphaherpesvirinae, consisting of human herpex simplex viruses types 1 and 2, bovine mamillitis virus, SA8 virus and monkey B virus, pseudorabies virus, equine herpesvirus, and varicella-zoster virus (VZV); Betaherpesvirinae, composed of species of cytomegaloviruses (CMV) and Gammaherpesvirinae, composed of genera familiarly called Epstein-Barr virus, baboon herpesvirus, chimpanzee herpesvirus, Marek's disease virus of chickens, turkey herpesvirus, herpesvirus saimiri, and herpesvirus ateles. Ocular herpes is a recurrent viral infection that is caused by the herpes simplex virus and is the most common infectious cause of corneal blindness.

Herpes simplex virus 1 and 2 (HSV-1 and HSV-2) are two species of the genus Simplexvirus belonging to the virus family, Herpesviridae, which cause infections in humans. As with other herpesviridae, herpes simplex virus may produce life-long infections. They are also called Human Herpes Virus 1 and 2 (HHV-1 and HHV-2) and are neurotropic and neuro-invasive viruses. HSV-1 is generally associated with infections in and around the mouth and with other infections above the waist. Typically, infection is characterized by a cluster of small blisters or watery vesicles on the skin or on mucous membranes. Clusters most frequently occur on the lips and face and occasionally on the trunk and hands. HSV-1 may also infect the eye, causing corneal ulcers and visual impairment. Antiviral treatment very early in the course of the disease may decrease the length of recurrences. However, there is no satisfactory treatment for HSV-1 infection; as long as the virus remains in some cells in a latent form, antiviral drugs cannot rid the body of infection.

The sexually transmitted disease genital herpes is associated primarily with HSV-2. The virus is highly contagious and may be transmitted by individuals who are lifelong carriers but who remain asymptomatic. A variety of treatments have been used for genital herpes, but none is entirely satisfactory. Methods of treatment include the use of ointments and creams, topical anesthetics, and antiseptic solutions. Antiviral agents such as acyclovir may be effective in diminishing the duration of symptoms and the period of time during which the virus may be recovered from the lesions.

Entry of HSV into the host cell involves interactions of several glycoproteins on the surface of the enveloped virus, with receptors on the surface of the host cell. The envelope covering the virus particle, when bound to specific receptors on the cell surface, will fuse with the host cell membrane and create an opening, or pore, through which the virus enters the host cell. The sequential stages of HSV entry are analogous to those of other enveloped viruses.

In the past two decades, the emergence of human immunodeficiency virus type 1 (HIV-1), Dengue, and West Nile virus as important human pathogens has led to a resurgence of scientific interest in retroviruses and other viruses as well. HIV and other viral infections are a leading cause of death. HIV is a disease in which a virus is replicated in the body which attacks the body's immune system. The HIV virus is not easily destroyed nor is there a good mechanism for keeping the host cells from replicating the virus.

Rhinoviruses are non-envelope viruses, that is, they lack a glycolipid/glycoprotein envelope external to the capsid. Rhinovirus is a genus of the Picornaviridae family of viruses. Rhinoviruses are the most common viral infective agents in humans, and a causative agent of the common cold.

According to one embodiment, it is an object of this invention to provide a pharmaceutical composition that is effective in inhibiting viral infections in humans and animals with minimal side-effects.

More specifically, it is an object of this invention to provide an antivirus composition comprising a pharmaceutical carrier and a spinosyn or spinosyn derivative or salt or prodrug thereof, along with a method for preventing and/or treating a virus infection.

Spinosyns have been commercially developed by Dow AgroSciences and have heretofore been used most commonly as pesticides/insecticides and to treat ectoparasites. This group of macrolides, originally discovered by Eli Lilly scientists in the search for new pharmaceuticals, has never been proposed for use as an antiprotozoan, antiviral and/or as an antineoplastic agent. Further, the prior work on these compounds (safety evaluation of spinosad insecticide K. E. Stebbins, D. M. Bond, M. N. Novilla and M. J. Reasor, "Spinosad insecticide: Subchronic and chronic Toxicity and Lack of Carcinogenicity in CD-1 Mice" *Toxicological Sciences* 65:276-287, 2002) states that Spinosad has no known pharmacological activity in mice (with reference to an unpublished report to Horii, D.) Therefore, the present results are quite unexpected.

Other uses for spinosyns have been reported. As described in Published U.S. Patent Application 2007/0167379, incorporated herein by reference, spinosyns may be used in humans and mammals to promote or accelerate wound healing in both normal and healing impaired cases. According to this patent, Spinosad, stimulates the neurogenic activation of healing, and subsequent inflammatory activity involved in cell growth and proliferation (it stimulates epithelial cell proliferation and basal keratinocytes for the purpose of would healing). As it is also stated in U.S. Pat. No. 6,664,237, single-dose spinosyn oral veterinary formulations may be used for controlling an ectoparasite infestation on a companion animal for a prolonged time. The advantages of these oral systemic treatments is the killing of the ectoparasites (fleas) by ingestion of animals' blood that contains spinosyn in contrast to contact killing by topical applications. In addition, spinosad cream rinse 0.9% has proven to be very effective for head lice treatment in children (Stough D., *Pediatrics.* 2009; 124:e389-e395).

It was unexpectedly discovered that spinosyns and most specifically, spinosad, do have pharmacological activity in mice, they are effective antiprotozoan, antiviral and anticancer agents, and can be used as pharmaceuticals to prevent, treat and/or inhibit human and animal infections caused by protozoans, viruses and/or neoplastic cell proliferation. Pharmacological activity in mice has not heretofore been established. Spinosad's bioavailability and specific pharmacological activity was apparent and consistent when using DMSO as a carrier. It is believed that different spinosad compositions and routes of administration result in differing activities for different diseases. For example, an oral spinosad in propylene glycol is not preferred when treating *Plasmodium* parasites in *Plasmodium*-infected mice. Likewise, a spinosad in olive oil composition administered intraperitoneally is not preferred when treating *Leishmania* parasites in *Leishmania*-infected mice. According to one embodiment of the present invention, spinosyns, more specifically spinosad, can be used to prevent, treat or inhibit infections, for example, malaria caused by the protozoan parasites *Plasmodium* spp, and Leishmaniasis caused by the protozoan parasites *Leishmania* spp. According to another embodiment of the present invention, spinosyns, more specifically spinosad, can be used to prevent, treat or inhibit viral infections caused, for example, by Herpes Simplex 1, Herpes Simplex 2 and other influenza visuses. According to yet another embodiment of the present invention, spinosyns, more specifically spinosad, can be used to prevent, treat or inhibit neoplastic cell proliferation.

According to one embodiment, the present invention relates to antiprotozoan and/or antiviral and/or anticancer pharmaceutical compositions, including veterinary compositions, comprising at least one spinosyn or derivative or salt or prodrug thereof. Compositions according to this embodiment of the invention contain at least one spinosyn in an amount effective to inhibit the protozoan, the virus or the neoplastic cell proliferation which may not be harmful to a host, for example, a human or an animal.

In one embodiment, the present invention relates to a method of treatment, including prophylaxis, of cancer or of an infection caused by a protozoan, e.g. malaria or leishmaniasis or by a virus e.g. Herpesvirus 1 & 2 or Influenza virus, the method comprising administering a spinosyn composition according to the invention to the host in need thereof, i.e., the human or animal.

In another embodiment, the present invention relates to a method of limiting the spread of a parasitic disease when hosts are treated with a spinosyn composition. Vectors transmitting the disease, for example, anopheles mosquitoes, are sensitive to spinosyn when they ingest it and they will die upon biting the spinosyn treated host, before being able to transmit the parasites to other healthy hosts.

The present invention also includes methods and compositions useful in facilitating spinosyn delivery for combating cancer or for treating or alleviating a viral infection, for example, an infection caused by Herpes Simplex virus 1 and 2 or Influenza A (e.g. H1N1 strain) or a disease caused by a protozoan, i.e., malaria or leishmaniasis, in the human or animal body.

In a particular embodiment, the present invention relates to a pharmaceutical composition comprising at least one spinosyn and a suitable carrier.

The term "preventing", when used in relation to a condition, such as cancer, or a virus or a protozoan disease, or other medical disease or condition, is well understood in the art, and as used herein refers to the administration of a composition which reduces the frequency of, or delays the onset of symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population.

As used herein, "chemotherapy", in its most general sense, is the treatment of a disease by chemicals, especially by killing micro-organisms or neoplastic cells.

As used herein "neoplastic cells" are cells caracterized by an abnormal proliferation rate, usually but not always resulting in the development of a lump or tumor. Neoplastic cells may be benign, premalignant or malignant. The term is used herein interchangeably with the term "cancer" or "cancerous" cells.

As used herein, the term "cancer" includes all types of neoplasm whether in the form of solid or non-solid tumors, from all origins, including both malignant and premalignant conditions as well as their metastasis, and hematological malignancies. The former includes cancers such as breast, colon, and ovarian cancers. The latter include hematopoietic malignancies including leukemias, lymphomas and myelomas. Hematological malignancies, such as leukemias and lymphomas, are conditions characterized by abnormal growth and maturation of hematopoietic cells.

Leukemias are generally neoplastic disorders of hematopoietic stem cells, and include adult and pediatric acute myeloid leukemias (AML), chronic myeloid leukemia (CML), acute lymphocytic leukemia (ALL), chronic lymphocytic leukemia (CLL), hairy cell leukemia and secondary leukemia. Myeloid leukemias are characterized by infiltration of the blood, bone marrow, and other tissues by neoplastic cells of the hematopoietic system. CLL is characterized by the accumulation of mature-appearing lymphocytes in the peripheral blood and is associated with infiltration of bone marrow, the spleen and lymph nodes. Specific leukemias include acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas are generally neoplastic transformations of cells that reside primarily in lymphoid tissue. Among lymphomas, there are two major distinct groups: non-Hodgkin's lymphoma (NHL) and Hodgkin's disease. Lymphomas are tumors of the immune system and generally are present as both T cell- and as B cell-associated disease. Bone marrow, lymph nodes, spleen and circulating cells are all typically involved.

Other hematological malignancies include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

Hematological malignancies are generally serious disorders, resulting in a variety of symptoms, including bone marrow failure and organ failure. Treatment for many hematological malignancies, including leukemias and lymphomas, remains difficult, and existing therapies are not universally effective. Accordingly, there remains a need in the art for improved methods for treating hematological malignancies such as B cell leukemias and lymphomas and multiple myelomas. Embodiments of the present invention can fulfill these and other needs in the field.

Other cancers treatable according to one or more embodiments of the present invention also represent similar difficulties insofar as effective treatment is concerned. Such cancers include those characterized by solid tumors. Examples of other cancers of concern are skin cancers, including melanomas, basal cell carcinomas, and squamous cell carcinomas. Epithelial carcinomas of the head and neck are also encompassed by the present invention. These cancers typically arise from mucosal surfaces of the head and neck and include salivary gland tumors. The present invention also encompasses cancers of the lung. Lung cancers include squamous or epidermoid carcinoma, small cell carcinoma, adenocarcinoma, and large cell carcinoma. Breast cancer is also included, both invasive breast cancer and non-invasive breast cancer, e.g., ductal carcinoma in situ and lobular neoplasia. The present invention also encompasses gastrointestinal tract cancers. Gastrointestinal tract cancers include esophageal cancers, gastric adenocarcinoma, primary gastric lymphoma, colorectal cancer, small bowel tumors and cancers of the anus. Pancreatic cancer and cancers that affect the liver are also of concern, including hepatocellular cancer, gynecologic malignancies including ovarian cancer, carcinoma of the fallopian tube, uterine cancer, and cervical cancer, sarcomas of the bone and soft tissue, bone sarcomas include osteosarcoma, chondrosarcoma, and Ewing's sarcoma, malignant tumors of the thyroid, including papillary, follicular, and anaplastic carcinomas.

The term "virus" is art recognized and refers to non-cellular biological entities lacking metabolic machinery of their own which reproduce by using that of a host cell. Viruses comprise a molecule of nucleic acid (DNA or RNA) and can be envelope or non-envelope viruses.

As used herein, "effective to inhibit", "inhibit the growth" or "inhibiting effective amount" or "pharmaceutically effective amount" refers to an amount of spinosyn capable of destruction, reduction, suppresion, inhibition, or prevention of the growth or proliferation of a protozoan, a neoplastic cell or a virus within the host at a reasonable benefit/risk ratio applicable to any medical treatment. Further as used herein, the terms "effective," "effective amount," "effective in the control of," and "effective for control" or "control" are all used interchangeably and all refer to the ability of the composition/active to destroy, suppress, inhibit or prevent the growth or proliferation of the protozoan, the neoplastic cell or the virus compared to a non-active containing composition. An "inhibiting effective amount" is the minimal amount of active agent (e.g., a spinosyn and most preferably spinosad) which is necessary to inhibit protozoan, cancer cell or virus proliferation, and in the case of a pharmaceutical composition, one that provides therapeutic benefit to a human or animal. The term "therapeutically effective amount" as used herein refers to the amount necessary to elicit the desired biological response. As will be appreciated by those of ordinary skill in this art, the effective amount of a drug may vary depending on such factors as the desired biological endpoint, the drug to be delivered, the composition of any additional active or inactive ingredient, the target tissue, and the route of administration.

The term "inhibition of proliferation" in relation to cancer cells, in the context of the present invention, refers to a decrease in at least one of the following: number of cells (due to cell death which may be necrotic, apoptotic or any other type of cell death or combinations thereof) as compared to control; decrease in growth rates of cells, i.e., the total number of cells may increase but at a lower level or at a lower rate than the increase in control; decrease in the invasiveness of cells as compared to control even if their total number has not changed; progression from a less differentiated cell type to a more differentiated cell type; a deceleration in the neoplastic transformation; or alternatively the slowing of the progression of the cancer cells from one stage to the next.

The terms "treat," "treated," or "treating," when used with respect to administration to a host, refer to a therapeutic regimen that prevents the infection, decreases the amount or effect of an infectious agent in a host who has become infected in order to fight the infection, e.g., reduces or eliminates the infection or prevents it from becoming worse, or which prevents a further increase in amount or activity of an infectious agent or decreases or eliminate the neoplastic cells proliferation rate. The term "treating", as used herein, unless otherwise indicated, means reversing, alleviating, inhibiting the progress of, or inhibiting the development of a disorder or condition or one or more symptoms of such disorder or condition caused by protozoan infection, by viral infection or cancer. The term "treatment", as used herein, refers to the act of treating, as "treating" is defined above.

A "host" as used in the present invention refers to humans and animals. The term animal includes all animals. Examples of animals are non-ruminants and ruminants. Ruminant animals include, for example, animals such as sheep, goat, and cattle, e.g., cows including beef cattle and dairy cows. According to one embodiment, the animal is a non-ruminant animal. Non-ruminant animals include household pets, e.g. dogs or cats as well as mono-gastric animals, e.g., pig or swine (including, but not limited to, piglets, growing pigs, and sows); poultry including turkeys, ducks and chickens (including but not limited to broiler chicks, layers); fish (including but not limited to salmon, trout, tilapia, catfish and carp); and crustaceans (including but not limited to shrimp and prawn).

As used herein, the term "active agent" or "therapeutic agent" means any compound or composition, which, upon being administered to a host, is capable of being a benefit in alleviating or treating a disease in the host or reducing the severity of the symptoms of a disease.

As used herein, the term "combating a cancer" or "treating a cancer" in a host means, for example, any one or more of the following: to increase survival of a host, to decrease or arrest tumor size in a host, or to increase the time period of remission of cancer regrowth, relative to an otherwise identical host which was not administered a spinosyn or spinosyn composition of the invention.

As used herein, "alleviating a virus or protozoan disease" means reducing the severity of a symptom of the disease caused by a virus or protozoan.

As used herein, the term "facilitating delivery" or "to facilitate delivery" of a therapeutic agent to a host cell, means enhancing the uptake of a therapeutic agent in a cell to a level higher than the level of uptake of the therapeutic agent in an otherwise identical host cell which is not administered a compound or composition of the invention. The uptake of a therapeutic agent can be enhanced, by way of example and not by limitation, by any one or more of the following means: by bypassing the requirement for a cellular active transport mechanism for uptake of the therapeutic agent into a cell; by providing the therapeutic agent (i.e. a drug) intracellularly in an activated form, thereby bypassing the requirement for intracellular activation of the therapeutic agent by an enzyme such as an intracellular kinase; by overcoming a physiological barrier to uptake of the therapeutic agent in a desired cell, such as low solubility, poor absorption from the stomach or small intestine, or impermeability to the blood-brain barrier, and by enabling delivery of the therapeutic agent to sites not normally accessible thereto (i.e. CNS and lymphoid tissues).

As used herein, the term "anticancer agent" or "antineoplastic agent" means a therapeutic agent which is capable of exhibiting efficacy at combating an uncontrolled proliferation in a host cell, or any compound which is capable of being converted intracellularly to a compound which is capable of exhibiting efficacy at combating an uncontrolled cell proliferation in a host.

The terms "parasite", "endoparasite" or "parasitic", "endoparasitic" as used herein, refer to an organism that lives inside another organism to the detriment of the host organism.

The term "protozoan" refers to any singled-celled eukaryotic possessing a well-defined nucleus) organism that can infect humans and animals.

The term "Apicomplexa," previously called Sporozoa, refers to the phylum of protozoans, which are parasitic in both vertebrates and invertebrates. This phylum of protozoans have vesicular nucleus; lack flagella or cilia, except in the flagellated microgamete stage; usually a sexual phase in the life cycle with male and female gametes. Schizogony and sporogony are features of the life cycle, and cysts are often present at some stage in species with one-host cycles. Typical species include *Plasmodium falciparum, Toxoplasma gondii, Cryptosporidium* and *Eimeria* species.

The term "Euglenozoa" refers to the phylum of protozoans with discoidal mitochondrial cristae; large nuclear endosome; sheets of cortical microtubules under the pellicle; paraflagellar rods; cytochrome c and 5S rRNA homologies known for euglenoids and kinetoplastideans; euglenoid plastids enclosed in 3 membrane and having no stored starch and no cellulosic wall; kinetoplastideans with large DNA body in mitochondrion. Euglenozoa belong to the infrakingdom Excavata.

The term "Percolozoa" refers to the phylum of colourless protozoa, including many that can transform between amoeboid, flagellate, and encysted stages, belonging to the infrakingdom Excavata. There are a few marine and parasitic forms, including the species *Naegleria fowleri*, which can become pathogenic in humans and is often fatal. The group is closely related to the Euglenozoa.

The term "metamonada" refers to the phylum of flagellate protozoa belonging to the infrakingdom Excavata.

The spinosyn of the invention may be used (i) in therapy, i.e., for the treatment of a protozoan disease, for example, malaria and/or leishmaniasis or a viral infection, for example, a Herpes infection, or cancer, and/or (ii) for prophylaxis, i.e., treatment to prevent the onset of a viral or protozoan infection or abnormal cell proliferation ("primary" prophylaxis), and/or the recurrence of symptoms in an existing infection that has been brought under control ("secondary" prophylaxis, maintenance therapy).

The spinosyn compositions of the invention may be used (a) in veterinary medicine, which is the application of medical, diagnostic, and therapeutic principles to companion, domestic, exotic, wildlife, and production animals; and/or (b) in human medicine.

Spinosyns are known fermentation products derived from the naturally occurring bacteria *Saccharopolyspora spinosa*. The family of compounds derived from this bacteria are generally known as spinosyns and have been referred to as factors or components A, B, C, D, E, F, G, H, I, J, K, L, M, N, O, P, Q, R, S, T, U, V, W, Y, and the like, as described in U.S. Pat. Nos. 5,362,634, and 6,821,526 and published applications WO 93/09126 and WO 94/20518, which are each incorporated herein by reference in their entirety. The spinosyn compounds consist of a 5,6,5-tricylic ring system, fused to a 12-membered macrocyclic lactone, a neutral sugar (rhamnose), and an amino sugar (forosamine) (see Kirst et al. "Unique Fermentation-derived Tetracyclic macrolides, *Tetrahedon Letters*, A83543A-D, 32:4839-4842, (1991)). As used herein, the term "spinosyn" refers to a class of compounds which are based upon the fermentation products from the naturally occurring bacteria, *Saccharopolyspora spinosa* and *Saccharopolyspora pogona* (species and subspecies *and* mutants thereof) or a biologically modified form of these bacteria or combinations thereof. Natural spinosyn compounds may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyn compounds are also disclosed in U.S. Pat. Nos. 5,496,931, 5,670,364, 5,591,606, 5,571,901, 5,202,242, 5,767,253, 5,840,861, 5,670,486 and 5,631,155. As used herein, the term "spinosyn" is intended to include natural factors and semi-synthetic derivatives of the naturally produced factors. A large number of chemical modifications to these spinosyn compounds have been made, sometimes referred to as spinosoids and are disclosed in U.S. Pat. No. 6,001,981, hereby incorporated by reference. The term "spinosyn" also includes the novel biologically-active compounds as described in published U.S. Patent Application No. 2006/0040877 produced by methods of using the hybrid polyketide synthase DNA to change the products made by spinosyn producing strains. Finally, the term "spinosyn" includes new spinosyn derivatives produced using the cloned *Saccharopolyspora spinosa* DNA as described in U.S. Pat. No. 7,015,001. Different patterns of control may be provided by biosynthetic intermediates of the spinosyns or by their derivatives produced in vivo, or by derivatives resulting from their chemical modification in vitro. Such biosynthetic (derived biologically) or synthetic (derived chemically) or semi-synthetic (derived biologically and then modified chemically) intermediates of the spinosyns are considered to belong to the class of "spinosyns" as described herein for use in the present invention.

Macrolide insecticides related to the spinosyns have been isolated from *Saccharopolyspora* sp. LW107129 (NRRL 30141 and mutants thereof). These compounds are disclosed in U.S. Pat. No. 6,800,614, herein incorporated by reference. These butenyl-spinosyn compounds—also called pogonins from the *Saccharopolyspora pogona* sp. —differ from the known spinosyns with reference to the group attached at C-21 of the macrolide (i.e., 1-butenyl, 1-propenyl etc) and optionally have new groups linked with the oxygen at C-17 of the macrolide ("Butenyl-spinosyns, a natural example of genetic engineering of antibiotic biosynthetic genes". *Journal of Industrial Microbiology & Biotechnology*, Vol. 33, no 2, pp. 94-104, February 2006). A group of these spinosyns have a new 14-carbon macrolide ring system. Natural and semi-synthetic derivatives of the 21-butenyl and related spinosyns are also disclosed in U.S. Pat. No. 6,919,464, herein incorporated by reference. These compounds, are prepared directly or indirectly by modifying the compounds naturally produced by LW107129 or mutants thereof, that contain inactivated O-methyltransferase genes. They are structurally similar to the "classical" spinosyns, therefore the name spinosyn has been kept for these compounds as well. The three main structural elements in these molecules in which variations were seen are: (i) the macrocyclic ring system, (ii) the sugar attached to C-17 and (iii) the side chain attached to C-21, therefore the new naming system (nomenclature) is a composite of these three elements and as an example, we refer to spinosyn α1, spinosyn β1, spinosyn δ1, spinosyn α4, spinosyn β3, spinosyn β4, spinosyn α1a, spinosyn β1a, etc. ("Discovery of the butenyl-spinosyn insecticides: Novel macrolides from the new bacterial strain *Saccharopolyspora pogona*" P. Lewer at al, *Dow Agrosciences, Bioorganic & Medicinal Chemistry* 17 4185-4196 (2009)). Accordingly, the term spinosyn as used herein, is intended to include all of the above natural factors and semi-synthetic and synthetic derivatives of the naturally produced factors or combinations thereof.

Spinosyns and derivatives thereof can also exist in the form of pharmaceutically-acceptable salts and all crystalline forms of such salts. The term "pharmaceutically-acceptable salt" includes those salts that are, within the scope of sound medical judgment, suitable for use in contact with the tissues of humans and animals without undue toxicity, irritation, and allergic response, and are commensurate with a reasonable benefit/risk ratio. Pharmaceutically-acceptable salts are well known in the art. The salts may be prepared in-situ during the final isolation and purification of the compounds of the invention or separately by reacting a free base function with a suitable acid. By way of non-limiting example, spinosyns can form salts with hydrochloric, hydrobromic, sulfuric, phosphoric, acetic, benzoic, citric, malonic, salicylic, fumaric, oxalic, succinic, tartaric, lactic, gluconic, ascorbic, maleic, aspartic, cholic, glutamic, phthalic, picric, cinnamic, sorbic, benzenesulfonic, methanesulfonic, ethanesulfonic, hydroxymethanesulfonic, and hydroxyethanesulfonic acids. Additionally, by way of non-limiting example, pharmaceutically acceptable basic addition salts include cations based on alkali metals or alkaline earth metals such as lithium, sodium, potassium, calcium, magnesium, and aluminum salts, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term spinosyn also includes all isomers of the compounds, including constitutional (structural) isomers and stereoisomers (spatial). The stereoisomers include diastereomers and enantiomers. The diastereomers include cis-trans isomers, anomers, conformers and rotamers. The term spinosyn also includes racemic mixtures, optically active mixtures and combinations thereof.

The spinosyns of the present invention can be also in the form of a hydrate, which means that the compound further includes a stoichiometric or non-stoichiometric amount of water bound by non-covalent intermolecular forces, in the form of a solvate or a conjugate and salts thereof. "Solvate" means a physical association of a compound of the invention with one or more solvent molecules. This physical association involves varying degrees of ionic and covalent bonding, including hydrogen bonding.

In addition the term "spinosyn" as used herein, refers also to spinosyns produced by any fungal strains capable of producing spinosyn, i.e., fungal strains belonging to the genus *Aspergillus*, as mentioned in Patent Application No. WO/2009/054003, herein incorporated by reference.

The terms "derivative" or "structural analog" or "analog" or "homolog" all refer to a compound that is derived from a similar compound If one or more atoms, functional groups, or substructures have been replaced with different atoms, groups, or substructures. The term also refers to compounds that at least theoretically can be formed from the precursor compound.

Spinosad is an insecticide produced by Dow AgroSciences LLC (Indianapolis, Ind.) that is comprised of approximately 85% spinosyn A and approximately 15% spinosyn D. Spinosad is an active ingredient in several insecticide formulations available commercially from Dow AgroSciences LLC, including, for example, those marketed under the trade names TRACER®, SUCCESS®, SPINTOR®, LASER®, and ENTRUST®. The TRACER® product, for example, is comprised of about 44% to about 48% Spinosad (w/v), while ENTRUST® is a white to off-white solid powder containing about 80% Spinosad.

Spinosad, is also commercially available from the company Sigma-Aldrich for R&D purposes, as an analytical standard, at a purity of approximately 98% and is comprised mainly of approximately 70% spinosyn A and 30% spinosyn D.

Spinetoram is a semi-synthetic spinosyn, available commercially from Dow AgroSciences LLC in several insecticide formulations, including, for example, those marketed under the trade names DELEGATE® and RADIANT®. Spinetoram is the common name for a mixture of 50-90% (2R,3αR, 5αR,5βS,9S,13S,14R,16αS,16βR)-2-(6-deoxy-3-O-ethyl-2, 4-di-O-methyl-α-L-mannopyranosyloxy)-13-[(2R,5S,6R)-5-(dimethylamino)tetrahydro-6-methylpyran-2-yloxy]-9-ethyl-2,3,3α,4,5,5α,5β,6,9,10,11,12,13,14,16α,6β-hexadecahydro-14-methyl-1H-as-indaceno[3,2-d] oxacyclodo decine-7,15-dione, and 50-10% (2R,3αR,5αS, 5βS,9S,13S,14R,16αS,16βS)-2-(6-deoxy-3-O-ethyl-2,4-di-O-methyl-α-L-mannopyrano syloxy)-13-[(2R,5S,6R)-5-(dimethylamino)tetrahydro-6-methylpyran-2-yloxy]-9-ethyl-2,3,3α,5α,5β,6,9,10,11,12,13,14,16α,16β-tetradecahydro-4,14-dimethyl-1H-as-indaceno[3,2-d] oxacyclododecine-7,15-dione. Synthesis of the components of spinetoram is described in U.S. Pat. No. 6,001,981.

Spinosad, a safe and environmentally-friendly pesticide, derived from the fermentation juices of a soil bacterium called *Saccharopolyspora spinosa*, has been granted organic status by the USDA National Organic Program (NOP) in 2003 and Dow Agrosciences LLC, main producer of spinosyns, was presented by the U.S Environmental Protection Agency, with the Presidential Green Chemistry Challenge Award in the past for spinosad and in 2008 for spinetoram as well, as both products adhere to the principles of green chemistry. To chemists, spinosad is a complex molecule known as a "glycosylated macrolactone." It acts against pests as a stomach and contact poison with a unique and not well understood mode of action. The present invention, has for the first time linked spinosyn and more specifically spinosad with antiprotozoan activity against, for example, *Plasmodium* spp and *Leishmania* spp., with antiviral activity against, for example, HSV-1 and HSV-2 and Influenza A (H1N1 strain) viruses and with inhibition of neoplastic cell proliferation.

While not wishing to be bound by theory regarding spinosyns' mechanism of action, it is believed that spinosyns present in the antiprotozoan, antiviral and/or anticancer composition of this invention, function by creating an environment where protozoa, viruses and cancer cells can not survive or proliferate, thereby preventing their growth in this environment.

Moreover, the present invention has for the first time suggested a new mode of action by spinosyns, which is based on cell function. Effects at the cellular level cause chain reactions to follow in an organism. Although various suggestions had been made in the past, all describe the consequences of the initial mode of action, i.e., the results of the chain reactions rather than the mechanism itself. For example, although it is known that spinosad is neurotoxic to insects as many other insecticides are, cross-resistance has not been observed, suggesting spinosad's distinct and unique mode of action that has not been previously identified. Among these previous suggestions are that (i) spinosyn acts via nicotinic acetylcholine receptors nAChRs in insects causing involuntary muscle contractions and later a neuromuscular block ("Studies on the mode of Action of Spinosad: The Internal Effective Concentration Dependence of Neural Excitation" V. Salgado et al., *Pesticide Biochemistry and Physiology* 60, 103-110 (1998)) (ii) it inhibits insects digestive enzymes (i.e., glucoamylase) resulting in the inability for them to hydrolyze polysaccharides and by changing the activities of alkaline and acidic phosphatases, without though producing any pattern, capable to link it with a specific mode of action ("Biochemical Abnormalities produced by Spinosad in *Tribolium castaneum* Adult Beetles": R. Hussain et al., *Pakistan International Journal of Agriculture & Biology* ISSN Print: 1560-8530; 08-267/DMK/2009/11-3-241-244), (iii) it has inhibitory effects on AChE and $Na^{+-}$ATPase $K^{+-}$ATPase enzymes of insects resulting in neurotoxicity ("Toxic Effect and Biochemical Study of Chlorfluazuron, Oxymatrine and spinosad on Honey Bees" E. I. Rabea et al., *Archives of Environmental Contamination and Toxicology* Springer New York, 0090-4341 (2009)).

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide ($NADH+H^+$) from oxidized nicotinamide adenine dinucleotide ($NAD^+$), and oxidative phosphorylation, during which $NADH+H^+$ is oxidized back to $NAD^+$. (The citric acid cycle also reduces flavin adenine dinucleotide, or FAD, to $FADH_2$; $FADH_2$ also participates in oxidative phosphorylation.)

The electrons released by oxidation of $NADH+H^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP. When cells in an organism are temporarily deprived of oxygen, anaerobic respiration is utilized until oxygen again becomes available or the cell dies. The pyruvate generated during glycolysis is converted to lactate during anaerobic respiration.

The present invention first recognizes that spinosyns and spinosad, in particular, is an oxidative phosphorylation inhibitor, i.e., it inhibits the ATP formation through the oxidative phosphorylation pathway within the cells. The degree of inhibition of oxidative phosphorylation depends on the amount of spinosyn used, the time during which a cell is exposed to this amount of spinosyn, the kind of the cell, i.e., the ability of the cell to respond properly and be adjusted to a mitochondrial respiration disruption, the specific spinosyn and carrier used and the cell environment conditions (e.g. temperature). Thus, a very small amount of spinosyn, and spinosad in particular, being in contact with a normal cell for a short time, will not affect its oxidative phosphorylation function considerably and irreversibly, while higher amounts of spinosad and prolonged exposure would more severely affect oxidative phosphorylation, resulting in irreversible effects and consequent cell death. The term "inhibition of oxidative phosphorylation" as used in the present invention, includes partial, temporary and complete inhibition. As it is shown in Example No. 16, below, a 20 μg/ml spinosad in DMSO, decreases the oxygen consumption of H460 cells by 50% within 3 hours, compared to the control and untreated cells. At this timepoint and experimental conditions, reduction of oxygen consumption due to cytotoxicity has been excluded following confirmation through the experimental data presented in the same example.

Example 17, was carried out, in order to confirm that the spinosad acts directly on the mitochondria and that the OXPHOS inhibition is a direct effect rather than a consequence of another effect within the cell's cytosol. In example 17, isolated mitochondria of H460 cells were directly affected by spinosad, when exposed to various spinosad concentrations, and OXPHOS through at least Complex II is reduced by spinosad following ADP stimulation. Complex II (succinate dehydrogenase) is not a proton pump. It serves to funnel additional electrons into the quinone pool (Q) by removing electrons from succinate and transferring them (via FAD) to Q. Disrupting activity of Complex II within the electron transport chain, results in decreased State III respiration and inhibition of ATP formation. The substrate used in the assay of example 17 was succinate that allows electron transport through Complex II. Effects on Complex I of the electron transport chain are also expected and can be confirmed by using glutamate and malate as substrates.

In the case of *Plasmodium*, which produces its ATP exclusively through the glycolytic pathway, without wishing to be bound by, it is believed that spinosad exhibits a double action against it: (a) spinosad diffuses through the *Plasmodium* external and then the digestive vacuole membranes and it gets protonated within the parasite's highly acidic digestive food vacuole; by being "trapped" inside the food vacuole, it interferes with essential processes, resulting in *Plasmodium* death, and (b) at the same time spinosad is diffused within *Plasmodium* mitochondrion, where, acting as an OXPHOS inhibitor, it disrupts the parasite mitochondrial functions. The most important mitochondrial function connected with the oxidative phosphorylation in *Plasmodium*, is pyrimidine biosynthesis. It is reported that *Plasmodium* mitochondrion contain both conserved and unusual features, including an active electron transport chain and many of the necessary enzymes for coenzyme Q and iron-sulphur cluster biosynthesis. It also plays an important role in pyrimidine metabolism ("Metabolic maps and functions of the *Plasmodium* mitochondrion", Van Dooren G G at al., *FEMS Microbiol Rev.* 30(4):596-630, 7/2006). The identification of mitochondrial Complex II subunits in *plasmodium* as well as the Microaerophilic respiratory metabolism of *Plasmodium*, have been also studied ("Identification of Mitochondrial Complex II subunits SDH3 and SDH4 and ATP synthase subunits a and b in *Plasmodium* spp", Mogi T., Kita K., *Mitochondrion*, 9(6):443-53, 11/2009) & ("Microaerophilic respiratory metabolism of

*Plasmodium Falciparum* mitochondrion as a drug target," Torrentino-Madamet M. at al., *Curr Mol Med.* 2010 Feb. 1; 10(1):29-46).

In one embodiment of the invention, spinosyns and spinosyn compositions and methods of the invention and combination therapies provided herein, can be used to treat or improve a wide variety of diseases or disorders caused by, or associated with, mitochondrial function and dysfunction, as well as conditions related to oxidative phosphorylation inhibition, including but not limited to autoimmune diseases, for example, rheumatoid arthritis, metabolic disorders, for example, obesity and others like cardiac ischemia and reperfusion.

Purines and pyrimidines are two of the building blocks of nucleic acids. Modulating the pyrimidine metabolism pharmacologically has therapeutical uses. Pyrimidine synthesis inhibitors are used to treat active moderate to severe rheumatoid arthritis and psoriatic arthritis by inhibiting dihydroorotate dehydrogenase, an enzyme involved in de novo pyrimidine synthesis. Spinosad will inhibit pyrimidine biosynthesis by inhibiting Complex II in the oxidative phosphorylation electron transport chain (succinate-ubiquinone reductase).

The inhibition of oxidative phosphorylation causes the organism to shut down metabolically and enter a hibernation-like state. Manipulating this metabolic mechanism for clinical benefit potentially could revolutionize treatment for a host, of human ills related to ischemia or damage to living tissue from lack of oxygen. Clinical use of induced metabolic hibernation could include treating severe blood-loss injury, hypothermia, malignant fever, cardiac arrest and stroke. Using oxygen deprivation to depress metabolic activity also might extend the amount of time that organs and tissues could be preserved outside the body prior to transplantation ("*Buying time through Hibernation on Demand*" Dr. Mark Roth, University of Washington School of Medicine, Fred Hutchinson Cancer Research Center-Media Toolkit). Mitochondria are increasingly recognized as lynchpins in the evolution of cardiac injury during ischemia and reperfusion. Modulation of mitochondrial respiration during and immediately following an episode of ischemia can attenuate the extent of myocardial injury. The blockade of electron transport and the partial uncoupling of respiration are two mechanisms whereby manipulation of mitochondrial metabolism during ischemia decreases cardiac injury. Although protection by inhibition of electron transport or uncoupling of respiration initially appears to be counterintuitive, the continuation of mitochondrial oxidative phosphorylation in the pathological milieu of ischemia generates reactive oxygen species, mitochondrial calcium overload, and the release of cytochrome c. The initial target of these deleterious mitochondrial-driven processes is the mitochondria themselves. Consequences to the cardiomyocyte, in turn, include oxidative damage, the onset of mitochondrial permeability transition, and activation of apoptotic cascades, all favoring cardiomyocyte death. Ischemia-induced mitochondrial damage carried forward into reperfusion further amplifies these mechanisms of mitochondrial-driven myocyte injury. Interruption of mitochondrial respiration during early reperfusion by pharmacologic blockade of electron transport or even recurrent hypoxia or brief ischemia paradoxically decreases cardiac injury. It increasingly appears that the cardioprotective paradigms of ischemic preconditioning and post-conditioning utilize modulation of mitochondrial oxidative metabolism as a key effector mechanism. The initially counterintuitive approach to inhibit mitochondrial respiration provides a new cardioprotective paradigm to decrease cellular injury during both ischemia and reperfusion ("Modulation of electron transport protects cardiac mitochondria and decreases myocardial injury during ischemia and reperfusion" Qun Chen, 1 Amadou K. S. Camara, 5 David F. Stowe, 5, 6, 7, 8, 9 Charles L. Hoppel, 2, 3 and Edward J. Lesnefsky 1, 4 *Am J Physiol Cell Physiol* 292: C137-C147, Sep. 13, 2006).

Inhibition of oxidative phosphorylation and ATP depletion deprives cells of energy, forces the cells to shift to glycolysis and to use existing glycogen stores for the production of energy and at the same time increases fatty acid metabolism. Thus, inhibition of OXPHOS by spinosad leads to weight loss and it can be used for the treatment of obesity.

The terms inhibitory concentration IC50 and IC100 (or alternatively lethal dose LD50 and LD100) refer to the concentration of the active that results in 50% and 100% inhibition of the protozoan or the virus or cancer cell viability, respectively. Typically, the IC50 and IC100 may be determined in vitro. In this assay, protozoans, cancer cells or viruses are grown in vitro by methods commonly known in the art. Growth, and subsequent inhibition of growth, are determined by methods also well known in the art. Alternatively, the IC50 and IC100 may be determined in vivo. Growth, and subsequent inhibition of growth, may be measured in vivo by methods commonly known in the art. Typically, such a method would comprise determining the number of protozoans or the viral load in an infected host that was administered an antiprotozoal or antiviral agent or combination of agents in comparison to the number of protozoans or virus load in an infected host that did not receive this agent or combination of agents (i.e., a control host).

In addition to the in vitro and in vivo methods, certain methods of the invention may be performed ex vivo in a subject, to manipulate one or more cell types within the subject. An "ex vivo" method, as used herein, is a method, which involves isolation of a cell from a subject, manipulation of the cell outside of the body, and reimplantation of the manipulated cell into the subject. When returned to the subject, the manipulated cell can be programmed for cell death or division, depending on the treatment to which it was exposed. Ex vivo manipulation of cells has been described in several references in the art, including Engleman, *Cytotechnology*, 25:1, 1997; Van Schooten, et al., *Molecular Medicine Today*, June, 255, 1997; Steinman, *Experimental Hematology*, 24:849, 1996; and Gluckman, *Cytokines, Cellular and Molecular Therapy*, 3:187, 1997.

For an antiprotozoan, antiviral or anticancer spinosyn formulation to be effective, the IC must be able to be achieved at the site of the infection or directed at the cancer cells. The pharmacological absorption and distribution of the spinosyn or spinosyn formulation and its bioavailability, will influence the dose, route and frequency of administration of the drug in order to achieve an effective dose at the desired site. "Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

Pharmaceutically effective amount and administration routes for the spinosyn, according to the present invention, may be optionally selected by those skilled in the art depending on the type of parasites causing the diseases, the location of parasitic part, or the type of virus and viral load, the type of cancer, the severity of the diseases, the therapeutic strategy, and the age, weight, sex, general health conditions and racial (genetic) background of a patient.

The pharmaceutical compositions according to the present invention are administered by any art recognized method including topically, enterally or parenterally in an amount which is effective for treating the specific indication. The topical route of administration includes for example, inhalational, intranasal, intravaginal, epicutaneous, intravitreal, and transdermal. The enteral administration involves oral administration including sublingual and rectal. Parenteral administration includes, intravenous, intradermal, subcutaneous, intramuscular, interperitoneal, intraartirial, intracerebral, intracardiac, intraosseous, intrathecal, and the intravesical route. Parenteral administration also includes continuous infusion i.e., during 2 hours or 12 hours or even 24 hours so as to achieve better distribution of the drug to the target site and better bioavailability.

The spinosyn compositions may be administered to the host, in a fast state, together with food or after meals.

The pharmaceutical composition according to the present invention may be prepared into any formulation known by those skilled in the art appropriate for the chosen administration route. For oral administration the compounds can be formulated into solid or liquid preparations, for example, tablets, lozenges capsules, powders, solutions, emulsions, suspensions and dispersions, colloidal dispersion systems including nanocapsules and microspheres. Such preparations are well known in the art, as are other oral dosage regimes not listed here. The formulation may also be administered topically to skin or mucous membranes as an ointment, lotion, cream, gel or spray. For application by the ophthalmic mucous membrane route, compositions of the present invention may be formulated as eye drops in a physiologically acceptable diluent such as water, saline or DMSO or eye ointments or gels in conventional ocular preparations. Exemplary materials that may be suitable for inclusion in ophthalmic formulations are hydrogels, carbopols, polyacrylic acids, cellosic viscosity enhancing materials and chitosan. Important properties may include adherence to the mucin coat and the corneal surface of the eye to increase residence time of the composition. Cyclodextrins may also be employed in ophthalmic formulations to increase the solubility of the actives in solution. Hyalauronic acid may also be included to increase precorneal residence time. The compounds of the present invention may be also formulated for aerosol administration, particularly to the respiratory tract and including intranasal administration.

Pharmaceutical compositions of this invention suitable for parenteral administration comprise a spinosyn composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

When administering the spinosyns of the present invention, they can be administered systemically or, alternatively, they can be administered directly to a specific site where cancer cells or precancerous cells are present. Thus, administering can be accomplished in any manner effective for delivering the spinosyn pharmaceutical compositions to the cancer cells or precancerous cells.

Systemic administration can also be by transmucosal or transdermal means. For transmucosal or transdermal administration, penetrants appropriate to the barrier to be permeated are used in the formulation. In one embodiment, the transdermal delivery agent can be, for example, DMSO, urea, 1-methyl-2-pyrrolidone, oleic acid, or a terpene (e.g., 1-menthol, d-limonene, RS-(+/−)-beta-citronellol, geraniol). Transdermal delivery systems can include, e.g., patches which deliver a pharmacon continuously through unbroken skin for periods of hours to days to weeks, depending on the particular patch. For transmucosal administration, penetrants appropriate to the barrier to be permeated are used in the formulation, for facilitating the delivery of the drug. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

Other delivery systems suitable for use with the present invention include time-release, delayed release, sustained release, or controlled release delivery systems. Such systems may avoid repeated administrations in many cases, increasing convenience to the animal or human and the physician. Many types of release delivery systems are available and known to those of ordinary skill in the art.

Implantation may be used according to one embodiment of the present invention and includes inserting implantable drug delivery systems, e.g., microspheres, hydrogels, polymeric systems and non-polymeric systems into a host. Use of a long-term release implant may be particularly suitable in some embodiments of the invention. "Long-term release," as used herein, means that the implant containing the composition is constructed and arranged to deliver therapeutically effective levels of the composition for at least 15 or 45 days, and preferably at least 60 or 90 days, or even longer in some cases. Long-term release implants are well known to those of ordinary skill in the art.

For systemic administration, it may be useful to encapsulate the composition in nanoparticles (nanospheres) or liposomes. Nanoparticles exploit biological pathways to achieve payload delivery of molecules to cellular and intracellular targets. Synthetic strategies, including surface, porosity, stealthing and size modifications can be utilized to refine the pharmacokinetic properties of nanoparticles and allow for efficient delivery. The average diameter of such nanoparticles in a composition can range for example from 1-1000 nm. Liposomes are artificial membrane vessels which are useful as a delivery vector in vivo or in vitro and in which a variety of drugs can be incorporated. It has been shown that large unilamellar vessels (LUV), which range in size from 0.2 micrometers to 4.0 micrometers can encapsulate large macromolecules within the aqueous interior and these macromolecules can be delivered to cells in a biologically active form (Fraley, et al., *Trends BioChem. Sci.*, 6:77, 1981). Liposomes for example are encapsulated in a polymer matrix, the liposomes being sensitive to specific stimuli, e.g., temperature, pH, light or a degrading enzyme. Entrapment of drugs into liposomes constitutes an attractive approach to improve and facilitate the delivery of active agents to infected cells and to reduce toxic effects associated with their administration. Because of the similarity of the primary components of liposomes with natural membranes, liposomes are generally non-toxic and biodegradable. In addition liposomes could protect drugs against enzymatic degradation, improve their pharmacokinetics and tissue distribution and may allow a controlled release of therapeutic agents to appropriate cells. In addition, the distribution and therapeutic availability of liposomes can be modulated through variations of their size, lamellarity, lipid composition, charge and surface properties.

We may also have systems in which the composition is encapsulated by an ionically-coated microcapsule with a microcapsule core-degrading enzyme. Examples of systems in which release of the drug is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Finally the spinosyn of the present invention may be conjugated to a water soluble polymer, such as, polyglutamic acid, or a polyaspartic acid or albumin protein or to a water soluble metal chelator, in a way that can achieve higher water solubility than the unconjugated drug and increase the ability to accumulate in a tumor.

Any method or process can be used to prepare the pharmaceutical compositions of the invention, known by the skilled artisan. Solid dosage forms can be prepared by wet granulation, dry granulation, direct compression and the like. The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

During the preparation of the pharmaceutical compositions according to the present invention the active ingredient is usually mixed with a carrier or excipient, which may be a solid, semi-solid, or liquid material with processes and methods known in the art.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. They can also be sold in separate vials which are mixed by the practitioner just prior to use, in order to avoid stability problems of the final formulation.

Spinosyn or a derivative or salt thereof may also be administered as a prodrug. The term "prodrug" as used herein means a pharmacologically acceptable derivative of the compound, such that an in vivo biotransformation of the derivative gives the active compound as a result of i.e., spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active compound during metabolism, systemically, inside a cell, by hydrolysis, enzymatic cleavage, or by some other process (Bundgaard, Hans, "Design and Application of Prodrugs" in *A Textbook of Drug Design and Development*, P. Krogsgaard-Larsen and H. Bundgaard, Eds. Harwood Academic Publishers, pp. 113-191 (1991)). Enzymes which are capable of an enzymatic activation mechanism with the spinosyn prodrug compounds of the invention include, but are not limited to, transaminases, cytochrome CYP450, oxidoreductases, epimerases, dehydratases, methyl transferases, amidases, esterases, phospholipases, and cholinesterases. A prodrug moiety may include an active metabolite or the drug itself.

Prodrugs of spinosyns may be prepared by modifying functional groups present in the spinosyns in such a way that the modifications are cleaved in vivo to give the parent spinosyn. A spinosyn itself might also act as a prodrug, meaning that while it is inactive at the time of its administration, it is activated by specific enzymes or conditions in vivo and starts to exert its activity. In the absence of these enzymes or conditions, it is eliminated from the organism's cells without any effect (activity). Prodrugs are often useful because, in some situations they may be easier to administer than the parent drug. They may, for instance, be bioavailable by oral administration whereas the parent drug is not.

Dosage may be adjusted appropriately to achieve desired drug levels, local or systemic, depending upon the mode of administration. The doses may be given in one or several administrations per day. In most cases the spinosyn dosage for humans and animals will be from 0.05 µg/kg body weight to about 2000 mg/kg body weight daily, administered in one or multiple doses, specifically from 1 mg/kg to about 1000 mg/kg daily or from 5 mg/kg to 200 mg/kg daily and even better from 15 mg/kg to 45 mg/kg daily. In the specific case of topical administration dosages are preferably administered from about 0.05 µg to 50 mg spinosyns per $cm^2$. Parental administration, in some cases, may be from one to several orders of magnitude lower dose per day, as compared to oral doses.

The invention also provides a) a method for inhibiting the growth of a protozoan or a virus by contacting the protozoan or the virus or the cell where it lives with an effective amount of spinosyn or derivative or salt thereof or by changing its vital environment in a way that it cannot live or be reproduced; b) a method for inhibiting neoplastic cell's viability and proliferation by interfering with their vital environment and processes, with an inhibiting effective amount of a spinosyn or derivative or salt thereof; and c) a method of treating a host which can be an animal or a human subject suffering from a protozoan or viral infection or cancer, the method comprising, administering to the host an effective amount of a composition comprising at least one spinosyn or derivative or salt or prodrug thereof and optionally an additional therapeutic agent.

Inhibition of a virus replication in a cell, as described herein, means a reduction in virus replication in a cell to a level lower than the level in an otherwise identical cell, which was not administered the spinosyn of the invention. Preferably, the reduction in virus replication is by about 50% to about 100% relative to the otherwise identical cell, which was not administered the compound of the invention. The level of virus replication in a cell can be assessed by any one of the methods known to the skilled artisan described herein.

The term "contacting" refers to exposing the protozoan or the virus or the cell itself to the spinosyn so that the spinosyn can inhibit, kill, or lyse the protozoan, the virus or the cell where it lives. Contact can occur in vitro, for example, by adding the spinosyn to a cell culture infected with protozoan or a virus to test for susceptibility of the protozoan or the virus to the spinosyn or by adding the spinosyn to a cancer cell culture to test the cancer cell viability and proliferation rate after a certain period of time. Alternatively, contact can occur in vivo, for example by administering the spinosyn to a host afflicted with a protozoan disorder, such as malaria or leishmaniasis or to a host afflicted with a virus disorder, such as for example Herpes simplex virus or Influenza virus or to a host having been diagnosed with cancer. The method for inhibiting the growth of protozoan, virus and cancer can also include contacting the protozoan, the virus or cancer cells with the spinosyn in combination with one or more other drugs.

Carriers as used herein include pharmaceutically-acceptable carriers, solvents, excipients, diluents, buffering agents, isotonifiers, preservatives, adjuvants, including immunologic adjuvants, for example, squalene, stabilizers, ionic and nonionic surfactants or detergents or emulsifiers for example, sodium deoxycholate, which are nontoxic to humans and/or animals exposed thereto at the dosages and concentrations employed. Carriers are used as formulation ingredients, for example, to stabilize or protect the active ingredient within the composition before use, to facilitate the drug delivery, etc. Carriers, as used herein, include also any molecule, for example, a protein, e.g., albumin, which can create conjugates with the spinosyn and thus, facilitates the spinosyn-conjugate (i.e serum albumin-spinosad conjugate) delivery to the target cells.

The terms "pharmaceutically-acceptable carrier" or "physiologically-acceptable carrier" as used herein, includes those carriers that are, within the scope of sound medical judgment, suitable for use in contact with the tissues of humans and animals without undue toxicity, irritation, and allergic response, and are commensurate with a reasonable benefit/risk ratio. Pharmaceutically-acceptable carriers are well known in the art.

The term "carrier" denotes any organic or inorganic ingredient, which may be natural or synthetic, with which one or more spinosyns of the invention are combined to facilitate their administration to the host in need thereof. The carrier may be co-mingled or otherwise mixed with one or more spinosyns of the present invention, in a manner such that we can get the desired pharmaceutical efficacy. The carrier may be either soluble or insoluble, depending on the application. Carriers further include food components and any art recognized diluent or composition that could be used for the administration of spinosyn to the target. Still further, the food carriers include fish and animal feed compositions containing carbohydrates, fats, vitamins, proteins and the like. Non-limiting examples of various physiologically-acceptable carriers may be chosen from an aqueous pH buffered solution, dimethyl sulfoxide (DMSO), oleic acid, alcohols, for example, ethyl alcohol, ketones, ethers, esters and the like, oil and fats such as olive oil, peanut oil, castor oil, corn oil, wheat germ oil, cotton seed oil, silica, cellulose and cellulose derivatives, silicones and siloxanes, hydrophobic and other polymers, calcium stearate, calcium laurate, zinc chloride, magnesium chloride, magnesium oleate, cyclodextrins, mineral oil, white petrolatum, emulsifying wax, pectin, starch, talc, lecithin, proteins, for example, human or bovine serum albumin and others known in the art.

Buffering agents help to maintain the pH in the range which approximates physiological conditions. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities include phosphate buffers, histidine buffers and trimethylamine salts.

Preservatives are added to retard microbial growth. Suitable preservatives for use with the present invention include phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol, formaldehyde, metals for example, mercury or metal salts and combinations thereof.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol, propylene glycol, polyethylene glycol 400; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Non-ionic surfactants or detergents (also known as "wetting agents") may be present to help solubilize the therapeutic agent especially in the case of molecules with very low water solubility, like the spinosyn molecule. Suitable non-ionic surfactants include polysorbates (20, 80, etc.), polyoxamers (184, 188 etc.), Pluronic® polyols, and polyoxyethylene sorbitan monoethers (Tween®-20, Tween®-80, etc.).

Additional miscellaneous excipients can include bulking agents or fillers (e.g., starch), chelating agents (e.g., EDTA), antioxidants (e.g., ascorbic acid, methionine, vitamin E) and cosolvents.

In addition to the active or therapeutic ingredients, the pharmaceutical compositions according to the present invention may contain a number of inert materials referred to herein as excipients. These materials help to impart satisfactory processing and compression characteristics to the formulation including diluents, binders, glidants and lubricants. A further group of excipients helps to give additional desirable physical characteristics to the finished product. Included in this group are disintegrants, colors, flavors and sweetening agents, polymers or waxes or other solubility-retarding materials.

The spinosyns of the present invention may be also administered together with one or more of antipyretics, analgesics, antiemetics and antiallergy drugs.

The primary active ingredient for use in the present invention comprises at least one spinosyn from the class of spinosyns as described above. The percentage of spinosyn in the pharmaceutical composition required for effective protection against protozoans, viruses or neoplastic cell proliferation, may vary substantially depending on the spinosyn itself, the susceptibility of the protozoan, the virus and neoplastic cells to the spinosyn, the method of administration, other additives or actives present in the composition that may influence the effectiveness of spinosyn, the condition of patient or host to be treated, such as his immunologic response, age, body weight, sex, sensitivity, food, time of administration, medicine to be administered concurrently, degree of disease of the patient. The appropriate dose and times of administration of the spinosyn under certain conditions, may be decided through preliminary tests for determining an optimal dose, by a medical specialist in account of the above-mentioned guideline. The upper limit of concentration may be also driven by characteristics of toxicity that would be readily apparent to the skilled artisan.

One skilled in the art would recognize that the amount of spinosyn could be reduced in the event one or more additional active agents were present, for example, other antiprotozoan, antiviral or anticancer agents, so long as the combined composition is effective as an antiprotozoan or antiviral or anticancer agent. The spinosyns of the present invention may be used with one, two (triple) or even three (quadruple) other agents in a multi-drug combination therapy and the agents may be contained in the same formulation or in different formulations. An additional agent may, for example, be selected from the group consisting of biocides, ectoparasites, natural substances (like olive oil), enzyme inhibitors, for example, kinase inhibitors, biomolecule mimics, analytes (including a nanoparticle, an environmental contaminant, or a toxin), other antiviral agents, anticancer agents, antibiotics, antibacterials, antimetabolites, polypeptides, corticosteroids, immunomodulatory agents, antibodies, cytokines, antiprotozoan or other agents used for the parasitic infection diseases.

The term "natural substance" as used herein, includes any chemical compound or substance or product, produced by a living organism found in nature, that usually has a pharmacological or biological activity and may be used as a drug or drug synergist. A natural product can be considered as such even if it can be prepared by synthetic means. Natural substances may be from plant origin, for example, extracts from terrestrial plan tissues, from marine organisms from example, from corals, sponges etc, from animal sources for example, some venoms, microbial metabolites resulting from microorganism fermentation broths etc.

Non-limiting examples of antiprotozoan agents include, for example, Chloroquine, Mefloquine, Altemisinin, Atovaquone, Pyrimethamine, Suramin, Pentamidine, Melarsoprol, Ascofuranone, Benznnidazole, Pentostam, Amphotericin B, Miltefosine, Fluconazole, Quinine, Quinidine, Quinine-doxycycline, Artemether, Artemotil, Artesunate, Arteether, Amodiaquine, Dihydroartemisinine, Piperaquine, Halofantrine, Dapsone, Doxycycline, a Cycline, Lumefanthrine, Proguanil, Pyronaridine, Sulfadoxine, Diamidine, Ferroquine, Fluoroquinolone, Fosmidomycine, Tafenoquine, Eflornithine, Metronidazole, Tinidazole.

Non-limiting examples of other agents used for the parasitic infection diseases, include antinematode agents, like for example Mebendazole, Pyrantel pamoate, Thiabendazole, Diethylcarbamazine and Ivermectin, anticestode agents, for example, Niclosamide and Albendazole, antitrematode agents, for example, Praziquantel and Antiamoebic agents, for example, Rifampin and Amphotericin B.

Non-limiting examples of antiviral agents that may be used with the spinosyns of the present invention as a multi-drug combination therapy include nucleoside reverse transcriptase inhibitors, non-nucleoside reverse transcriptase inhibitors, protease inhibitors or entry inhibitors, and others. Non-limiting examples of antiviral drugs are Purines/Pyrimidinones which include Acyclovir, Cidofovir, Cytarabine, Dideoxyadenosine, Didanosine, Edoxudine, Famciclovir, Floxuridine, Inosine Pranobex, Lamivudine, MADU, Penciclovir, Sorivudine, Stavudine, Trifluridine, Valacyclovir, Vidarabine, Zalcitabine, and Zidovudine. Non-limiting examples of other antiviral agents include Acemannan, Acetylleucine Monothanolamine, Amantadine, Amidinomycin, ATZ, Delavirdine, Foscarnet, Fomivirsen, Sodium, Fuzeon, Indinavir, Interferon-α, Interferon-β, Interferon-γ, Kethoxal, Lysozyme, Methisazone, Moroxydine, Nevirapine, Pleconaril, Podophyllotoxin, Ribavirin, Rimantadine, Ritonavir, Rifampicin, Saquinavir, Stallimycin, Statolon, Oseltamivir (Tamiflu), Zanamivir, Tromantadine, and Xenazoic Acid.

Examples of suitable anticancer agents and drugs that may be used with the spinosyns of the present invention include, but are not limited to, methotrexate, trimetrexate, adriamycin, taxotere, 5-fluorouracil, pamidronate disodium, anastrozole, exemestane, cyclophosphamide, epirubicin, toremifene, letrozole, trastuzumab, megestrol, tamoxifen, paclitaxel, docetaxel, capecitabine, and goserelin acetate. Additional examples of suitable anticancer agents and drugs include, but are not limited to, 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, andrographolide, angiogenesis inhibitors, antagonist D, antagonist G, antarelix, anthramycin, anthracycline antibiotics, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, caiphostin C, calusterone, camptothecin derivatives, canarypox IL-2, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docosanol, dolasetron, doxifluridine, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflornithine hydrochloride, elemene, elsamitrucin, emitefur, enloplatin, enpromate, epipropidine, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, gold (III) chloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitrosourea nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, topoisomerase inhibitors, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinca alkaloids, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as all salts, isomers, homologs, analogs, derivatives, enantiomers of the above and/or functionally equivalent compositions thereof. The systems and methods of the invention can be used in combination with immunotherapeutics, according to another embodiment. The goal of immunotherapy is to augment a subject's immune response to an established tumor or an hematological malignacy, a viral or a protozoan infection. One method of immunotherapy includes the use of adjuvants. Adjuvant substances derived from microorganisms, such as *bacillus* Calmette-Guerin, can heighten the immune response and enhance resistance to tumors in animals. Immunotherapeutic agents are often medicaments which derive from antibodies or antibody fragments that specifically bind to or otherwise recognize a cancer antigen. Binding of such agents can promote an immune response, such as an antigen-specific immune response. Antibody-based immunotherapy may function by binding to the cell surface of a cancer cell, which can stimulate the endogenous immune system to attack the cancer cell.

In yet another set of embodiments, the spinosyn and spinosyn compositions of the present invention may be used in combination with other metabolic inhibitors, like glycolytic inhibitors, oxidative phosphorylation inhibitors and fatty acid metabolism inhibitors.

Non-limiting examples of glycolytic inhibitors are 2-deoxy-D-glucose and analogs. Analogs include derivatives of hydroxyl groups like esters, ethers, phosphoesters, etc. Others include the removal of the hydroxyl group and replacement with halogens like fluorine or iodine, or with thiol or thioalkyl groups like 6-fluoro-D-glucose, 6-O-methyl-D-glucose, 2-iodo-D-glucose, 2-bromo-D-glucose, 2-fluoro-D-glucose etc. Other glycolytic inhibitors are 3-bromopyruvate, 3-fluoropyruvate, 3-chloropyruvate, 3-iodopyruvate, bromopyruvic acid, 5-thio-glucose, oxamate etc.

Non-limiting examples of oxidative phosphorylation inhibitors are oxalate, oligomycin, oligomycin analogs, rutamycin, rotenone, malonate, oxaloacetate, apoptolidin, ossamysin, amytal, and antimycin.

Non-limiting examples of fatty acid metabolism inhibitors are oxirane carboxylic acid compounds, for example: 2-(6-(4-chlorophenoxy)-hexyl)-oxirane-2-carboxylic acid ethyl ester, 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts and most preferably etomoxir, i.e., 2-(6-(4-chlorophenoxy)-hexyl)-oxirane-2-carboxylic acid ethyl ester including homologs, analogs, derivatives, enantiomers and/or functionally equivalent compositions thereof. Other fatty acid metabolism inhibitors are oxfenicine, methyl palmoxirate, metoprolol, amiodarone, perhexyline, aminocarnitine, hydrazonopropionic acid, 4-bromocrotonic acid, trimetazidine, ranolazine, hypoglycin, dichroroacetate, methylene cyclopropyl acetic acid and beta-hydroxy butyrate as well as some antisense oligonucleotides that selectively bind to regions encoding enzymes present within the fatty acid metabolism pathway, such as 2,4-dienoyl-CoA reductase or 2,4-dienoyl-CoA isomerase.

In another embodiment of the invention the spinosyn may be used in combination with a Fas inhibitor (Fas binding molecule or anti-Fas antibody) and/or a UCP (uncoupling protein) inhibitor, for example, a UCP binding peptide or molecule, an anti-UCP antibody, a nucleotide or nucleotide analog etc. The use of 2-deoxy-D-glucose, a glycolysis inhibitor, with a UCP inhibitor and/or a Fas inhibitor has been proposed in the Patent Application No. WO/2005/070126, incorporated herein by reference. It is known that uncoupling protein "UCP" is normally present in the plasma membrane of rapidly dividing cells, but it is not typically found on the plasma membrane of growth-arrested or chemotherapy-resistant tumor cells. UCP, which is also present in the mitochondria, can regulate cell division by manipulating the manner in which the cell processes and stores energy. These findings have important implications on the ability to regulate cell division as well as sensitivity and resistance to chemotherapeutic agents and, therefore, for treating diseases associated with excessive cellular division, aberrant differentiation, and premature cellular death, e.g., for the treatment of cancers, autoimmune disease, degenerative diseases, regeneration, etc. Several cell surface proteins have previously been identified as cell death proteins. Cell death proteins include, for example, Fas/CD95 (Trauth, et al., Science, 245: 301, 1989). Fas ligand (FasL or CD95L) is a type II transmembrane protein that belongs to the tumor necrosis factor (TNF) family. The binding of Fas ligand with its receptor induces apoptosis.

In another embodiment of the invention, the spinosyn and spinosyn compositions and methods of the invention may be used in conjunction with an alkylating (antineoplastic) agent. An alkylating agent is an agent used in cancer treatment that attaches an alkyl group ($C_nH_{2n+1}$) to DNA. The alkyl group is attached to the guanine base of DNA, at the number 7 nitrogen atom of the imidazole ring. Since cancer cells, in general, proliferate faster and with less error-correcting than healthy cells, cancer cells are more sensitive to DNA damage—such as being alkylated. Alkylating agents are used to treat several cancers.

In yet another set of embodiments, the spinosyn and spinosyn compositions and methods of the invention may be used in conjunction with a vaccine, such as a cancer vaccine or an antivirus vaccine. Cancer vaccines are medicaments which are intended to stimulate an endogenous immune response against cancer cells. Currently-produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

In yet another embodiment, the spinosyn and spinosyn compositions and methods of the invention may be used in combination with radiation therapy, administered simultaneously with, sequentially or separately from, the administration of spinosyn composition.

When additional active ingredients are used in combination with the spinosyn compositions of the present invention, the spinosyn composition and the at least one additional active ingredient can be administered to the host simultaneously, sequentially or separately. If the administration is not simultaneous, the compounds may be administered in a close time proximity to each other or after long intervals. Furthermore, it does not matter if the compounds are administered in the same dosage form, e.g. one compound may be administered topically or intravenously and another compound may be administered orally. In addition, the different components of the combination can, independently of the other, follow different dosing schedules, e.g. the spinosyn compounds may be administered daily for a week, or every second week for a three months period, while the at least one additional active is administered one time or twice per week for three weeks followed by a one week period wherein the compound is not administered.

The spinosyn compositions of the invention can be administered once-daily, twice-daily, three times daily, as an instant dose or by continuous infusion (i.e., 1 h or 2 h infusion), once-weekly or once-monthly or in any other dosage protocol. In addition, the administration can be continuous, i.e., every day, or intermittently. The terms "intermittent" or "intermittently" as used herein means stopping and starting at either regular or irregular intervals. For example, intermittent administration can be administration one to six days per week or it may mean administration in cycles (e.g., daily administration for two to eight consecutive weeks, then a rest period with no administration for up to one week) or it may mean administration on alternate days.

According to one embodiment, the spinosyn is present in the composition in an amount in the range from 0.01 μg/ml or grams of composition to 999 mg/ml or grams of composition. According to another embodiment, the spinosyn is present in an amount in the range from 1 μg/ml or grams of composition to 200 mg/ml or grams of composition. According to yet another embodiment, the spinosyn is present in an amount in the range from 10 μg/ml or grams of composition to 100 mg/ml or grams of composition.

According to another embodiment, spinosyn compositions may contain from about 0.001% to about 99.9% by weight of spinosyn, and preferably from about 0.1% to about 50% by weight and most preferably from 1% to 10% by weight.

The content or percentage of the composition that is spinosyn may highly vary depending on the drug form (capsule, liquid, liposome etc.), the route of administration, the need for further dilution or addition of a carrier prior to use (injectables) etc, therefore the formulation/product's concentration of spinosyn is only indicative and is basically used by the practitioner to adjust the proper spinosyn dose expressed as mg/kg/day or mg/m$^2$/day to the host. Selection of a dosage is within the skill of an ordinary artisan, and may be accomplished by starting at a relatively low dosage and increasing the dosage until an acceptable effect is achieved.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches. Notwithstanding that the numerical ranges and parameters setting forth the broad scope of the invention are approximations, unless otherwise indicated the numerical values set forth in the specific examples are reported as precisely as possible, based on the average findings of replicates carried out. Any numerical value, however, inherently contain certain errors necessarily resulting from the standard deviation found in their respective testing measurements.

The following examples are provided to describe the invention in further detail. These examples are intended merely to illustrate specific embodiments of the compositions and methods of the invention, and should in no way be construed as limiting the invention. These examples provide the results of tests conducted to determine the efficacy of spinosyns in inhibiting the growth of certain protozoans, both in vitro and in vivo, viruses and cancer cells. It will be apparent to those skilled in the art that embodiments described herein may be modified or revised in various ways without departing from the spirit and scope of the invention.

ANTIPROTOZOAN TESTS

Example 1

In vitro Test Against *Plasmodium falciparum*

Test sample: deionized water containing 1.1% Tracer® equivalent to 0.5% spinosad (i.e., 5 mg/ml spinosad) Assay: Microscopy Parasite: *Plasmodium falciparum*, strain 3D7

Experimental set-up: One 96-well plate was set up. The plate was used to make Giemsa-stained slides for microscopic confirmation of parasite viability. The highest concentration of the emulsion tested was 20% [i.e. 200 μL of the sample in 800 μL RPMI-1640 medium]. An additional 9.2-fold serial dilutions were also tested. Lowest dilution tested was therefore 0.039% of the sample/0.0002% of spinosad (since initial concentration was 0.5% in the emulsion). The initial parasitemia (percentage red cells infected with parasites) was 1%. Parasites were asynchronous at the start of the experiment (parasites from various stages of the parasite's erythrocytic cycle were present). The hematocrit (percentage of volume occupied by red cells) was 1%. An identical series of controls were set up but using water (filter sterilized) instead of the sample emulsion. Slides for microscopy were made on a daily basis from the plate.

Results: All concentrations of the emulsion tested possessed potent antiplasmodial activity. Microscopy confirmed that there were no viable parasites in these samples. All dilutions of the emulsion that were tested inhibited parasite growth and, interestingly, it was very hard to find remnants of the parasites, consistent with a killing (rather than a static) effect.

Example 2

In vitro Test Against *Plasmodium falciparum*

Using the SYBR green assay method, a 2% spinosad dispersion in DMSO (18.1 mg/ml) was tested against the parasite, *Plasmodium falciparum*, strain 3D7. The IC50 was determined to be about 0.625 μg/ml.

Example 3

In vitro Test of Spinosad Against *Plasmodium falciparum* Chloroquine Sensitive and Chloroquine Resistant Strains Spinosad (coded as 9117) solution in DMSO, was tested against 2 chloroquine sensitive and 2 chloroquine resistant strains of *P. falciparum*, using the 48 h SYBR green growth assay, initiated with ring stage parasites (parasitemia 2%). It has been found that spinosad is equally active against all 4 stains (3D7, FAF6, Dd2, K1). See FIG. 1, FIG. 2, FIG. 3, FIG. 4, which also include the equivalent data with chloroquine.

These data show that spinosyns, and spinosad in particular, have considerable antiplasmodial properties not only against chloroquine sensitive but most importantly against chloroquine resistant strains of *P. falciparum*.

Example 4

In vitro Test of Susceptibility of Different Stages of *P. falciparum* to Spinosad Spinosad (coded as 9117) solution in DMSO, was tested against different stages, rings (which are young parasites) and trophozoites (mature form of the parasite) of *Plasmodium falciparum* intraerythrocytic cycle, to check if it is active more against a particular stage. The antiplasmodial effect of spinosad was tested against 3D7 parasites during 48 h, with 1% initial parasitemia. It has been found that spinosad has the same activity against both rings and trophozoites. See FIG. 5.

Example 5

In vivo Test Against *Plasmodium vinckei* Parasites in Mice

*Plasmodium* is a species specific parasite and we have tested the activity of spinosad in *Plasmodium vinckei* infected mice. For the in vivo efficacy study, 17 BALB/c female mice (with an average weight of 19.3 g) divided in two groups (G1 and G2) were infected with *Plasmodium vinckei*, given intraperitoneally. Mice of group 1(G1) were dosed intraperitoneally for 6 consecutive days, with a daily dose of approximately 50 µl solution of spinosad in DMSO 10 mg/ml (adjusted to a daily spinosad dose of 25 mg/kg). Mice of group 2 (G2) were dosed with 50 µl DMSO (carrier only). Parasitemia was measured from day 5 post-infection. The parasite load levels were determined by optical microscopy and group 1 was compared with the DMSO treated control group 2.

During the treatment period the mice weight was recorded. Weight loss was observed in the first few days of treatment in both groups, but after day 3 the mice weight stabilized in both groups.

Results: In mice treated with spinosad, a 70% reduction ($P=0.0085$) in the number of *Plasmodium vinckei* parasites was observed.

These results demonstrate that spinosad has significant pharmacological properties in mice and it is a potent antimalarial drug in vivo.

Example 6

In vitro Combination of Spinosad with Existing Antimalarial Drugs

Interactions between three standard antimalarials and spinosad were tested. The WHO has mandated that new antimalarials should be used in combination with another antimalarial so that the emergence of drug resistance is reduced. The standard antimalarial that is most commonly used in these combinations is artemisinin (in so-called Artemisinin Combination Therapy, or ACT). When drugs are combined, ideally we would like to have a synergistic effect, but an indifferent (or additive) effect is acceptable as long as they are not strongly antagonistic.

Assays were carried out with the parasites initially in the trophozoite stage of growth. Parasite viability was determined following a 48 h exposure to drug combinations. The following three combinations were tested: spinosad+chloroquine, spinosad+artemisinin, spinosad+quinine. Assuming that one drug in the combination to be tested is called "A" and the other is called "B", stock solutions were prepared containing ratios of A and B. Six combinations were used in the following ratios: 1.0A/0.0B; 0.8A/0.2B; 0.6A/0.4B; 0.4A/0.6B; 0.2A/0.8B; and 0.0A/1.0B. Where 1.0 represents a concentration 8 times higher than the IC50 of a particular drug when tested by itself in previous experiments (i.e. not in combination). These combinations were then serially diluted (2-fold) a total of seven times, and the parasites were added to give a final hematocrit of 1%. The parasitemia was set at 2%. IC50 values were then determined for each combination from dose-response curves (FIGS. 6A-6F where 9117 stands for spinosad).

Fractional inhibitory concentrations (FICs) were then calculated for each drug in a particular combination as follows: FIC (A)=IC50 for A in a combination/IC50 for A alone; FIC (B)=IC50 for B in a combination/IC50 for B alone. The isobolograms (FIGS. 6G-6I where 9117 stands for spinosad) were constructed by plotting FIC (A) versus FIC (B) for each combination. It is generally accepted that a drug combination is synergistic if the FIC values are lower than 0.5 and antagonistic if they are greater than 2 or perhaps even 4. The nature of the interaction between drugs with an FIC of between 0.5 and 2 (or 4) is considered indifferent.

Results: Our conclusion is that there is a clear "indifferent" interaction between spinosad and artemisinin and between spinosad and quinine. There is a very slight antagonistic (although it does not reach the accepted cut-off) between spinosad and chloroquine. The data, therefore, demonstrate that spinosad and artemisinin or quinine can be combined as a combination therapy, because neither drug would interfere with the action of the other.

Example 7

Measurement of ATP Levels in the *Plasmodium* Parasite

We have used the luciferin/luciferase assay to measure the ATP levels, in parasites isolated from *Plasmodium falciparum*-infected erythrocytes. DMSO has been used as a solvent control and NaF, an inhibitor known to decrease in ATP levels within the parasite, as a positive control. The concentration of spinosad used was 5-10 µg/ml in DMSO. This experiment was carried out with parasites still within the red blood cells during the drug exposure period. Parasites were then isolated, so that the measured ATP only reflects that present in the parasite. A similar experiment was carried out with parasites isolated from the host erythrocyte before exposing them to (a) a saline/spinosad medium and (b) an albumin-containing (RPMI-1640)/spinosad medium.

Results: As it is shown in FIG. 10, FIG. 11, spinosad reduces *Plasmodium*'s ATP levels when they are exposed to spinosad in an albumin-containing medium (RPMI-1640) both within the erythrocytes and after being isolated from the host cell, demonstrating a direct action of spinosad on *Plasmodium* (FIG. 11). However, when parasites were exposed to a saline/spinosad medium (i.e. in the absence of albumin), their ATP levels were unaffected (FIG. 10), suggesting that albumin enhances for the activity of spinosad to this parasite. The possibility exists that albumin can be replaced by another protein to support spinosad's activity.

Example 8

In vitro Test Against *Leishmania* Parasites

A 10 mg/ml ethanol solution of spinosad was tested in vitro against the two forms of the *Leishmania* parasite the promastigotes and the amastigotes. In the experiments, the strain *Leishmania donovati* MON-2, responsible for the visceral leishmaniasis in dogs and humans, was used.

Culture of the stationary-phase promastigote form of the parasite with the presence of various concentrations of spinosad, at 26° C., was used to determine the IC50 of spinosad against the parasite promastigotes. Aminosidine and Miltefosine, two well known anti-leishmania drugs have been also tested in vitro, for comparison.

Macrophage mice cell cultures type J774 were infected with the same strain of *Leishmania donovati* MON-2 at a ratio 1:15 (macrophage:parasite) during 4 hours (usually 95% of the cells are infected). Various concentrations of spinosad solution were added and the IC50 of spinosad against the parasite amastigote form was determined.

The cytotoxicity of spinosad, of Aminosidine and of Miltefosine against the macrophage mice cell type J774 was also measured.

Results are set forth in the table below:

TABLE 1

| | $IC_{50}$ in μM | | | |
|---|---|---|---|---|
| | Promastigotes $IC_{50}$ | Amastigotes $IC_{50}$ | Cytotoxicity $CC_{50}$ | Selectivity Index $CC_{50}/IC_{50ama}$ |
| spinosad | 9.5 ± 3.8 | 9 ± 3 | 42.6 ± 17.3 | 4.73 |
| Aminosidine | 5.6 ± 0.6 | 12.8 ± 4 | 447.5 ± 8.6 | 34.96 |
| Miltefosine | 0.87 ± 0.04 | 0.84 ± 0.04 | 32.8 ± 5.1 | 39.04 |

Spinosad is very active in vitro against both promastigote and amastigote forms of the parasite *Leishmania*, making it a very promising candidate as an anti-leishmania drug.

Example 9

In vivo Test Against *Leishmania* Parasites in Mice

For the in vivo efficacy study, 12 BALB/c female mice 10-12 weeks old (weight 23-26 g, n=4 mice per group), were infected with *leishmania donovati* (1.5×10$^7$ promastigotes/mouse) given intravenously in the tail vein. At two weeks post infection, mice of group 1(G1) were dosed intraperitoneally for 14 consecutive days, with a daily dose of 50 μl solution of spinosad in DMSO 15.8 mg/ml (resulting in a spinosad dose of 31.6 mg/kg). Mice of group 2 (G2) were dosed with 50 μl DMSO (carrier only) and group 3 (G3) received no treatment. Three days after the end of treatment, the mice were terminated and the efficacy was evaluated by measuring liver and spleen parasite load levels. The parasite load levels were determined by optical microscopy and each group was compared with the untreated control positive group (+ve).

During the treatment period the mice weight was recorded. Weight loss has been observed in the first days, but after day 10 the mice weight has been stabilized in all groups. No sign of toxicity was observed.

Spinosad had no impact on liver and spleen weight, as no statistical significant difference was observed using the Mann-Whitney test with P<=0.10 (+ve: infected mouse, -ve: normal mouse).

Results: it was observed an 82% elimination of parasites in spleen with P=0.05 (P<=0.1) and in the liver a 73% elimination with P=0.083 (P<=0.1). Between the DMSO dosed and the positive +ve mice, it was not observed any statistically significant difference (Mann-Whitney test with P<=0.10)

Based on the above, spinosad exhibits significant pharmacological properties in mice and it is a potent anti-leishmania drug in vivo.

These data show that spinosyns and spinosad, in particular, have considerable antiprotozoan properties.

ANTIVIRAL TESTS

The in vitro tests for viruses present some restrictions, because viruses can only be developed in the laboratory within specific cell lines (immortalized cancer cell lines), which have to be resistant to spinosyn at the concentration tested against certain virus load. Due to the sensitivity of some of these cell lines to spinosyn, the possibility of testing higher doses against some virus species (i.e. retrovirus) was limited.

Example 10

In vitro Test Against Herpes Simplex 1 Virus (HSV1)

Test sample: clear and sterile solution of 11.92 mg/ml spinosad pure, consisting of a mixture of spinosyn A and spinosyn D in a ratio 70:30, in DMSO (USP).

Assay: Viral Plaque Reduction Assay (virus growth inhibition). This assay tested the ability of a drug to inhibit virus growth as measured by viral induced cytopathic effect. Usually a virus infects a cell and after several days, evidence of virus growth and replication can be observed as changes in the cell monolayer. The monolayer is normally uniform and cells are attached to the dish, however after virus replication, the cells become rounded, may exhibit syncytia formation and frequently detach from the surface to float in the supernatant.

Virus: Herpes Simplex Virus type 1, McIntyre (HSV1), (ATCC VR-539).

Cultured: in Vero cells, African Green Monkey Kidney (ATCC CCL-81)

Experimental Set-Up:

Step 1: Toxicity Assay.

The toxicity assay tested a chemical compound for its potential toxic effect in vitro. The cell lines were cultured in the presence of a range of concentrations of spinosad solution in DMSO. Each cell line was grown in 12 or 24 well dishes and the appropriate concentration of drug was made up in Dulbecco's Minimal Essential cell culture media with 8% fetal calf serum. Cells were cultured for up to five days and observed after 2, 3 and 5 days. The mammalian cells were grown as attached monolayers on treated tissue culture surfaces. If a drug is reported to have 100% toxicity, all cells of the monolayer detach from the growth surface. A normal monolayer with no cells detached would be reported as having 0% toxicity.

Step 2: Virus Growth Inhibition.

We infected spinosad pretreated Vero cell monolayers with a high dilution of Herpes simplex virus 1, sufficient to give about 100 plaques per 10 cm$^2$ monolayer. The infected monolayers were overlaid with media containing gelling agarose as well as the various concentrations of spinosad. Plaques caused by virus infection develop over 2 to 3 days, and are of a certain diameter without drug treatment. Drug treated monolayers showed inhibition of plaque formation and decreased diameter, indicating drug effects on virus growth.

We performed an inhibition of infection assay in which wells were pre-treated with 10 μg/ml of spinosad, which demonstrated no toxicity to Vero cells, and then six different concentrations of virus were added to the treated wells in quadruplicate. A 48 well tissue culture dish was used. Positive and negative controls were included. Endpoint should be graded on viral cytopathic effect on Vero cell monolayers.

Results obtained when using a concentration of 10 μg/ml spinosad:

Plaques on monolayer treated with spinosad, at day 2, were one third the size of plaques with the same virus dilution but with no spinosad. Spinosad treated cell monolayer was healthy at day 7 after infection. Spinosad 10 μg/ml, was able to 100% inhibit approximately 20 infectious units of the HSV1 virus, without affecting the cell. Higher virus loads were not inhibited by the 10 μg/ml spinosad concentration.

Example 11

In vitro Test Against Herpes Simplex Virus 1 McIntyre (HSV1) Using IC50 Assay

We performed an IC50 assay, in which the amount of virus in the quadruplicate assay wells is identical, and the concentration of drug varies over a range of ten concentrations. This assay was performed in a 48 well tissue culture dish, each well containing the appropriate cell line at approximately 90% confluence. Wells were pre-treated with the ten target concentrations of spinosad and then a single dilution of virus. Approximately 100 infectious units per well were added to each test well. Cells, HSV1 virus and drug are incubated for up to 5 days and cytopathic effect is determined. In the two wells that received drug but no virus we observed any possible toxicity of the drug to the cells.

Results: The IC50 of spinosad against 100 infectious units of Herpes Simplex 1 was determined to be about 17.42 μg/ml with no toxicity against Vero cells.

Example 12

In vitro Test Against Herpes Simplex Virus 2 (HSV2) Using IC50 Assay

Test sample: clear and sterile solution of 9.73 mg/ml spinosad pure, consisting of a mixture of spinosyn A and spinosyn D in a ratio 70:30, in DMSO (USP)

Virus: Herpes Simplex Virus type 2, Strain MS-HSV2 (ATCC VR-540)

Cultured: in Vero cells, African Green Monkey Kidney (ATCC CCL-81)

Assay used: IC50 assay as described in example 11 (antiviral), using approximately 50-100 infectious units of the virus Results: The IC50 of spinosad against 50-100 infectious units of Herpes Simplex 2 (HSV2) was calculated to be about 5 μg/ml and the IC100 about 11.5 μg/ml.

These data show that spinosyns, and spinosad in particular, have considerable antiviral properties against viruses belonging to the Herpesviridae family. It is interesting to note here that in virology, even a one log virus reduction i.e. reduction of a virus titre by 90% is important, because in vivo, we want to inhibit the virus replication long enough for the immune system to take over or for other non specific antiviral responses to kick in.

Example 13

In vitro Test Against Influenza a Virus

Test sample: clear and sterile solution of 9.73 mg/ml spinosad pure, consisting of a mixture of spinosyn A and spinosyn D in a ratio 70:30, in DMSO (USP)

Virus: H1N1 Swine Flu virus reassortant X179 (Influenza NCalifornia/4/2009X-179 reassortant)—Center for Disease Control Assay used: IC50 assay as described in example 11 (antiviral), using 50-100 and 250-500 infectious units of the virus.

Cultured: in MDCK (Madin Darby Canine Kidney) cells (ATCC CRL-34)

Results: The IC50 of spinosad against 50-100 infectious units of $H_1N_1$ virus was determined to be about 0.625 μg/ml and the IC100 about 2.5 μg/ml.

The IC50 of spinosad against 250-500 infectious units of H1N1 virus was determined to be about 5 μg/ml and the IC100 about 10 μg/ml.

These data show that spinosyns, and spinosad, in particular, have considerable antiviral properties against viruses belonging to Orthomyxoviridae family and their activity depends on the amount of virus challenged.

A 10 μg/ml spinosad concentration, showed no inhibition of murine Leukemia Virus (ATCC VR-1445) in feline PG4 cells (ATCC CRL-2032) at a virus load of 30 infectious units. Higher concentrations of spinosad may inhibit this virus load in vivo, but unfortunately could not be detected in vitro, due to the sensitivity of PG4 cells to spinosad (experimental restriction).

A 9.5 μg/ml spinosad concentration, showed no inhibition of Respiratory Syncytial Virus Strain A2-RSV (ATCC VR-1540) in HEp2 cells (ATCC CCL-23) at a virus load of 50-100 infectious units. Higher concentrations of spinosad may inhibit this virus load in vivo, but unfortunately could not be detected in vitro, due to the sensitivity of HEp2 cells to spinosad (experimental restriction).

A 4.75 μg/ml spinosad concentration, showed no inhibition of Cytomegalovirus, Davis Strain-CMV (ATCC VR-807) in HS27 Human Foreskin fibroblasts (Diagnostic Hybrids, Athens Ohio, 87-T025) at a virus load of 50-100 infectious units. Higher concentrations of spinosad may inhibit this virus load in vivo, but unfortunately could not be detected in vitro, due to the sensitivity of HS27 cells to spinosad (experimental restriction).

ANTICANCER TESTS

Example 14

This in vitro laboratory study examined the cytotoxicity of spinosad used as a 3 mg/ml DMSO solution, in four human cancer cell lines (BxPC-3, DU 145, PC-3 and MDA-MB-231). Spinosad in DMSO vehicle was administered as a solution in the cell culture growth media, at a concentration of not more than 1% vehicle in media. We also examined the effect of spinosad on the proliferation rate of highly proliferating cancer cells.

Cell Lines used:

(1) BxPC-3 (ATCC CRL-1687™) Human pancreatic adenocarcinoma

Growth Media: Complete=RPMI-1640 medium plus 10% FBS (Gibco).

(2) DU 145 (ATCC HTB-81™) Human prostatic carcinoma cells.

Growth Media Complete=DMEM medium plus 10% FBS (Gibco).

(3) PC-3 (ATCC CRL-1435™) Human prostatic adenocarcinoma cells

Growth Media: Complete=F-12 Kaighn's medium plus 10% FBS (Gibco).

(4) MDA-MB-231 (HTB-26™) Human breast adenocarcinoma cells.

Growth Media Complete=Leibovitz's medium plus 10% FBS (Gibco).

Assessment of Cell Survival: All cell lines were propagated on the bottom surface of sterile tissue culture dishes or flasks in appropriate complete sterile growth medium with 10% heat-inactivated fetal bovine serum, in a humidified incubator at 37.0±2° C. with 95±2% air, 5±2% $CO_2$. For cell survival assessment, cells at a density of approximately 70-80% confluency were treated with dosing media by the addition of fresh growth medium containing the appropriate concentrations of the vehicle DMSO or spinosad in DMSO. After exposure to treatments, the dosing media was replaced with fresh growth media and cell cultures were incubated for 24 hours before collection of cells and measurement of viable cell numbers/mL. The solutions were then removed, and adherent (viable) cells collected from the flasks. 2 mL of each cell suspension in growth media (from each flask) was obtained. 50 μL of each cell suspension was mixed with 50 μL of 0.4% trypan blue solution, and a sample of this mixed suspension was then placed in a hemacytometer (Hausser Scientific) and cells counted under a microscope to determine the number of viable cells/mL. Viability was identified by the absence of cytosolic trypan blue staining. The number of viable cell/mL in the test groups was compared to the number of viable cells/mL in the control group and cell survival expressed as a % of control (control=100% survival).

Results: For the cell survival assay, 24-hour exposure of all cancer cell lines to spinosad decreased cell survival at approximately 24 hours post end of exposure in a dose-dependent manner. The calculated $LC_{50}$ and $LC_{100}$ values of spinosad, 24 h post end of exposure are given in the table 2 below:

TABLE 2

Cell Survival 24 h post spinosad treatments (Cytotoxicity Study)

| spinosad Dose (μg/mL) | BxPC-3 Cells | DU 145 Cells | PC-3 Cells | MDA-MB-231 Cells |
|---|---|---|---|---|
| | Cell Survival (% of Control; mean ± S.D.) | | | |
| 10 | 54.1 ± 9.8 | 56.8 ± 3.1 | 53.8 ± 8.0 | 56.1 ± 13.7 |
| 20 | 25.5 ± 2.6 | 30.2 ± 4.5 | 42.0 ± 9.5 | 38.0 ± 5.7 |
| 30 | 5.3 ± 2.6 | 7.6 ± 4.1 | 5.9 ± 2.5 | 13.2 ± 1.4 |
| | Calculated $LC_{50}$ and $LC_{100}$ of spinosad (μg/mL) | | | |
| $LC_{50}$ | 11.1 | 12.5 | 13.3 | 13.4 |
| $LC_{100}$ | 31.6 | 32.8 | 34.2 | 36.7 |

Cell Proliferation assay: for each cell line, cell suspensions ranging in concentration of approximately 2-5×10$^5$ cells/mL of growth medium were prepared. 1 mL of each of these suspensions was aseptically transferred to a sterile tissue culture flask (12.5 or 25 cm$^2$) containing fresh growth medium. Three flasks (triplicate) were used for each group, and for each time point of viable cell number/mL measurement at 1, 3 and 5 days post-treatment (9 dishes per group in total). The cells were incubated and allowed to adhere to the bottom of the flasks and proliferate.

Cell Treatments: for each cell line, when the cells reached a density of approximately 20-40% confluency at the bottom of the flasks, the cells were treated with dosing media by the addition of fresh growth media containing the appropriate concentrations of the control (vehicle) or spinosad. After approximately 24 hours of exposure to treatments, dosing media was replaced with fresh growth media and cells were returned to the incubator and allowed to proliferate.

Assessment of Cell Proliferation: For each cell line, measurement of viable cell number/mL was performed as already described above. This measurement was performed in triplicate from three flasks per group, at 1, 3 and 5 days post-removal of treatment. From the numerical data collected, growth curves of viable cell number/mL versus time post-treatment were generated to compare the proliferative capacity (cytostatic effect of spinosad) of cells in the control and test groups.

Results: For the cell proliferation assay, 24-hour exposure of all cancer cell lines to spinosad decreased the rate of cell proliferation at 1, 3 and 5 days post-exposure, in a dose-dependent manner, as determined by viable cell number/mL values. At the low dose level (5 μg/mL), the decreased proliferative rate was comparable between all cell lines tested (cell number doubling time from 3 days post-treatment increased by approximately 27.8-33.2%). At the high dose level (15 μg/mL), MDA-MB-231 breast adenocarcinoma cells exhibited the highest sensitivity (cell number doubling time from 3 days post-treatment increased by approximately 129.3%) and DU 145 prostatic carcinoma cells exhibited the lowest sensitivity (cell number doubling time from 3 days post-treatment increased by approximately 46.5%) to inhibition of cell proliferation following spinosad treatments.

A summary of the calculated cell number doubling times for each cancer cell line is provided in Table 3 below and graphs of Viable Cell Number/mL vs. Day Post-Dose for each cancer cell line at all spinosad dose levels are shown in FIGS. 7A-7D.

TABLE 3

Cell Number Doubling Times After spinosad Treatments

| | Cell Number Doubling Time (Days) | | | |
|---|---|---|---|---|
| spinosad Dose (μg/mL) | BxPC-3 Cells | DU 145 Cells | PC-3 Cells | MDA-MB-231 Cells |
| 0 (Control) | 3.02 | 2.17 | 3.22 | 3.11 |
| 5 | 3.86 | 2.89 | 4.17 | 3.99 |
| 10 | 4.76 | 2.83 | 5.55 | 5.09 |
| 15 | 6.25 | 3.18 | 6.24 | 7.13 |

Based on these findings, it is demonstrated that spinosad has cytotoxic and cytostatic activities in the human cancer cell lines. The cytostatic activity is expected to be further increased when cancer cells are exposed to spinosad for a longer than 24 h period.

Example 15

Mouse Pancreatic Tumor Xenograph Assay for Evaluation of Spinosad Anticancer Activity We have conducted a mouse pancreatic tumor xenograph assay for the evaluation of spinosad anticancer activity on CD-1 athymic nude male mice (CD-1®-Foxn1$^{nu}$, mus musculus, source Charles River Canada Inc., age 9-10 weeks and weight 25-35 gr at dosing). During a period of 20 days, a total spinosad quantity of 360-615 mg/kg was administered intraperitoneally in each mouse of the drug treated group, as a 10 mg/ml DMSO solution, in doses of 30 or 45 mg/kg, once or twice per day and with intervals of no dose. The control group received the equivalent quantity of DMSO. Data are presented in Table 4 below.

TABLE 4 data from mouse pancreatic tumor xenograph assay

| mouse code | total spinosad dosed mg/kg | tumor volume on day1 (mm³) | tumor volume on day 21 (mm³) | % difference | mean volume change |
|---|---|---|---|---|---|
| 1 | 0 | 155.0 | 226.1 | 46% | 54% |
| 2 | 0 | 197.5 | 241.9 | 22% | |
| 4 | 0 | 157.8 | 378.9 | 140% | |
| 5 | 0 | 163.8 | 178.0 | 9% | |
| 3 | 390 | 184.7 | 107.7 | −42% | −21% |
| 6 | 360 | 260.6 | 254.7 | −2% | |
| 9 | 540 | 179.9 | 119.8 | −33% | |
| 10 | 540 | 228.9 | 128.9 | −44% | |
| 12 | 615 | 159.4 | 142.1 | −11% | |
| 13 | 585 | 233.3 | 246.5 | 6% | |
| | | | | P < 0.02 | 0.0193 |

Results: On the 21$^{st}$ day we measured tumor volumes of all mice. In the spinosad treated group the mean tumor volume decreased by 21% while in the control/DMSO treated group the mean tumor volume increased per 54% with a P-value <0.02. With the above pilot in vivo test, we have demonstrated that spinosad has anticancer activity in vivo.

High doses of DMSO alone (control group), in the first 3 days have resulted in significant weight loss, on top of some weight loss observed with the administration of spinosad, therefore the experimental conditions were modified from the initial protocol, based on the condition of the mice, by giving a rest to the mice in order to compensate for the weight loss. Results to date have been presented; however, the experiment is on going.

Example 16

Effect of Spinosad on Cellular Bioenergetics

With this test we can see the effect of spinosad on cellular metabolism and on bioenergetics of cancer cells. The experiment was performed in a Seahorse XF-24 analyzer, using spinosad concentrations in DMSO of 10 μg/mL and 20 μg/mL during 24 hours after addition of the drug on NCI-H460, a large cell lung carcinoma cell line.

NCI-460 (ATCC Cat# HTB-177) was ordered as a frozen vial from ATCC. These cells were counted for viability after thawing and revived in a single T75 flask in RPMI media with 10% FBS according to ATCC instructions. The media was supplemented with Penstrep (ATCC Cat #30-2300) and amphotericin (Lonza Cat #17-836R). Based on a combination of microscopy observations and XF-24 Analyzer based Oxygen Consumption Rate (OCR) and Extra Cellular Acidification Rate (ECAR), the optimal cell density used in the study was determined at 35,000 cells per well.

OCR and ECAR measurements in the XF-24 Analyzer on H460 cells, suggest that spinosad affects energy production pathways in the cell as it is shown in FIGS. 8A-8D. The drug has an initial effect on OCR suggesting its role as an oxidative phosphorylation (oxphos) inhibitor. A dose dependent decrease in OCR is also noted as demonstrated in FIG. 13 when using 10 μg/ml spinosad. ECAR is relatively unaffected at 7.6 hours after treatment with spinosad; however, ECAR effects are clear after 8 hours and it is suggested to be due to cell death rather than a direct effect. For comparison, the data from untreated samples (FIG. 8B) and a glycolysis inhibitor positive control (FIG. 8C) have also been included. To account for any effects due to pH changes caused by spinosad, one blank cell was injected with spinosad at a concentration of 20 μg/mL (FIG. 8D).

This example confirmed that spinosad affects metabolic processes of energy production within H460 cells and particularly it inhibits oxidative phosphorylation (oxphos). The oxphos is shown to be affected as early as 1 hour post spinosad injection while at 3 hours, the oxygen consumption reduction becomes statistically significant. More specifically, oxygen consumption of H460 cells treated with 20 μg/mL spinosad for 3 hours is decreased by 50% compared to the control.

To extend our understanding of these results, we also measured the cytotoxicity of spinosad on H460 cells when treated with 20 μg/mL spinosad for 3 hours, in order to evaluate if the drop in OCR is a manifest of a primary cytotoxic effect, using the ApoTox-Glo™ Triplex assay system, from Promega Corporation. The data from this study has determined no cytotoxicity at a concentration of 20 μg/mL spinosad for 3 hours of treatment. In FIG. 12 it is shown the dose response curve on H460 cell viability, at three hours timepoint, after treatment with various concentrations of spinosad. The n=1, n=2 and n=3 stand for the three replicates. Thus, we conclude that the OCR drop, preceded the cytotoxic or necrotic effect of spinosad. The effect of spinosad on glycolysis is likely an indirect consequence of the effects on oxidative phosphorylation.

Results: This example has successfully shown that the oxidative phosphorylation pathway from which most of a cell's ATP is generated, is rapidly affected by spinosad.

Example 17

Effect of Spinosad on Oxygen Consumption in Isolated Mitochondria

Oxygen utilization that results in ATP production, measureable by OCR in the Seahorse XF24 Analyzer, is one of the primary functions of the mitochondria. To examine whether spinosad directly affected the mitochondria, we isolated mitochondria of untreated H460 cells, we exposed them to various spinosad concentrations and measured oxygen consumption in these mitochondria. This set of experiments required highly intact and coupled mitochondria capable of showing a response to exogenously provided ADP. For the isolation of mitochondria the Mitochondrial Isolation Kit for Cultured Cells (Mitosciences Eugene Oreg. Cat # MS 853) was used. Once isolated, equal volumes of mitochondrial suspension were taken into separate eppendorf tubes and left untreated or treated with DMSO or different concentrations of spinosad at 4° C. for three hours. Each of the samples was equally aliquoted into the Seahorse culture plate wells. Starting with a single batch of mitochondrially enriched samples, there was observed a dose dependent decrease in ADP stimulation with increased spinosad concentration treatment. A slight increase was seen in ADP stimulation with 20 μg of spinosad, but there is a significant decrease observed with the higher concentration of the compound. See FIG. 9. The substrate used in the assay was succinate that allows electron transfer through Complex II. For the protein estimation, the Protein Estimation-Bradford assay was used.

Mitochondrial compounds were loaded into the ports of the cartridges as described in Table 5. The compounds were made up in Mitochondrial Assay Solution-1 (MAS-1).

TABLE 5

Mitochondrial compounds and their final concentrations used in the assay.

| Injection Ports | Volume | Concentration in Port | Final concentration Well |
|---|---|---|---|
| A: ADP | 50 μL | 2.5-40 mM | 0.25-40 mM |
| B: Oligomycin | 55 μL | 20 μM | 2 μM |
| C: FCCP | 60 μL | 10 μM | 1 μM |
| D: Antimycin A | 65 μL | 40 μM | 4 μM |

These data show that the coupling of mitochondria was not affected at the lower concentrations of spinosad tested, but there was observed a dose dependent decrease in ADP stimulation with increased spinosad concentration. We have observed an effect at concentrations above 40 μg/mL and more clearly at 80 μg/mL. The current dataset confirms that OXPHOS through Complex II is reduced by spinosad. The data correlates well with the cytotoxicity studies with the test compound since cell viability decreases at concentrations higher than 20 μg/mL at three hours of treatment. The earlier metabolic studies have shown an inhibition of OCR at a concentration of 20 μg/mL after three hours of treatment. The decrease is not seen in this study at a concentration of 20 μg/mL. However the temperature at which the drug treatment was conducted (i.e. 4° C.) changed the kinetics of spinosad uptake and effected and increased the time needed for a drop in OXPHOS to be observable.

The Respiratory Control Ratios (RCR) of the different treatment groups are shown in Table 6 below. The RCR was a measure of mitochondrial coupling between respiration and phosphorylation. The RCR values were calculated as a ratio of State III and State IV respiration. The data demonstrate that mitochondrial integrity is reduced above 40 μg/mL spinosad concentration, under the specific experimental temperature and conditions.

TABLE 6

| Sample | RCR |
|---|---|
| Untreated | 1.8 = 860/480 |
| DMSO | 2.1 = 750/320 |
| 10 μg/mL | 2.4 = 711/300 |
| 20 μg/mL | 2.2 = 726/330 |
| 40 μg/mL | 1.55 = 666/430 |
| 80 μg/mL | 1.19 = 598/500 |

RCR values

To confirm that the differences in OCR stimulation in the presence of ADP are indeed caused by the spinosad test compound and it is not due to differences in protein amounts in each well, equal volumes of the different mitochondrial samples were loaded on a 12% SDS-PAGE gel. The stained gel in FIG. 14 shows proteins present in the mitochondria and those in the buffer. The arrows are pointing to those bands that are mitochondrial proteins. These bands were visually determined to have similar staining intensities in all lanes, except the one with MAS-1, showing that each of the wells in the Seahorse wells had equal amounts of protein.

Results: Based on the above experiment we conclude that the spinosad acts directly on the mitochondria. There is a dose response of spinosad on isolated mitochondria of the H460 cancer cell line, after 3 hours of incubation at 4° C. A spinosad dose above 40 μg/mL and better above 80 μg/mL, when compared to DMSO treated and untreated cells, resulted in Decreased State III respiration and Lowered RCR ratio. The recordings for OCR were conducted when using Succinate as a substrate and the data collected represent activity from Complex II down the electron transport chain.

BRIEF DESCRIPTION OF THE DRAWINGS

The accompanying drawings, which are incorporated in and constitute a part of the specification and written description, illustrate the exemplified embodiments and, together with the description, serve to exemplify the principles of the claims.

FIGS. 8A-8D shows the effect of spinosad on cellular metabolic pathways of H460 cancer cells FIG. 9 shows the effect of spinosad on OCR of isolated mitochondria when treated with the control and various concentrations of spinosad

Figure 1:
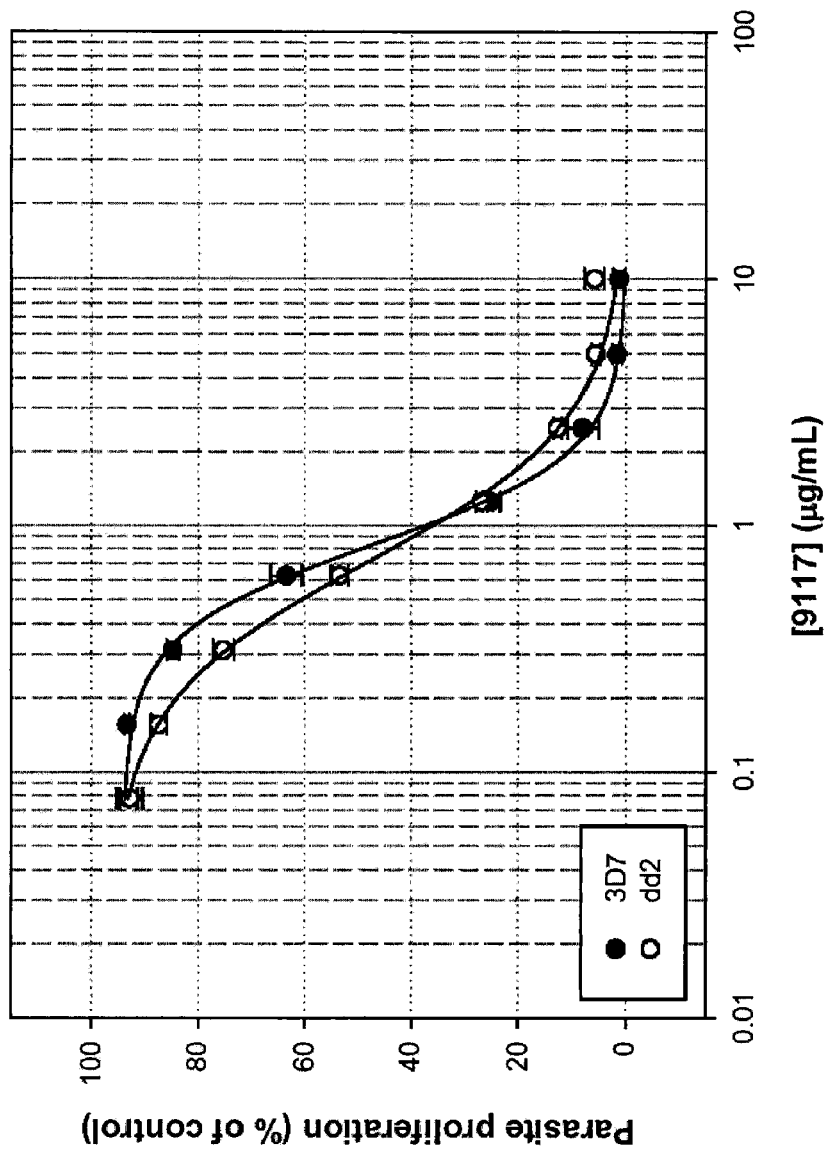
FIG. 1 shows the effect of spinosad on proliferation of 3D7 and Dd2 *Plasmodium* parasites
Figure 2:
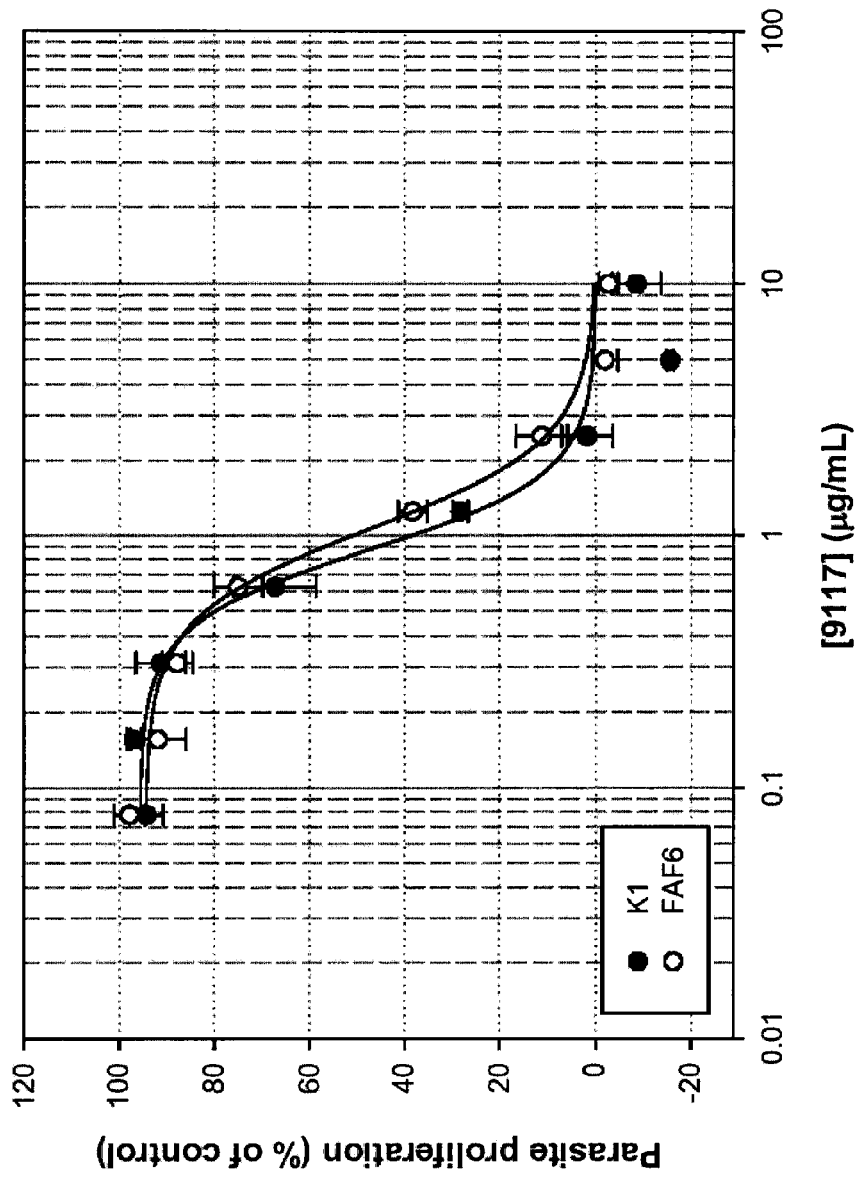
FIG. 2 shows the effect of spinosad on proliferation of Kb 1 and FAF6 *Plasmodium* parasites
Figure 3:
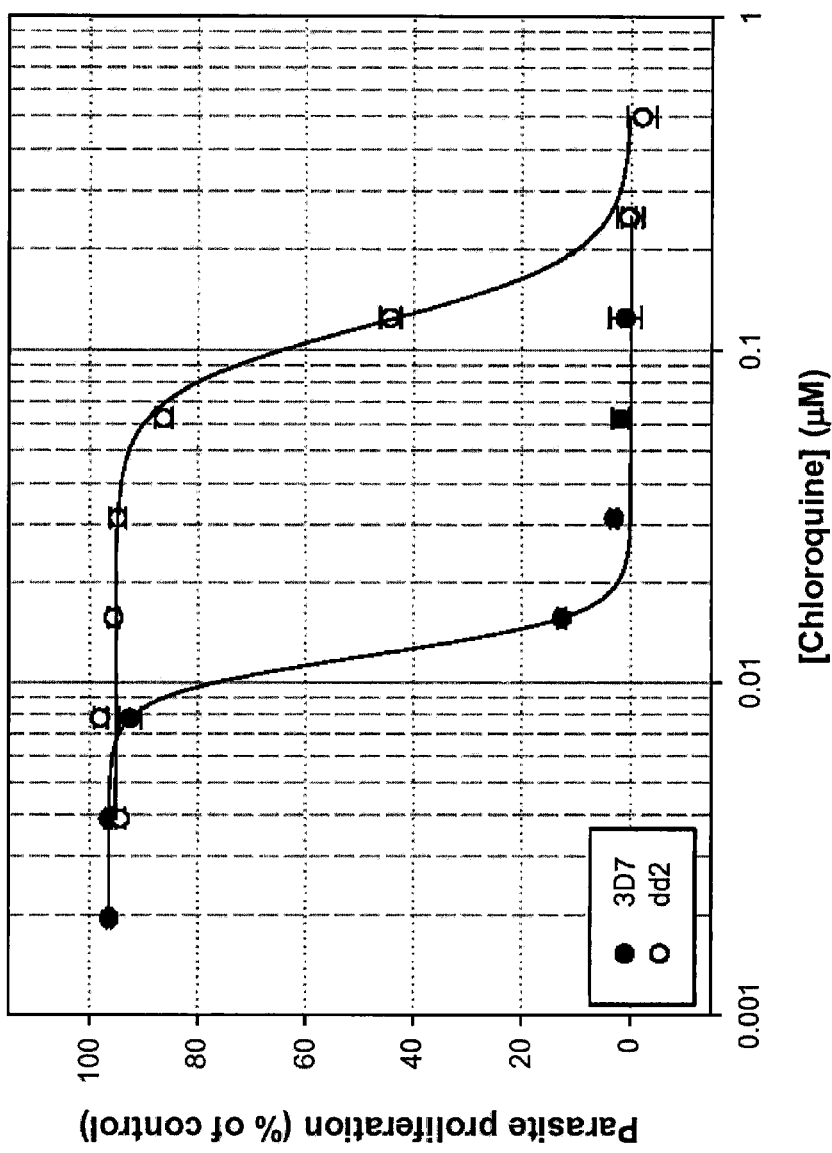
FIG. 3 shows the effect of chloroquine on proliferation of 3D7 and Dd2 *Plasmodium* parasites
Figure 4:
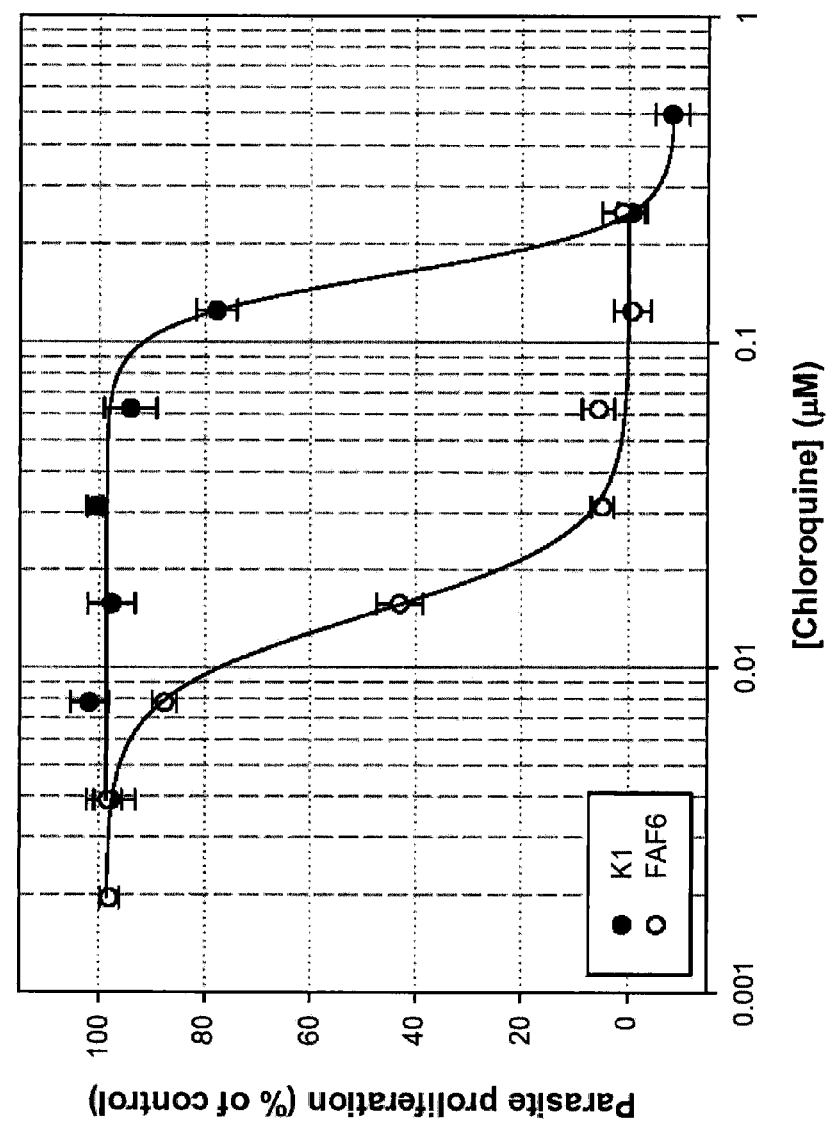
FIG. 4 shows the effect of chloroquine on proliferation of K1 and FAF6 *Plasmodium* parasites
Figure 5:
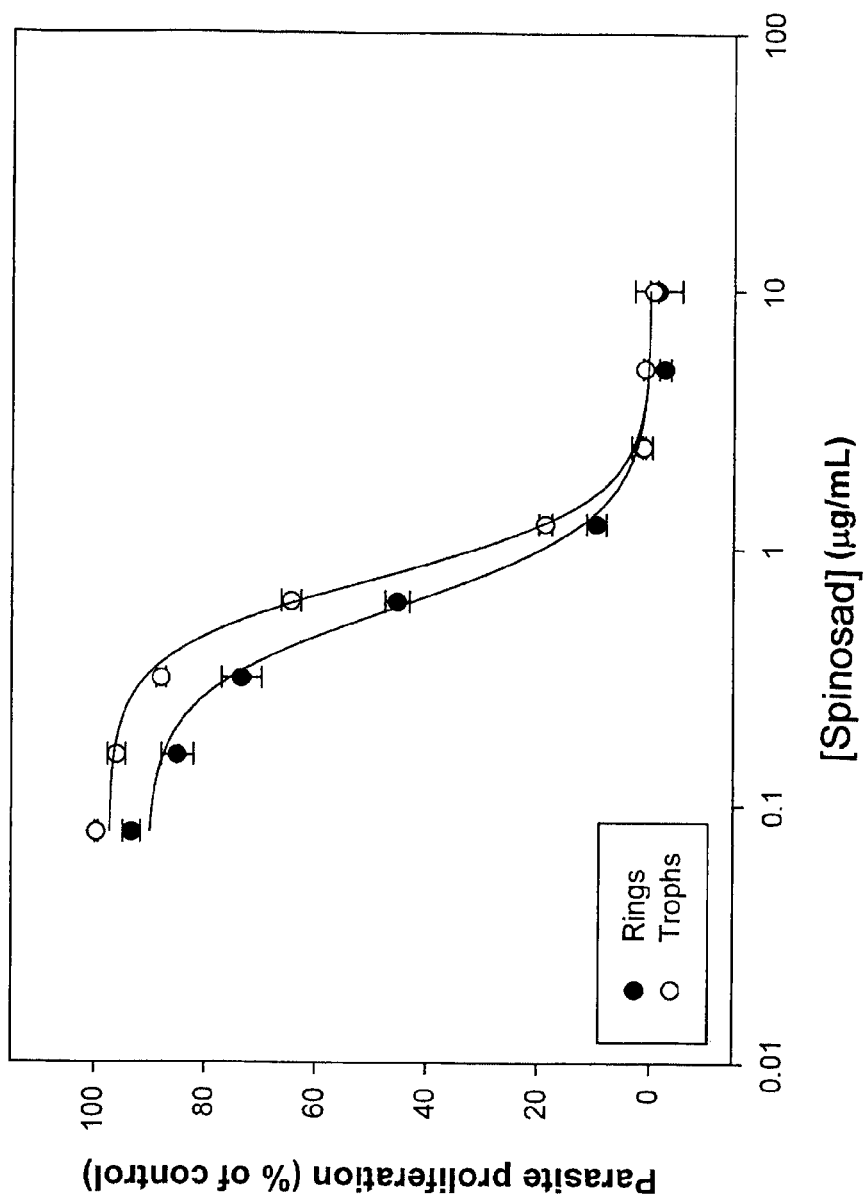
FIG. 5 shows the antiplasmodial effect of spinosad on ring-stage and trophozoite *Plasmodium* parasites.
Figure 6A:
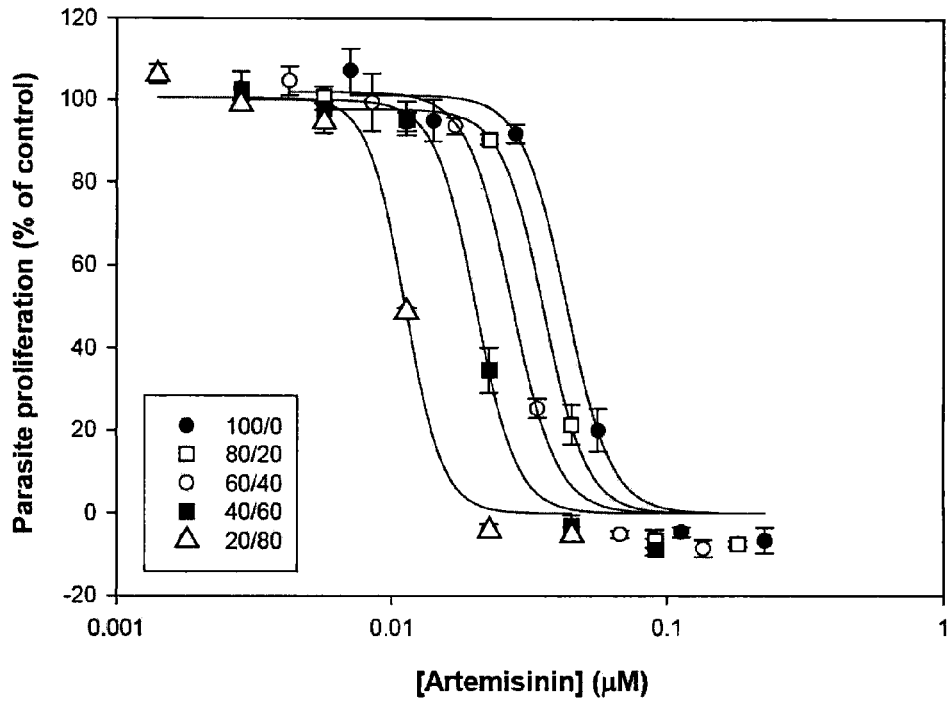
FIGS. 6A-6I shows isobolograms
Figure 6B:
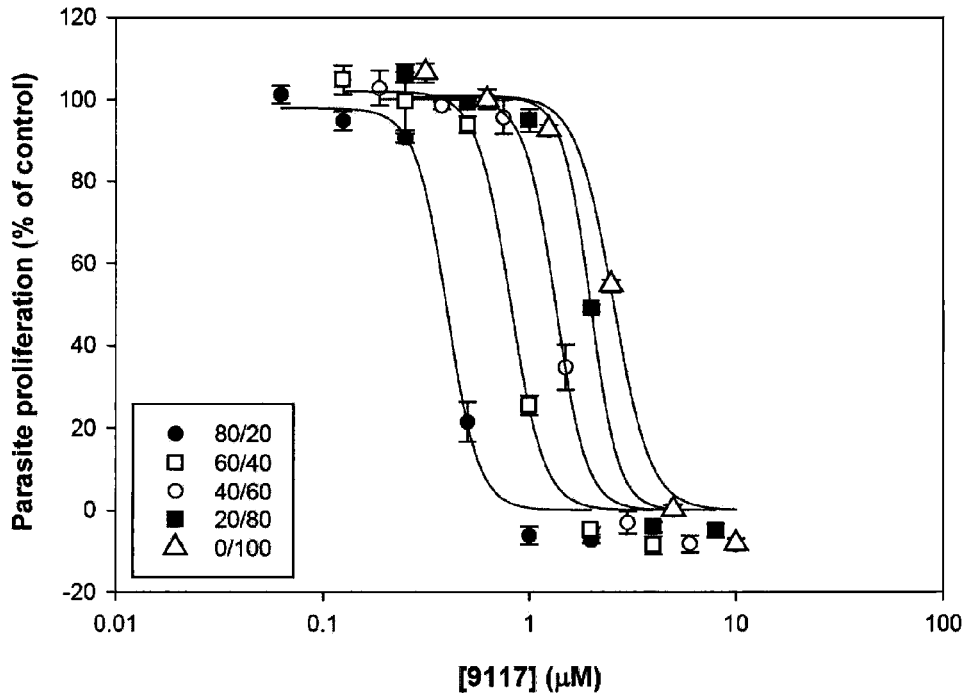
Figure 6C:
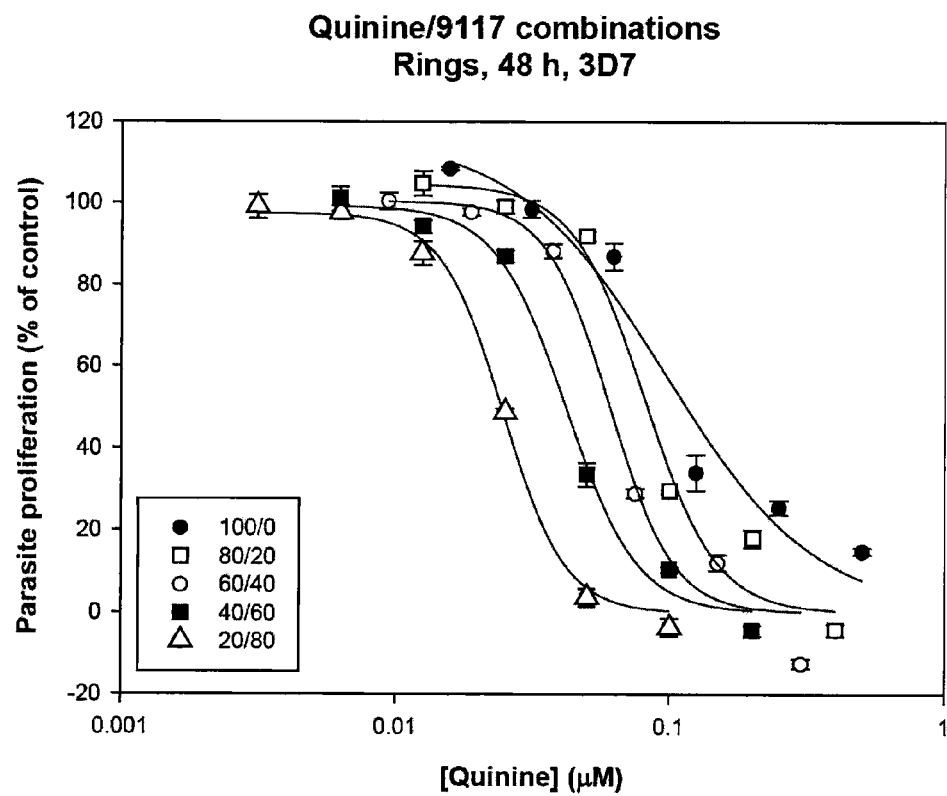
Figure 6D:
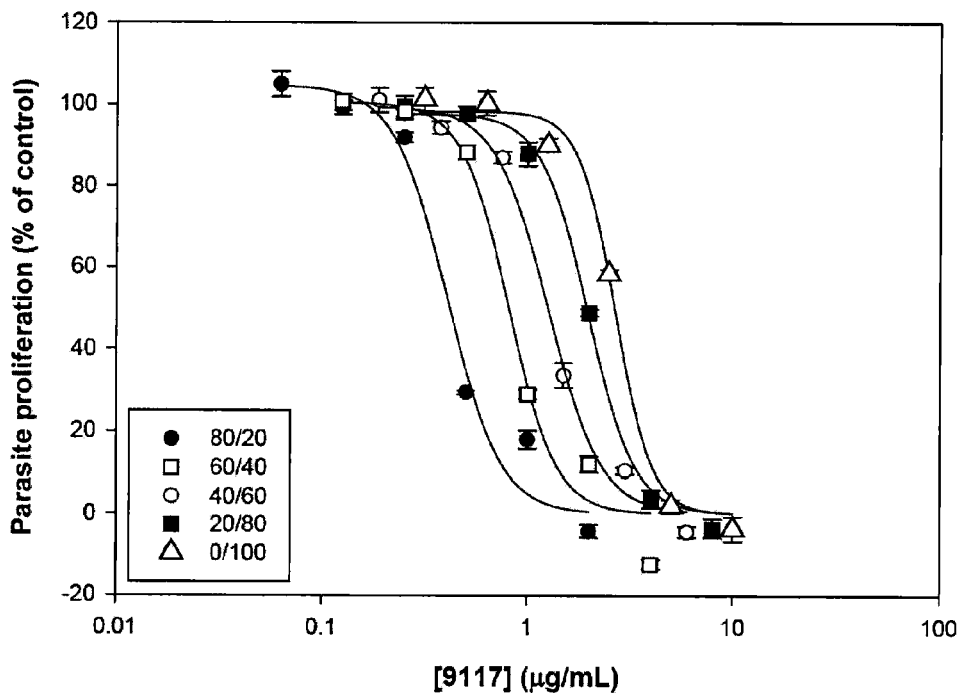
Figure 6E:
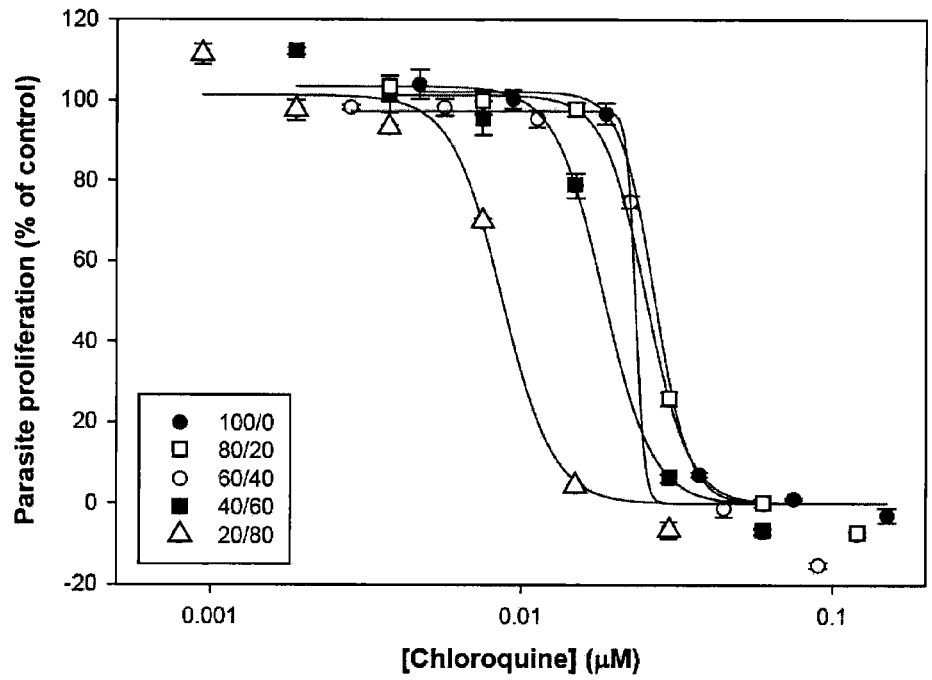
Figure 6F:
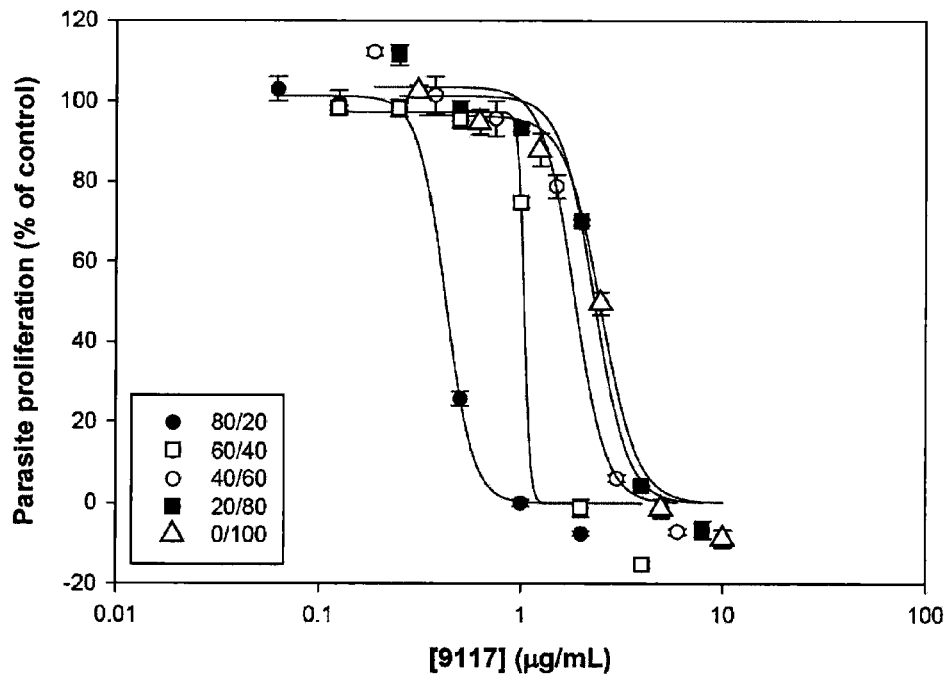
Figure 6G:
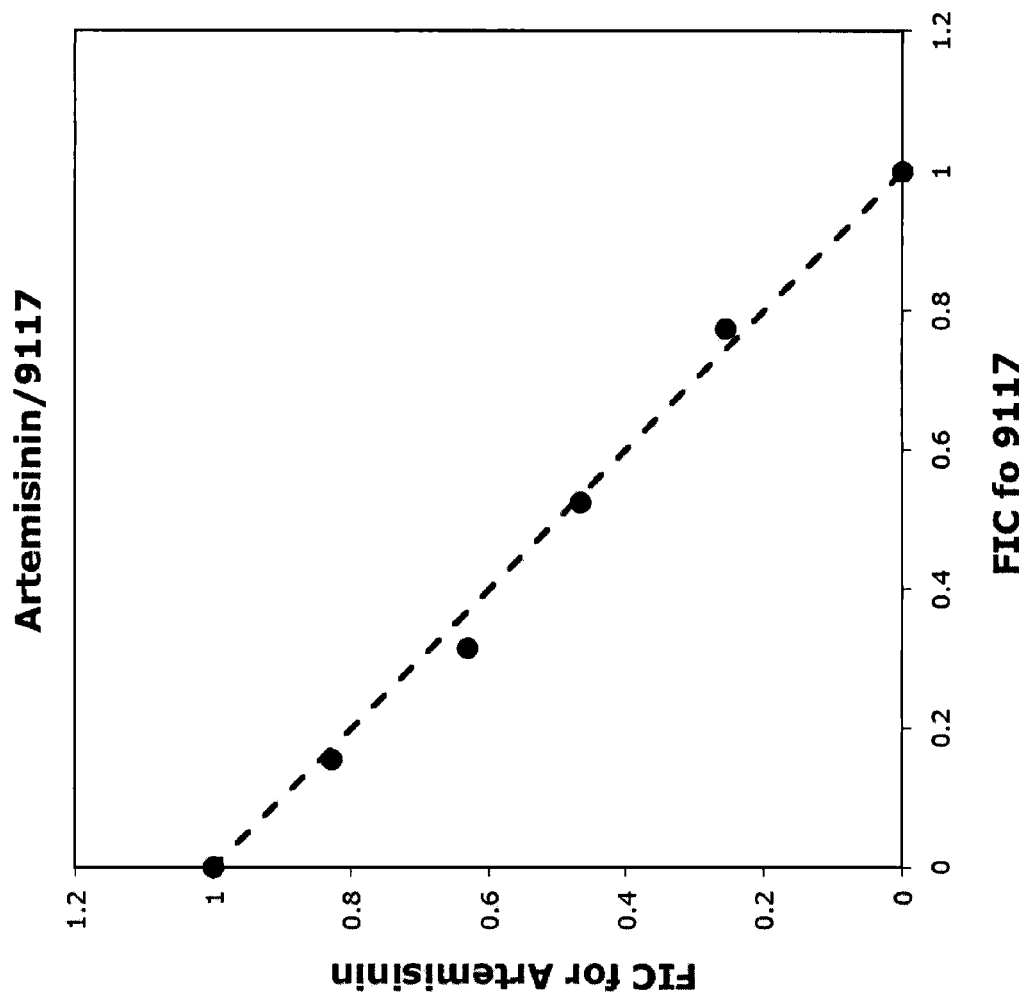
Figure 6H:
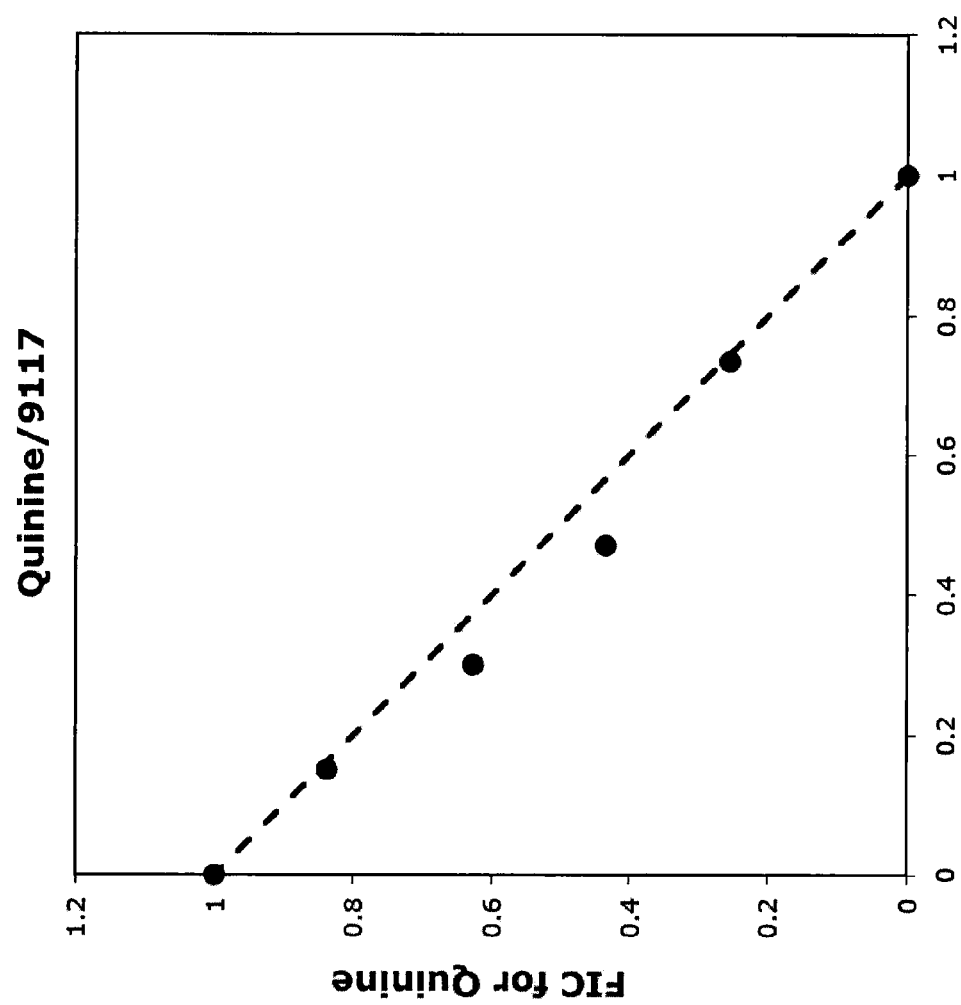
Figure 6I:
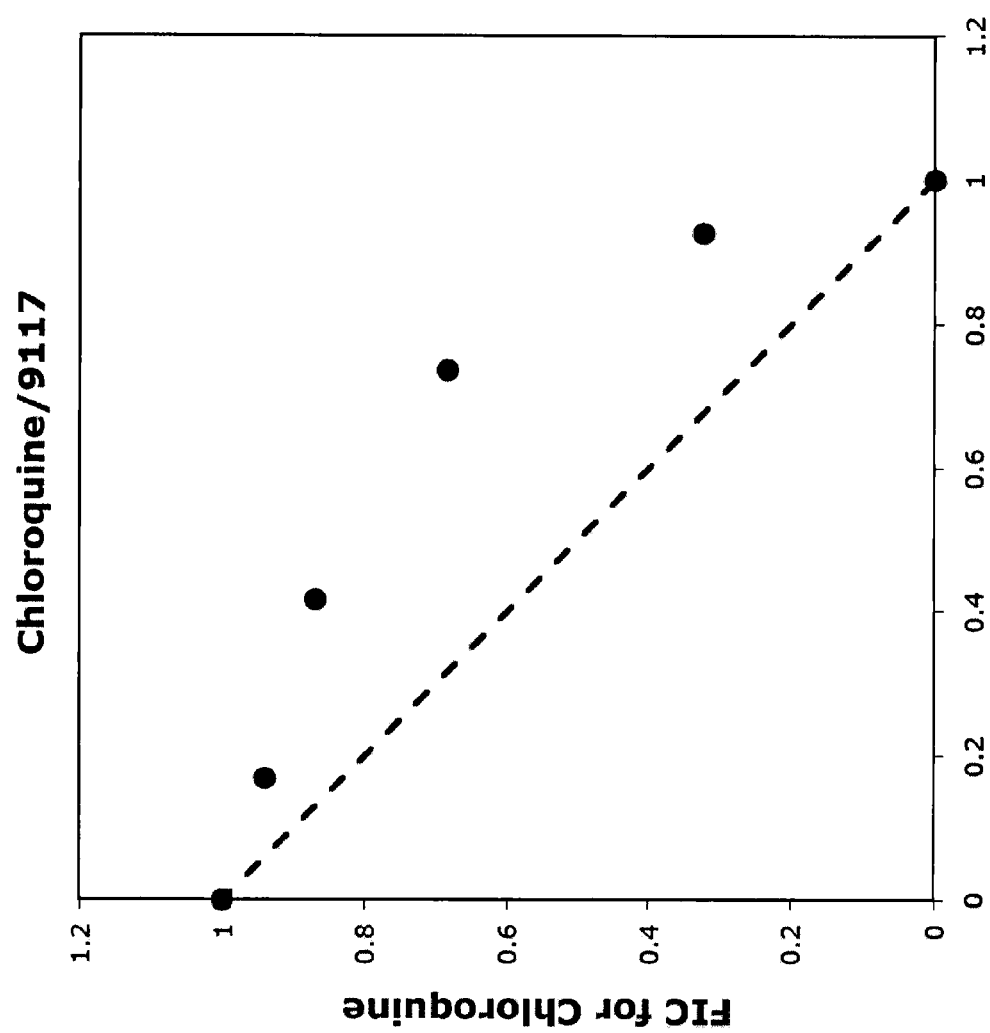
Figure 7A:
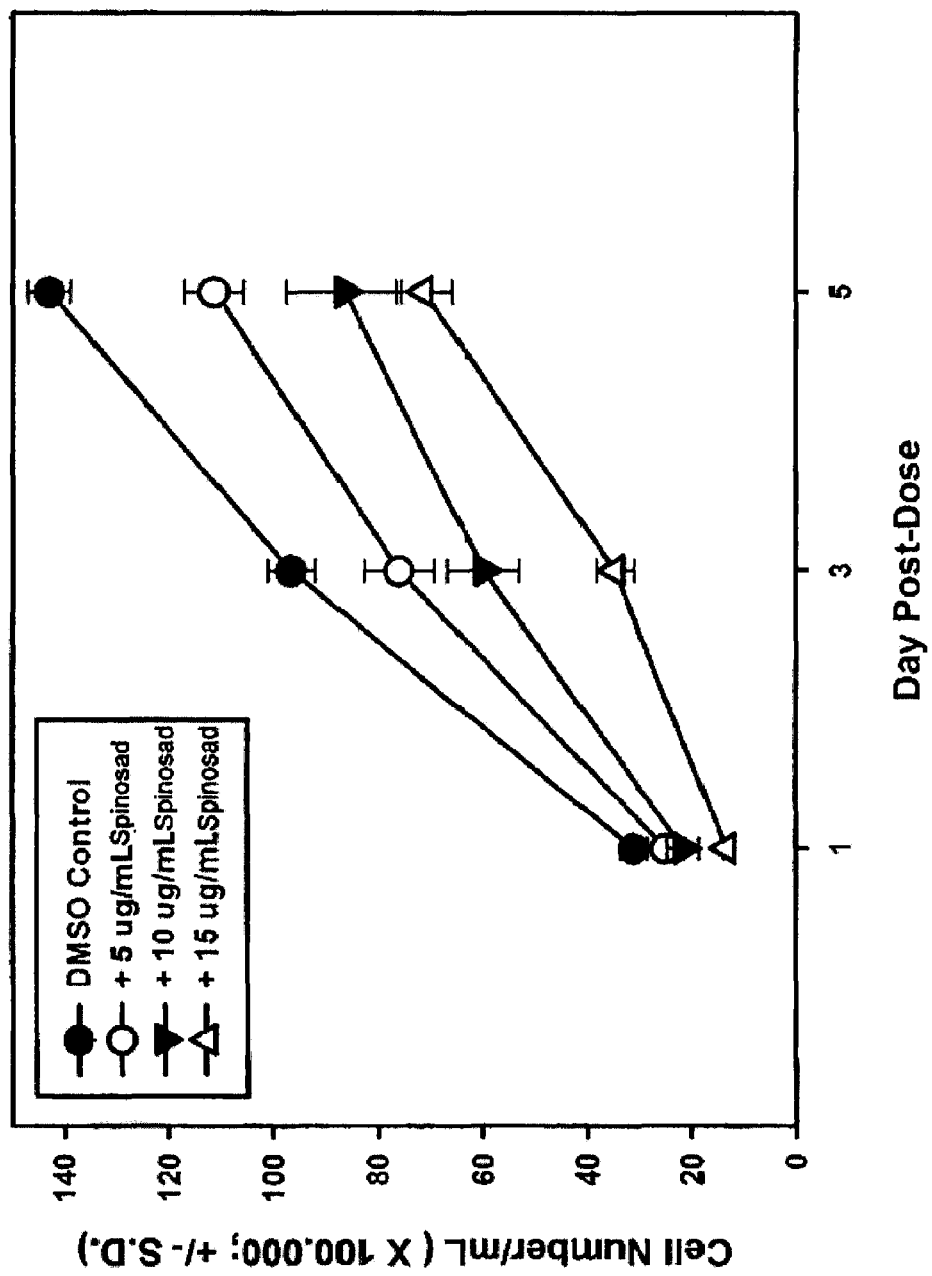
FIGS. 7A-7D shows the effect of spinosad on cancer cells proliferation
Figure 7B:
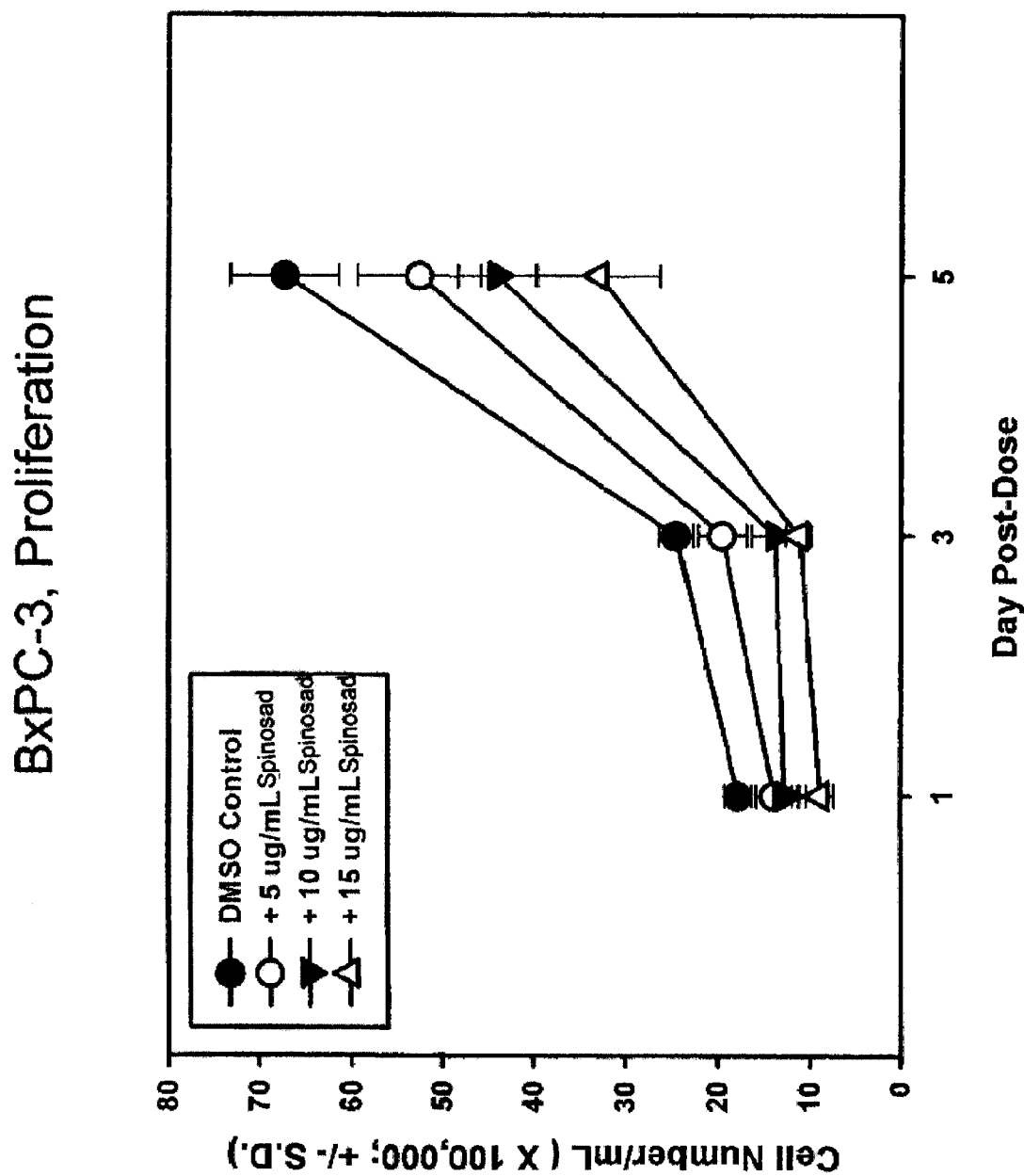
Figure 7C:
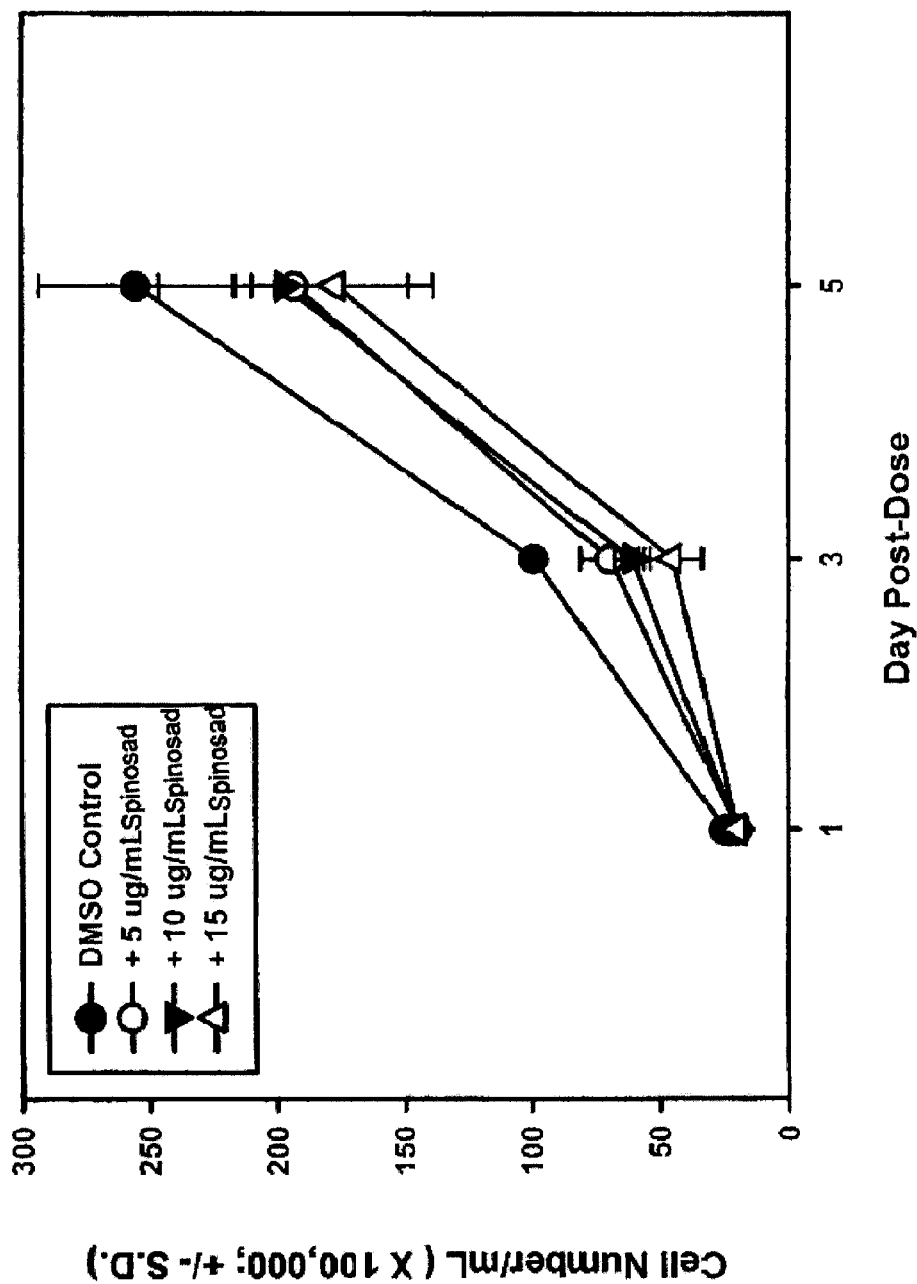
Figure 7D:
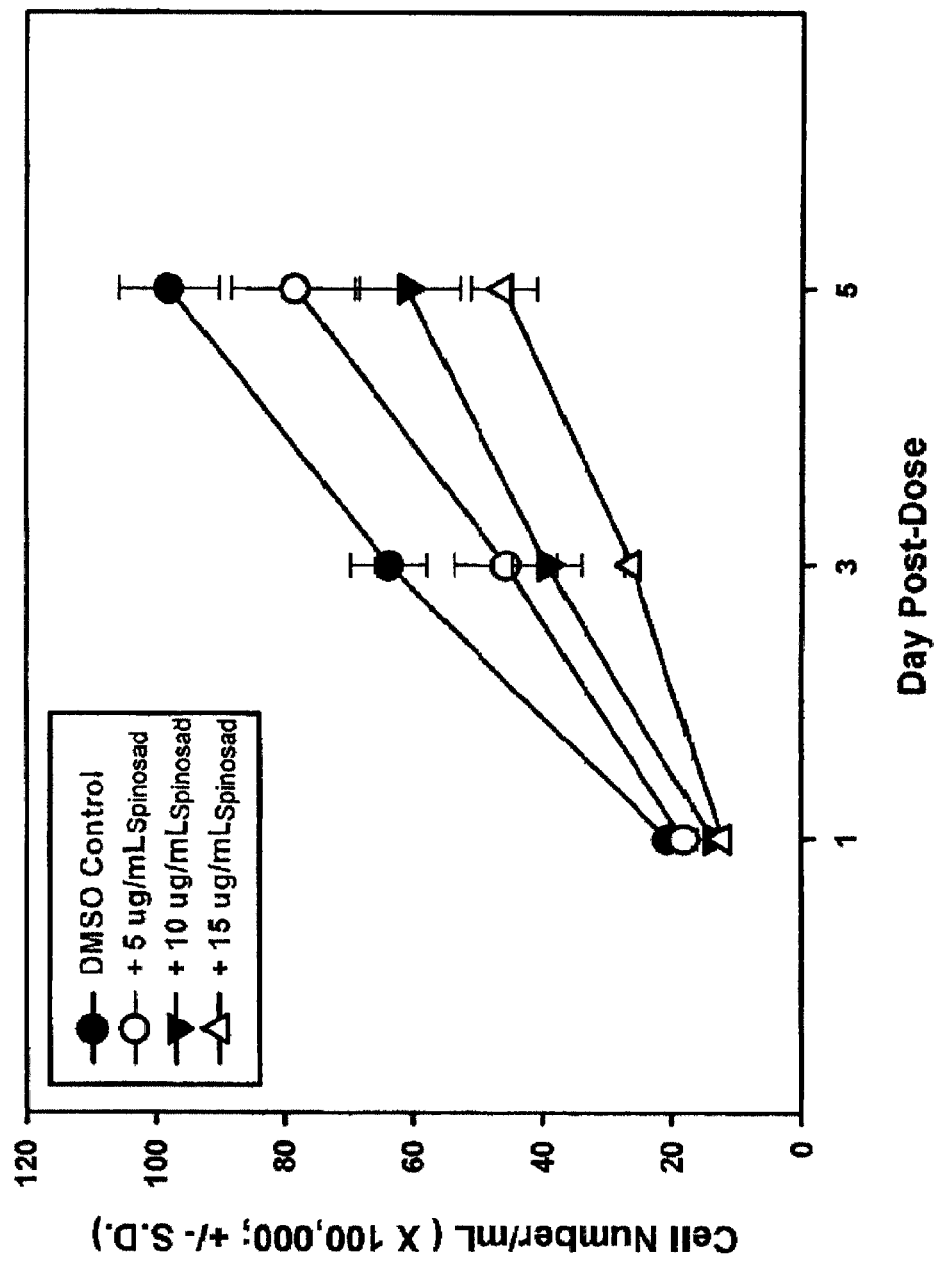
Figure 8C:
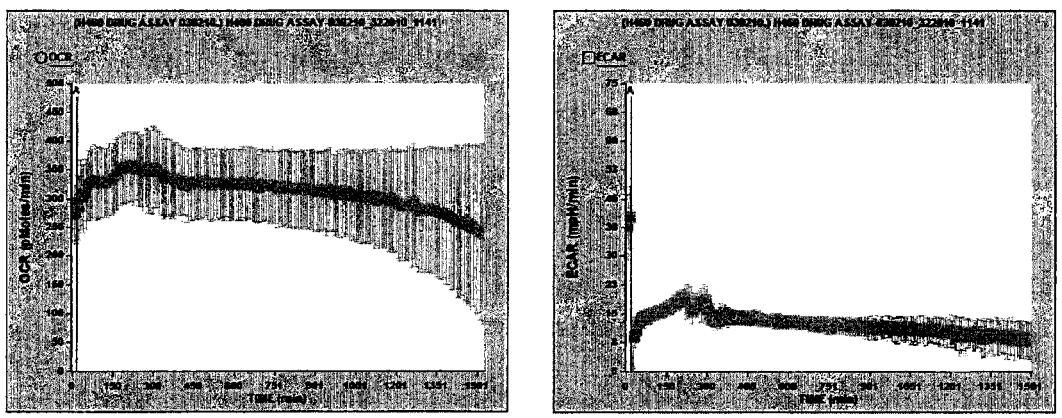
Figure 8D:
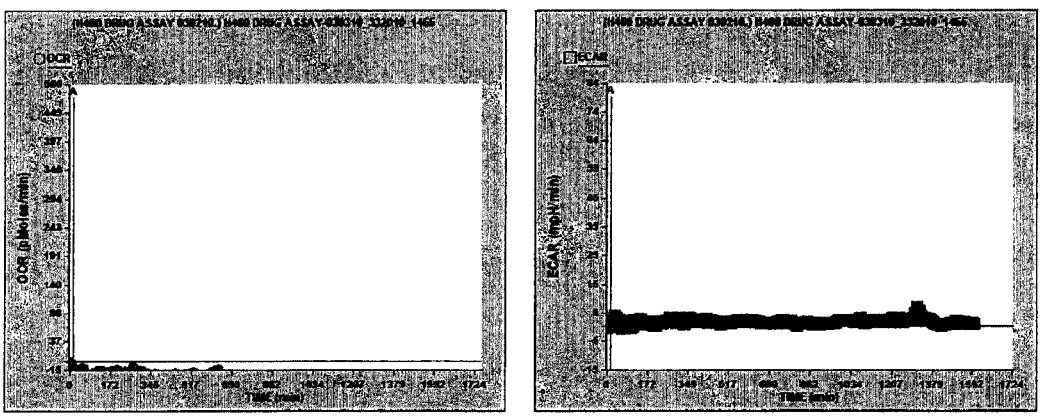
Figure 10:
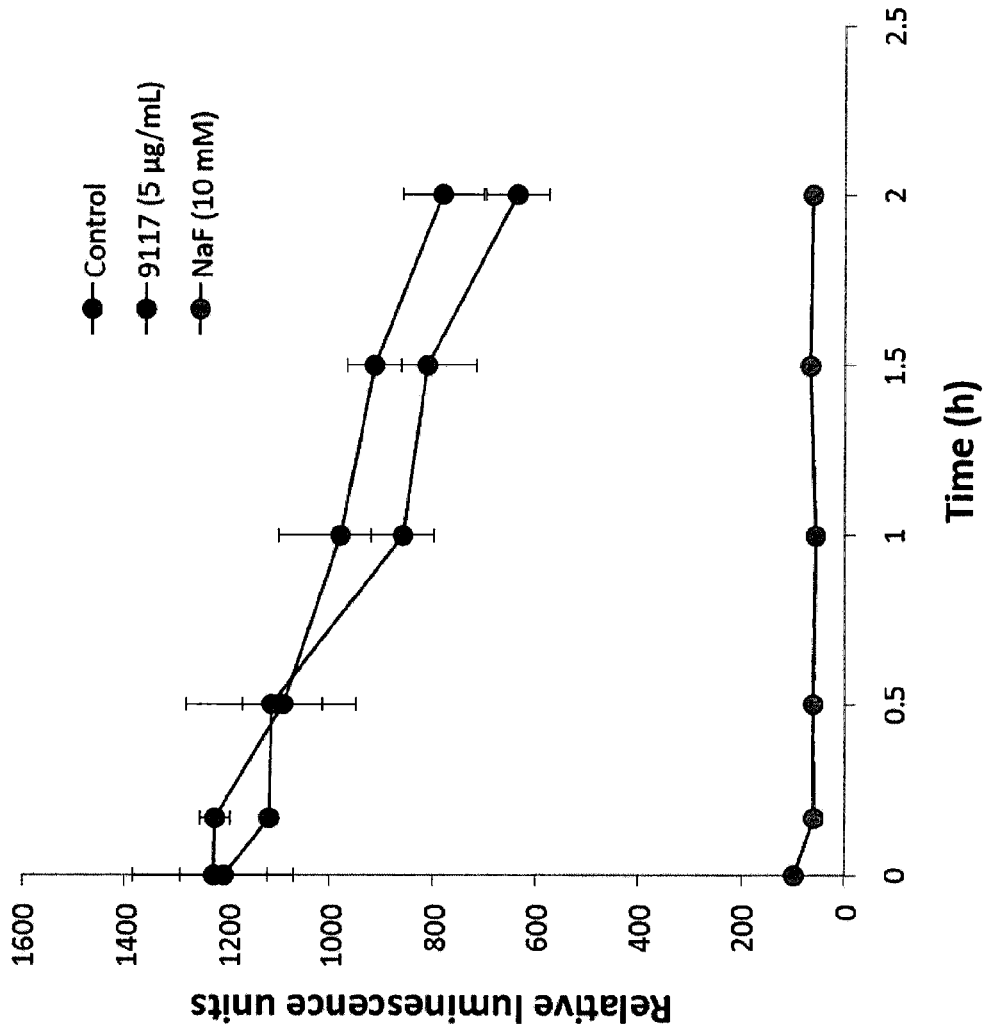
FIG. 10 shows the ATP levels in isolated *Plasmodium* parasites incubated in saline/spinosad medium
Figure 11:
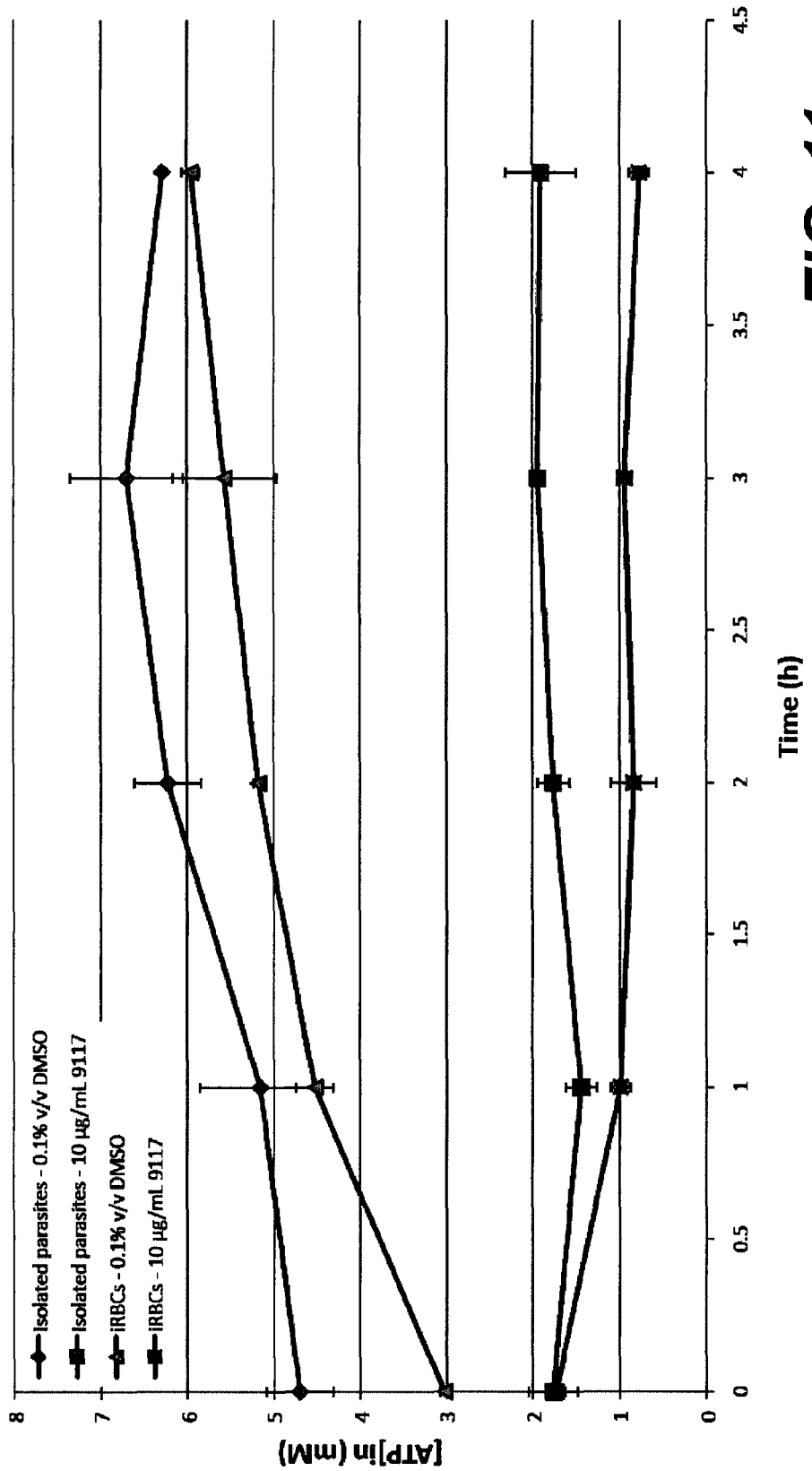
FIG. 11 shows the ATP levels in isolated *Plasmodium* parasites incubated with RPMI/spinosad medium and parasites isolated from *Plasmodium*-infected erythrocytes incubated in RPMI/spinosad medium
Figure 12:
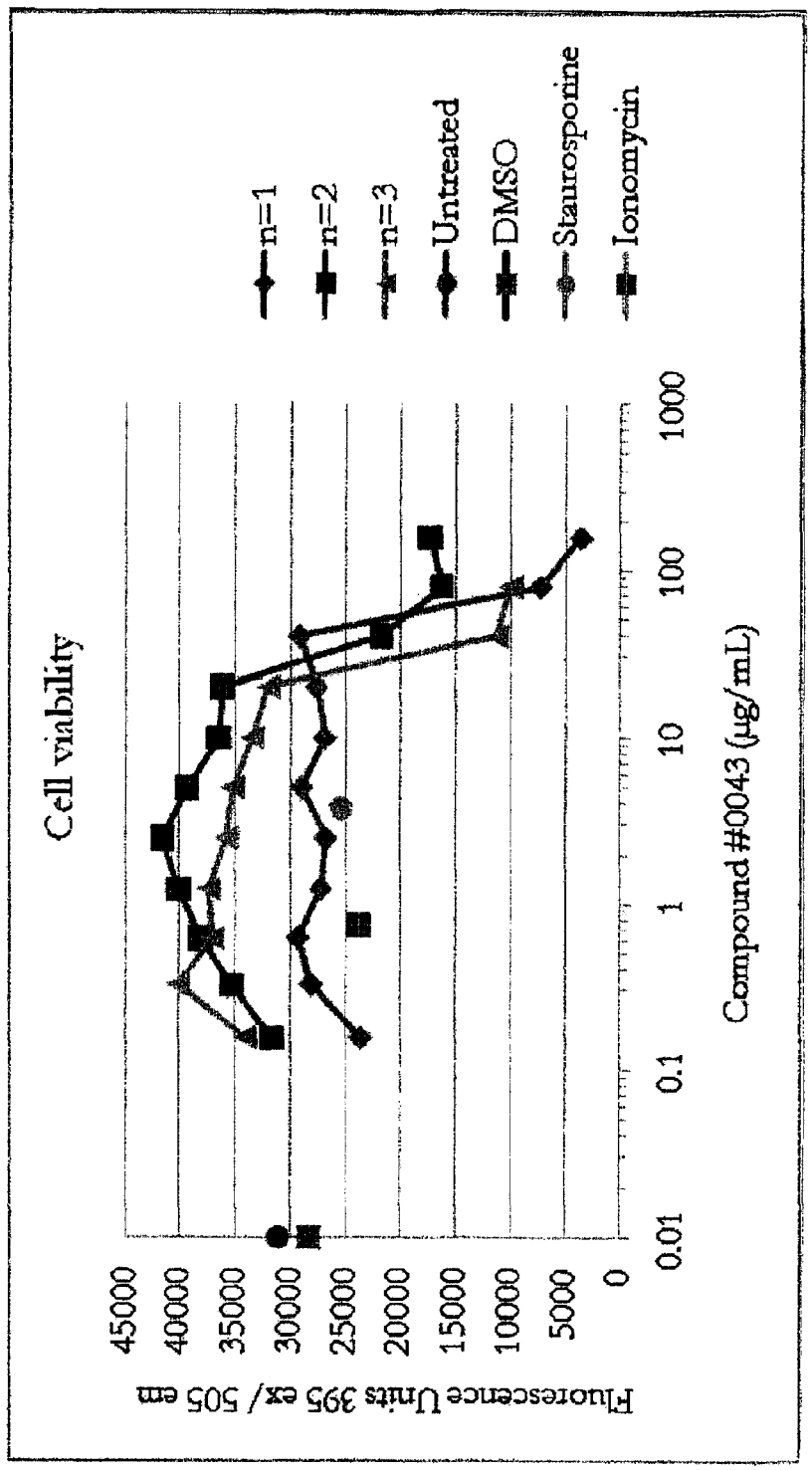
FIG. 12 shows the dose response curve on H460 cell viability, after 3 hours treatment with various concentrations of spinosad
Figure 13:
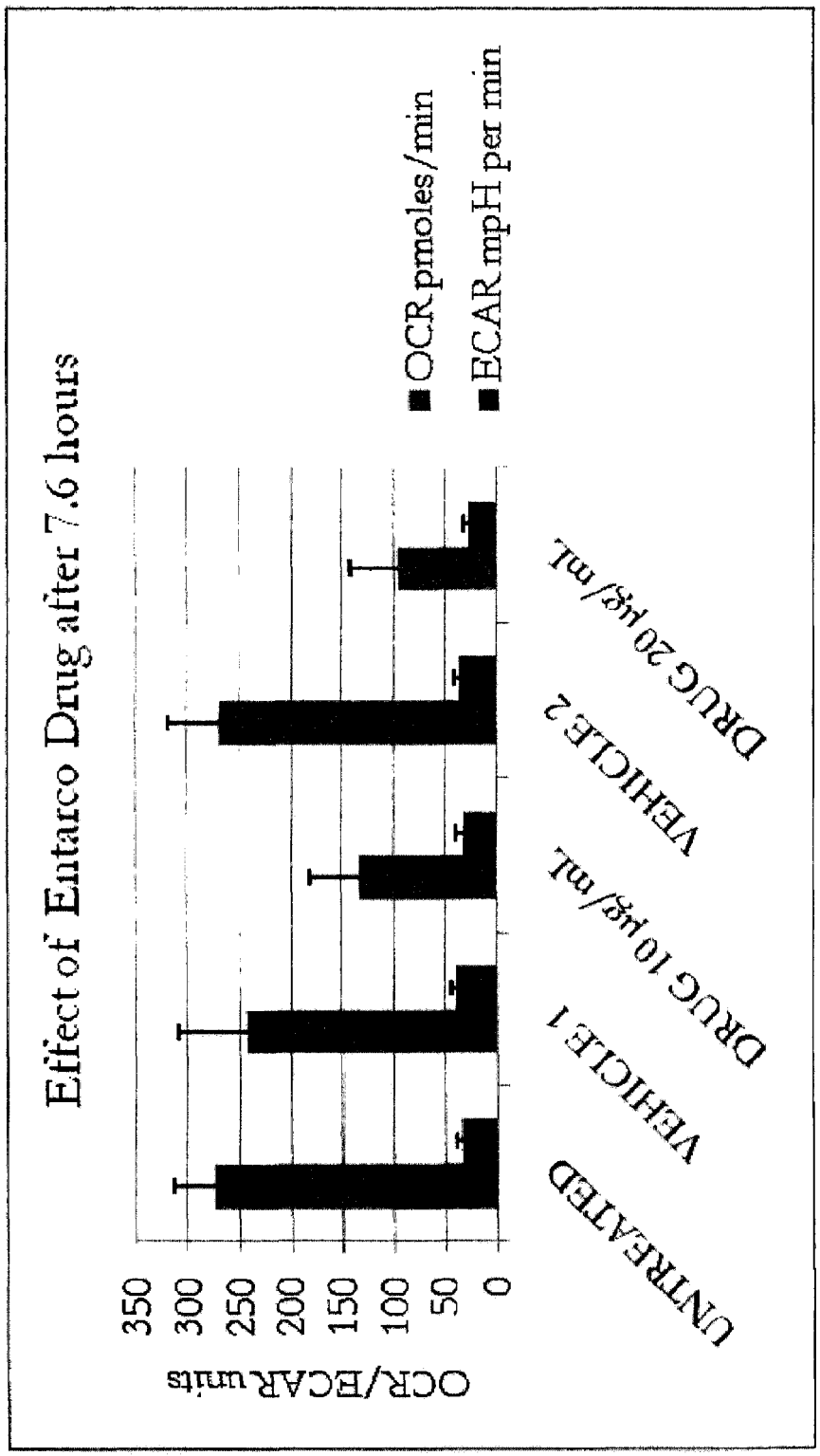
FIG. 13 shows the effect of two spinosad concentrations, 10 μg/ml and 20 μg/ml, on OCR and ECAR of H460 cells, 7.6 hours post treatment
Figure 14:
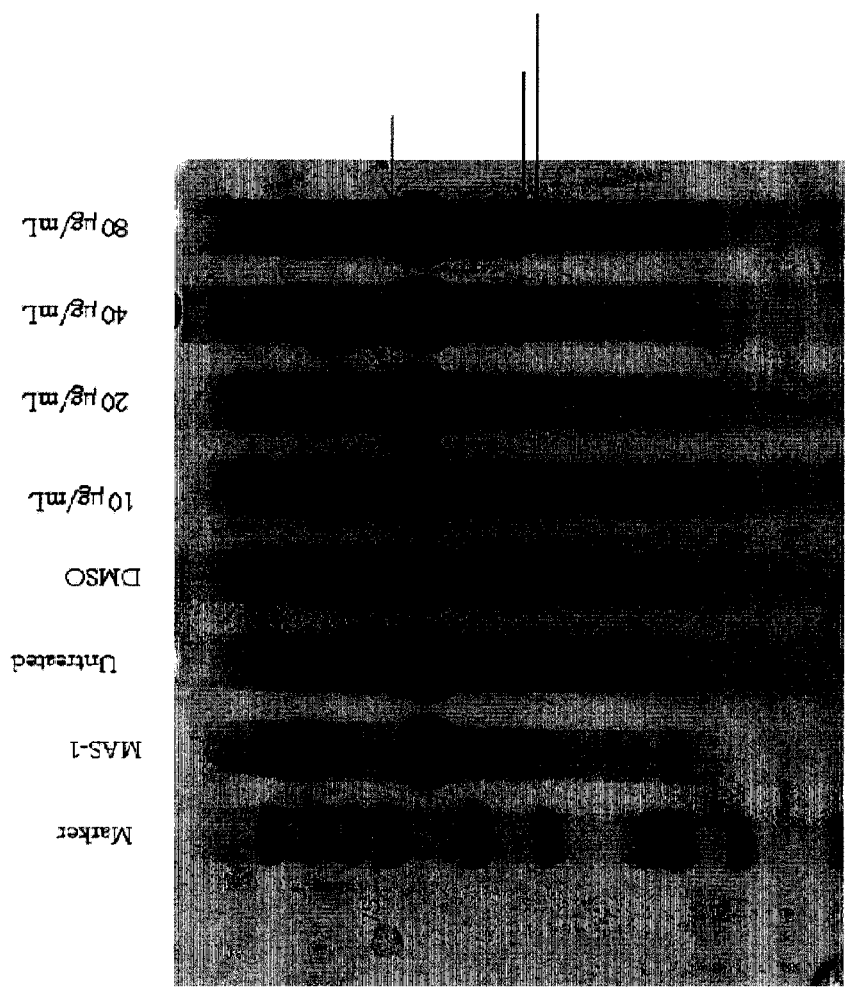
FIG. 14 shows the SDS-PAGE of samples untreated, DMSO and spinosad treated, analyzed by the Seahorse XF24 analyzer.

What is claimed is:

1. A method of treating a host suffering from a viral infection caused by a virus belonging to the family of Herpesviridae, comprising administering to said host a therapeutically effective amount of a composition comprising at least one spinosyn or salt thereof and a suitable carrier.

2. The method of claim 1, wherein the virus is selected from at least one or more serotypes and subtypes of the Herpes Simplex Virus 1 (HSV1), Herpes Simplex Virus 2 (HSV2), and varicella-zoster virus.

3. The method of claim 1, wherein the spinosyn is chosen from at least one or more of spinosyn A, spinosyn D, spinosad, or spinetoram.

4. The method of claim 1, wherein the spinosyn is chosen from at least one or both of spinosyn A and spinosyn D.

5. The method of claim 1, wherein the spinosyn is administered to the host in a dose of 0.05 μg/kg body weight daily to 2000 mg/kg body weight daily, once or in multiple doses or by continuous infusion.

6. The method of claim 1, wherein the spinosyn is administered to the host in a dose of 5 mg/kg body weight daily to 200 mg/kg body weight daily, once or in multiple doses or by continuous infusion.

7. The method of claim 1, wherein at least one additional active agent is administered to the host simultaneously, separately or sequentially.

8. The method of claim 7, wherein the at least one additional agent is chosen from one or more of an antiprotozoan, another antiviral, an anticancer agent, a biocide, an enzyme inhibitor, an antimetabolite, a vinca alkaloid, an alkylating agent, a polypeptide, an antibody, a vitamin, an immunostimulant, an interferon, a cytokine, an antibacterial agent, an antinematode, an anticestode, and an antitrematode agent contained in the same spinosyn composition or in different compositions.

9. The method of claim 1, wherein the host is a human.

10. The method of claim 1, wherein the host is an animal.

11. The method of claim 1, wherein the spinosyn composition is administered simultaneously, separately or sequentially with one or more of Acyclovir, Cidofovir, Cytarabine, Dideoxyadenosine, Didanosine, Edoxudine, Famciclovir, Floxuridine, Inosine Pranobex, Lamivudine, MADU, Penciclovir, Sorivudine, Stavudine, Trifluridine, Valacyclovir, Vidarabine, Zalcitabine, Zidovudine,Zanamivir, Amantadine, Zidovudine (ATZ), Delavirdine, Indinavir, Interferon-$\alpha$, Interferon-$\beta$, Interferon-$\gamma$, Kethoxal, Methisazone, Moroxydine, Nevirapine, Oseltamivir, Pleconaril, Podophyllotoxin, Rifampicin, Ribavirin, Rimantadine, Ritonavir, Saquinavir contained in the same spinosyn composition or in different compositions.

12. The method of claim 1, wherein the composition is administered to the host enterally, parenterally, or topically.

13. The method according to claim 1, wherein said administering is repeated periodically.

14. The method of claim 1, wherein the composition comprising at least one spinosyn or salt thereof is administered to the host topically in a dose of 0.05 $\mu g/cm^2$ to 50 $mg/cm^2$.

15. The method of claim 1, wherein the composition is in the form of one or more of a solution, dispersion, suspension, emulsion, solution or powder for injection, patch, implantable delivery system, aerosol, capsule, tablet, pill, lozenge, hydrogel, cream, colloidal dispersion system, nanoparticle or liposome.

* * * * *